(12) United States Patent
Jung et al.

(10) Patent No.: US 8,288,614 B2
(45) Date of Patent: Oct. 16, 2012

(54) GRAIN QUALITY THROUGH ALTERED EXPRESSION OF SEED PROTEINS

(75) Inventors: Rudolf Jung, Des Moines, IA (US); Wang-Nan Hu, Johnston, IA (US); Robert B. Meeley, Des Moines, IA (US); Vincent J.H. Sewalt, West Des Moines, IA (US); Ramesh Nair, Ankeny, IA (US)

(73) Assignee: Pioneer Hi Bred International, Inc, Johnston, IA (US)

( * ) Notice: Subject to any disclaimer, the term of this patent is extended or adjusted under 35 U.S.C. 154(b) by 15 days.

(21) Appl. No.: 12/684,441

(22) Filed: Jan. 8, 2010

(65) Prior Publication Data

US 2010/0235944 A1  Sep. 16, 2010

Related U.S. Application Data

(63) Continuation of application No. 11/063,325, filed on Feb. 22, 2005, now Pat. No. 7,741,533, which is a continuation-in-part of application No. 11/011,526, filed on Dec. 14, 2004, now abandoned, which is a continuation-in-part of application No. 10/053,410, filed on Nov. 7, 2001, now Pat. No. 6,858,778.

(60) Provisional application No. 60/246,455, filed on Nov. 7, 2000.

(51) Int. Cl.
| | |
|---|---|
| *A01H 1/00* | (2006.01) |
| *C12N 15/82* | (2006.01) |
| *C12N 15/86* | (2006.01) |
| *C07H 21/04* | (2006.01) |

(52) U.S. Cl. ........ 800/285; 800/286; 800/284; 536/24.5

(58) Field of Classification Search ................. None
See application file for complete search history.

(56) References Cited

U.S. PATENT DOCUMENTS

| | | | |
|---|---|---|---|
| 5,929,311 A | 7/1999 | Williams | |
| 6,160,208 A | 12/2000 | Lundquist et al. | |
| 6,326,527 B1 * | 12/2001 | Kirihara et al. | 800/278 |
| 6,329,574 B1 | 12/2001 | Lundquist et al. | |
| 7,196,255 B2 | 3/2007 | Grote | |
| 7,741,533 B2 * | 6/2010 | Jung et al. | 800/285 |
| 2003/0135888 A1 | 7/2003 | Zhu et al. | |
| 2004/0194171 A1 | 9/2004 | Garcia | |

FOREIGN PATENT DOCUMENTS

| | | |
|---|---|---|
| WO | WO98/26064 | 6/1998 |
| WO | WO2004/022759 | 3/2004 |
| WO | WO2007/024207 | 3/2007 |

OTHER PUBLICATIONS

Bowie et al., (1990) Science 247:1306-1310.
McConnell et al., Roe of Phabulosa and Phavoluta in determining radial patterning in shoots (2001) Nature 411:709-713.
Fourgoux-Nicol, et al., Isolation of rapeseed genes expressed early and specifically during development of the male gametophyte (1999) Plant Molecular biology, 40:857-872.
Shorrosh et al., (1999) NCBI Accession No. X63990.
Woo et al., Genomics Analysis of Genes Expressed in Maize Endosperm Identifies Novel Seed proteins and Clarifies Patterns of Zein Gene Expressoin (2001) Plant Clel 13:2297-2317.
Huang et al., Improving Nutritional Quality of Maize Proteins by Expressing Sense and Antisense Zein Genes, J. Agric. Food Chem. (2004) 52(7):1958-1964.
Segal et al., A New Opaque Variant of Maize by a Single Dominant RNA-Interference-Inducing Transgene, Genetics (2003) 165:387-397.
Azevedo, et al., Regulation of Maize Lysine Metabolism and endosperm protein synthesis by opaque and floury mutations, (2003), Eur. J. Biochem, 270:4898-4908, XP002502337.
Landry, et al., Protein Distribution Pattern in Floury and Vitreous Endosperm of Maize Grain, Cereal Chemistry, (2004), 81(2):153-158, XP009110813.
Dannenhoffer, et al., Opaque-15, a maize mutatoin with properties of a defective opaque-2 modifier, Proc. Natl. Acad. Sci. USA, (1995), 92:1931-1935, XP002518903.
Tacke, et al., The Plant Journal 8:907-917 1995.

* cited by examiner

*Primary Examiner* — Li Zheng

(74) *Attorney, Agent, or Firm* — Pioneer Hi-Bred, Int'l, Inc.

(57) ABSTRACT

The present invention is directed to compositions and methods for altering the levels of seed proteins in cereal grain. The invention is directed to the alteration of seed protein levels in plant grain, resulting in grain with increased digestibility/nutrient availability, improved amino acid composition/nutritional value, increased response to feed processing, improved silage quality, and increased efficiency of wet milling.

9 Claims, No Drawings

GRAIN QUALITY THROUGH ALTERED EXPRESSION OF SEED PROTEINS

CROSS REFERENCE TO RELATED APPLICATIONS

This application is a continuation of U.S. application Ser. No. 11/063,325 filed Feb. 22, 2005, now U.S. Pat. No. 7,741,533, which is a continuation-in-part application of U.S. application Ser. No. 11/011,526 filed Dec. 14, 2004, now abandoned, which is a continuation-in-part of U.S. application Ser. No. 10/053,410 filed Nov. 7, 2001, now U.S. Pat. No. 6,858,778, and claims the benefit of U.S. Application Ser. No. 60/246,455 filed Nov. 7, 2000, all of which are herein incorporated by reference.

FIELD OF THE INVENTION

The invention relates to the field of plant molecular biology and the use of genetic modification to improve the quality of crop plants, more particularly to methods for improving the nutritional value of grain and the efficiency of grain processing.

DETAILED DESCRIPTION OF THE INVENTION

The present invention is directed to compositions and methods for altering the levels of seed proteins in plant seed, particularly reducing the levels of gamma-zein proteins in maize and the levels of kafarin in sorghum. Modification of seed protein composition causes changes in the physical and/or chemical properties of the grain.

Corn is a major crop used as a human food source, an animal feed, and as a source of carbohydrate, oil, protein and fiber. It is principally used as an energy source in animal feeds.

Most corn grain is handled as a commodity, since many of the industrial and animal feed requirements for corn can be met by common varieties of field corn which are widely grown and produced in volume. However, there exists at present a growing market for corn with special end-use properties which are not met by corn grain of standard composition.

*Sorghum* (*Sorghum bicolor*), one of the most important staple crops in Africa, represents the fifth most important cereal crop in the world. It is the only viable food grain for many of the world's most food insecure people, and can make critically important contributions to nutrition of families and children affected by AIDS and other pandemics.

The invention is directed to the alteration of protein composition and levels in plant seed, resulting in grain with increased digestibility, increased energy availability, increased response to feed processing, improved silage quality, increased efficiency of wet or dry milling, and decreased anti-nutritional properties. The claimed sequences encode proteins preferentially expressed during seed development.

Typically, "grain" means the mature kernel produced by commercial growers for purposes other than growing or reproducing the species, and "seed" means the mature kernel used for growing or reproducing the species. For the purposes of the present invention, "grain", "seed", and "kernel", will be used interchangeably.

Additionally, the invention is directed to altering seed hardness, decreasing seed caloric value for use in diet foods and other food for human use, pet food, increasing the antioxidant properties of seed, and taking advantage of the metal chelating properties of the corn legumin 1 protein to purify other polypeptides of interest and to increase iron and zinc content and bioavailability in the grain.

As used herein, "genetically modified" or "genetically altered" means the modified expression of a seed protein resulting from one or more genetic modifications; the modifications including but not limited to: recombinant gene technologies, induced mutations, and breeding stably genetically modified plants to produce progeny comprising the altered gene product.

Compositions of the invention comprise sequences encoding maize seed proteins and variants and fragments thereof. Methods of the invention involve increasing or inhibiting a seed protein by such means as, but are not limited to, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering (see Nobrega et. al., Nature 431:988-993(04)), homologous recombination, TILLING (Targeting Induced Local Lesions In Genomes), and biosynthetic competition to manipulate, in plants and plant seeds and grains, the expression of seed proteins, including, but not limited to, those encoded by the sequences disclosed herein.

Further provided is a isolated nucleic acid molecule comprising a nucleotide sequence encoding an allele of the 27 kD gamma-zein maize protein herein designated "QPM" allele that improves the kernel properties of o2 maize have kernel opacity, and fragments and variants thereof.

Transgenic plants producing seeds and grain with altered seed protein content are also provided.

The genetically modified seed and grain of the invention can also be obtained by breeding with transgenic plants, by breeding between independent transgenic events, by breeding of plants with one or more alleles (including mutant alleles) of genes encoding abundant seed proteins and by breeding of transgenic plants with plants with one or more alleles (including mutant alleles) of genes encoding abundant seed proteins. Breeding, including introgression of transgenic and mutant loci into elite breeding germplasm and adaptation (improvement) of breeding germplasm to the expression of transgenes and mutant alleles, can be facilitated by methods such as by marker assisted selected breeding. The 50 kD gamma-zein of the instant invention maps to chromosome 7, bin 7.03, the 18 kD alpha-globulin to chromosome 6, bin 6.05, and the 50 kD legumin 1 to chromosome 6, Bin 6.01. This information, as well as the map location for 15 kD beta zein, for 16 kD and 27 kD gamma-zein, the map location of members of the alpha-zein gene families, the map location for the 10 kD and 18 kD delta zeins (see Table 1 in Woo et al., 2001, Plant Cell 13:2297-2317) enables one of skill in the art to employ these map locations to generate improved maize lines with altered seed protein profiles and levels.

A well-known mutation that improves the amino acid composition and protein quality of maize is the opaque-2 (o2) mutation, which is a mutation of a regulatory locus which regulates a number of other genes (i.e., the bZIP transcription factor). The o2 mutation is inherited as a simple Mendelian recessive trait and regulates zein gene transcription, particularly that of the most abundant alpha-zein. The o2 mutation causes a reduction of the 19 and 22 kD alpha-zein in the endosperm and an increase in non-zein storage proteins. Unfortunately, the o2 mutation also has the significant disadvantage of producing a soft, starchy endosperm. This starchy kernel texture adversely affects characteristics of the o2 grain, including the grain's susceptibility to insect pests, the yield of grits from dry milling, the energy costs of wet milling, and the baking properties of the flour. The relationship between the opaque kernel phenotype and zein synthesis is not well understood.

To overcome the deficiencies associated with the o2 kernel texture, maize breeders combined the o2 mutation with a number of modifier genes to create new maize inbreds. These inbreds, which are collectively called Quality Protein Maize (QPM) retain the high lysine and tryptophan content of the o2 mutation but have hard, translucent (i.e., "vitreous") kernels.

Despite the success of QPM in tropical and subtropical regions, QPM hybrids remain unpopular in developed countries due to the relative lack of understanding of the nature and quantity of the o2 modifier genes and the concomitant difficulty in integrating the modifiers into commercial breeding programs. Thus, there remains a need to produce maize grain that has both a balanced amino acid composition and a hard, vitreous kernel phenotype. There also remains a need for methods to produce such maize grain easily, ideally via a transgenic approach.

It is recognized that while the invention is exemplified by the modulation of expression of selective sequences in maize, similar methods can be used to modulate the levels of seed proteins in other plants, particularly other cereals such as sorghum. In this manner, the sequences of the invention can be used to identify and isolate similar sequences in other plants based on sequence homology or sequence identity. Alternatively, Where the maize sequences share sufficient homology to modulate expression of the native genes, such as in sorghum, the maize sequences can be used to modulate expression in sorghum. For a review of sorghum seed proteins including kafarin see Leite et al., *The Prolamins of Sorghum, Coix and Millets.*, In: Shewry and Casey (eds.) (1999) Seed Proteins, 141-157, Academic Publishers, Dordrecht.

*Sorghum* grain has a nutritional profile similar to corn and other cereals (Shewry and Halford, *Journal of Experimental Botany* 53 (570):947-958 (2002), i.e. it shares the typical nutritional deficiencies of cereal grains, a low content of the essential amino acids lysine, threonine, tryptophan and sulphur amino acids; and a low bio-availability of iron and zinc. Therefore, a diet, based mostly on sorghum, is not adequate to meet the nutritional growth or maintenance requirements for children and adults and needs to be supplemented with essential amino acids and micronutrients. Further, most sorghum food is cooked or heated during preparation. In contrast to other cereal grains, heat treatment results in a severely reduced digestibility of sorghum grain (up to 50%).

The proteins of the present invention have been designated for the purposes of this invention as "abundant seed proteins". In maize, a single species (that is a polypeptide encoded by a specific gene) or a group of similar species (that are protein family members with similar molecular properties like size) of these proteins make up 1% or more by dry weight of the total protein of seed and a single protein species or a group of similar species can be visualized by commonly used protein analytical methods such as gel electrophoresis and detection of proteins by staining of protein bands with Coomassie Blue or by liquid chromatography and detection of protein peaks by means of a UV detector (ref: Walker, J M, (2002) *The Protein Protocol Handbook*, second edition, Humana Press, Totowa, N.J.). Although these proteins are "abundant" in the majority of maize lines (hereafter referred to simply as maize) they may be of low abundance or even absent in specific maize lines or can be transgenically manipulated to become suppressed.

Additionally, these proteins may originally not be "abundant" in grain from wild-type maize but be structurally related to proteins found abundantly in seeds of other plant species. For example, legumins are abundant proteins in legumes and rice but corn legumin is a protein of lower abundance in grain from common maize. Thus we refer to corn legumin as an "abundant seed protein". Traditionally "abundant seed proteins" as defined herein have also been called "seed storage proteins" as they are the major source for nitrogen and amino acids to provide nutrients for seedling growth and development.

These abundant seed proteins can occur as major seed proteins and minor seed proteins.

In cereals, a major group of seed proteins is prolamins. Prolamins are typically characterized by being extractable in 70% ETOH and a reducing agent (see Woo et al., 2001, *Plant Cell* 13:2297-2317, and Shewry and Casey (eds.) (1999) Seed Proteins 141-157, Academic Publishers, Dordrecht.). However, prolamins can also be identified phylogenetically through the use of sequence analysis. Zeins are a type of prolamin seed protein found in maize.

The major zein seed proteins include, but are not limited to, the alpha-zeins such as the 19 kDa and 22 kDa alpha-zeins, and the gamma-zeins such as the 27 kDa gamma-zein protein.

The alpha-zeins are a family of related proteins that typically comprise 10-50% of the total protein (based on dry weight) in the grain, i.e. they are major seed proteins. This protein family is further comprised of two 19 kD alpha-zein protein subfamilies and one 22 kD alpha-zein protein subfamily (Woo et al). The chromosomal loci (genomic sequence) of the alpha-zein gene subfamilies have been sequenced in their entirety for a common maize inbred line and are known to the art (ref: Song R., Messing J, (2002) *Plant Physiol*, Vol. 130, pp. 1626-1635, Song R, Llaca V, Linton E, Messing J. (2001) *Genome Res.* 11, pp. 1817-25).

The gamma-zeins are a family of related proteins that typically make up 10-15% of the total seed proteins (based on dry weight). The structure and characteristics of this family are exemplified by the 16 kD gamma-zein, the 27 kD gamma-zein—which are major seed proteins—and the 50 kDa gamma-zein—a minor seed protein. The 15 kD beta-zein is a minor seed protein and belongs to this family as well (Woo et al).

Non-zein abundant seed proteins in cereal crops include, but are not limited to, the globulin proteins The globulin proteins include, but are not limited to legumin and alpha-globulins. The corn legumins and the corn alpha-globulins are examples of globulins that are minor seed proteins in maize; the name designation of both proteins are based on their phylogentic relationship to seed proteins from other species (Woo et al.). Seed proteins have been traditionally characterized based on solubility characteristics (Shewry and Casey (eds.) (1999) *Seed Proteins,* 141-157, Academic Publishers, Dordrecht). Thus most seed proteins are either extractable in aqueous alcoholic solutions (prolamins), extractible in aqueous solutions of low ionic strength (albumins), or extractable in aqueous solutions of high ionic strength (globulins). The classification of seed proteins by extraction methods is well known in the art (Shewry and Casey (1999)). However it is also common to designate seed proteins with unknown extraction characteristics as globulins, albumins, or prolamins if they are phylogenetically or sequence-related to proteins that have originally been classified based on extraction experiments. Therefore, it is a common practice to name seed proteins based on their phylogenetic association rather then their extraction properties. The name of a seed protein gene may therefore not reflect the properties of the encoded protein in a strict sense.

It has been recently discovered that down regulation or inhibition of the zein proteins alone or in combination increases digestibility and the energy availability of cereal grain such as corn and sorghum.

Additionally, the novel discovery has been made that the up regulation (or overexpression) of the non-zein proteins increases digestibility of cereal grain.

In one embodiment of the present invention, zein proteins are down regulated in combination with over expression of non-zein proteins to produce a synergistic effect of increased digestibility of cereal grain.

The present invention provides isolated nucleic acid molecules comprising a nucleotide sequence encoding a maize protein, designated herein as the 50 kD gamma-zein, having the amino acid sequence shown in SEQ ID NO:2. Further provided is a polypeptide having an amino acid sequence encoded by the nucleic acid molecules described herein, for example that set forth in SEQ ID NO:1 and fragments and variants thereof.

The present invention also provides isolated nucleic acid molecules comprising a nucleotide sequence encoding a maize protein, herein designated as the 18 kD alpha-globulin, having the amino acid sequence shown in SEQ ID NO:4. Further provided is a polypeptide having an amino acid sequence encoded by the nucleic acid molecules described herein, for example that set forth in SEQ ID NO:3, and fragments and variants thereof.

The present invention also provides isolated nucleic acid molecules comprising a nucleotide sequence encoding a maize protein, herein designated as the 50 kD legumin 1 protein, having the amino acid sequence shown in SEQ ID NO:6. Further provided is a polypeptide having an amino-acid sequence encoded by the nucleic acid molecules described herein, for example that set forth in SEQ ID NO:5, and fragments and variants thereof.

The present invention also provides isolated nucleic acid molecules comprising a nucleotide sequence encoding a sorghum protein, herein designated as the *sorghum bicolor* 50 kD legumin 1 protein, having the amino acid sequence shown in SEQ ID NO:23. Further provided is a polypeptide having an amino-acid sequence encoded by the nucleic acid molecules described herein, for example that set forth in SEQ ID NO:22, and fragments and variants thereof.

The present invention also provides isolated nucleic acid molecules comprising a nucleotide sequence encoding a sugar cane protein, herein designated as the *Saccharum officinale* 50 kD legumin 1 protein, having the amino acid sequence shown in SEQ ID NO:25. Further provided is a polypeptide having an amino-acid sequence encoded by the nucleic acid molecules described herein, for example that set forth in SEQ ID NO:24, and fragments and variants thereof.

A plasmid containing the nucleotide sequence encoding the 50 kD gamma-zein protein was deposited with the Patent Depository of the American Type Culture Collection (ATCC), Manassas, Va., on Jul. 26, 2000 and assigned Patent Deposit No. PTA-2272. A plasmid containing the nucleotide sequence encoding the 18 kD alpha-globulin protein was deposited with the Patent Depository of the American Type Culture Collection (ATCC), Manassas, Va., on Jul. 26, 2000 and assigned Patent Deposit No. PTA-2274. A plasmid containing the nucleotide sequence encoding the 50 kD legumin 1 protein was deposited with the Patent Depository of the American Type Culture Collection (ATCC), Manassas, Va., on Jul. 26, 2000 and assigned Patent Deposit No. PTA-2273. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The present invention also provides isolated nucleic acid molecules comprising a nucleotide sequence encoding an allele of the 27 kD gamma-zein gene that improves the kernel properties of o2 maize and other maize having kernel opacity, and fragments and variants thereof, herein referred to as "QPM" alleles. "QPM allele activity" as used herein refers to the ability of a QPM allele to restore or partially restore a vitreous kernel phenotype in a genetic background in which the level of at least one seed protein has been decreased and in which kernel opacity has increased when compared to an appropriate control plant such as an unmodified plant.

By "decreased" and "increased" is intended that the measurement of a parameter is changed by at least 10%, 20%, 30%, 40%, 50%, 60%, 70%, 80%, 90%, 100%, 200% or more when compared to the measurement of that parameter in a suitable control.

A comparison of the amino acid content of cereal grains shows that 18 kD alpha-globulin is an excellent source of tryptophan and methionine for amino acid balance in all cereals and that 50 kD corn legumin 1 is an excellent source of methionine for all cereals and a good source of lysine and tryptophan for the amino acid balance of most cereals.

The present invention also provides isolated nucleotide sequences comprising transcriptional units for gene over-expression and gene-suppression that have been used either as single units or in combination as multiple units to transform plant cells.

As used herein in connection with abundant seed proteins, "biologically active" means a protein that folds, assemble and interacts with other proteins, is available as a nitrogen source for seed germination and accumulates (ie: synthesis exceeds deposition) during seed development.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the targeted gene. Alternatively, fragments of a nucleotide sequence that are useful as hybridization probes generally do not encode fragment proteins retaining biological activity. In addition, fragments may be used to inhibit the expression of a targeted gene product of interest. Thus, fragments of a nucleotide sequence may range from at least about 10 nucleotides, about 50 nucleotides, about 100 nucleotides, and up to the full-length nucleotide sequence-encoding native alpha-zein proteins, native-gamma-zein proteins, native delta-zein proteins, the native 50 kD gamma-zein, the 18 kD alpha-globulin, or the 50 kD legumin 1 protein of the invention. Similarly, fragments of a nucleotide sequence that are useful for generating cells, tissues or plants transiently or permanently suppressing a gene or genes may not encode fragment proteins retaining biological activity. Fragments may be in sense or antisense or reverse orientation or a combination thereof. Thus, for example, fragments of such nucleotide sequence may range from at least about 10 nucleotides, at least about 20 nucleotides, about 50 nucleotides, about 100 nucleotides, and up to the full-length nucleotide sequence-encoding native alpha-zein proteins, native gamma-zein proteins, native delta-zein proteins, the 50 kD gamma-zein, the 18 kD alpha-globulin, or the 50 kD legumin 1 protein of the invention.

Fragments of the maize nucleotide sequences of the invention (SEQ ID NO:1, SEQ ID NO:3, or SEQ ID NO:5) that encode a biologically active portion of the 50 kD gamma-zein protein, the 18 kD alpha-globulin protein, or the 50 kD legumin 1 protein of the invention, respectively, will encode at least 15, 25, 30, 50, 100, 150, or 200 contiguous amino acids, or up to the total number of amino acids present in the full-length 50 kD gamma-zein protein, the 18 kD alpha-globulin protein, or the 50 kD legumin 1 protein of the invention (for example, 295 amino acids for SEQ ID NO:1; 206 amino acids for SEQ ID NO:3; and 483 amino acids for SEQ ID NO:5). Fragments of SEQ ID NO:1, SEQ ID NO:3, and SEQ ID NO:5 that are useful as hybridization probes or PCR primers need not encode a biologically active portion of a prolamin protein.

Thus, a fragment of SEQ ID NO:1, SEQ ID NO:3, or SEQ ID NO:5 may encode a biologically active portion of a prolamin or globulin protein, or it may be a fragment that can be used as a hybridization probe or PCR primer using methods disclosed below or it may be used to inhibit the expression of the protein. A biologically active portion of the 50 kD gamma-zein protein, the 18 kD alpha-globulin protein, or the 50 kD legumin 1 protein of the invention can be prepared by isolating a portion of the disclosed nucleotide sequence that codes for a portion of the 50 kD gamma-zein protein, the 18 kD alpha-globulin protein, or the 50 kD legumin 1 protein (e.g., by recombinant expression in vitro), and assessing the activity of the encoded portion of the prolamin protein. Nucleic acid molecules that are fragments of SEQ ID NO:1 comprise at least 40, 50, 75, 100, 150, 200, 250, 300, 350, 400, 450, 500, 550, 600, 650, 700, 800, 900, 1000, or 1100 nucleotides, or up to the number of nucleotides present in the full-length gamma-zein cDNA (for example, 1129 nucleotides for SEQ ID NO:1). Nucleic acid molecules that are fragments of SEQ ID NO:3 comprise at least 40, 50, 75, 100, 150, 200, 250, 300, 350, 400, 450, 500, 550, 600, 650, 700, 800, or 900 nucleotides, or up to the number of nucleotides present in the full-length alpha-globulin cDNA (for example, 950 nucleotides for SEQ ID NO:3). Nucleic acid molecules that are fragments of SEQ ID NO:5 comprise at least 40, 50, 75, 100, 150, 200, 250, 300, 350, 400, 450, 500, 550, 600, 650, 700, 800, 1000, 1200, 1400, or 1600 nucleotides, or up to the number of nucleotides present in the full-length legumin 1 cDNA (for example, 1679 nucleotides for SEQ ID NO:5).

By "variants" is intended substantially similar sequences. For nucleotide sequences, conservative variants include those sequences that, because of the degeneracy of the genetic code, encode the amino acid sequence of 50 kD gamma-zein protein, the 18 kD alpha-globulin protein, or the 50 kD legumin 1 protein of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a 50 kD gamma-zein protein, an 18 kD alpha-globulin protein, or an 50 kD legumin 1 protein. Generally, variants of a particular nucleotide sequence of the invention will have at least about 60%, 65%, 70%, 75%, 80%, 85%, 90%, 91%, 92%, 93%, 94%, 95%, 96%, 97%, 98%, or 99% or more sequence identity to that particular nucleotide sequence over a length of 20, 30, 50, or 100 nucleotides or less, as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess all or some of the activity of the native proteins of the invention as described herein. Such variants may result from, for example, genetic polymorphism or from human manipulation. Biologically active variants of the native 50 kD gamma-zein protein, the 18 kD alpha-globulin protein, or the 50 kD legumin 1 protein of the invention will have at least about 60%, 65%, 70%, 75%, 80%, 85%, 90%, 91%, 92%, 93%, 94%, 95%, 96%, 97%, 98%, or 99% or more sequence identity to the amino acid sequence for the native protein over a length of 10, 30, 50, or 100 amino acid residues or less as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the 50 kD gamma-zein protein, the 18 kD alpha-globulin protein, or the 50 kD legumin 1 protein can be prepared by mutations in the DNA. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference.

Thus, the genes and nucleotide sequences of the invention include both the naturally occurring sequences as well as mutant forms. Likewise, the proteins of the invention encompass both naturally occurring variant proteins as well as variations and modified forms thereof. Such variants will continue to be biologically active as defined herein. Obviously, the mutations that will be made in the DNA encoding the variant must not place the sequence out of reading frame and preferably will not create complementary regions that could produce secondary mRNA structure. See EP Patent Application Publication No. 75,444.

Variant nucleotide sequences and proteins also encompass sequences and proteins derived from a mutagenic and recombinogenic procedure such as DNA shuffling. With such a procedure, one or more different alpha-zein, delta-zein, beta-zein, gamma-zein, alpha-globulin, or legumin protein coding sequences can be manipulated to create a new alpha-zein, delta-zein, beta-zein, gamma-zein, alpha-globulin, or legumin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between 50 kD gamma-zein coding sequence, the 18 kD alpha-globulin coding sequence, or the 50 kD legumin 1 protein coding sequence of the invention and other known gene coding sequences to obtain a new coding sequence for a protein with an improved property of interest. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

The nucleotide sequences of the invention and known abundant corn seed proteins can be used to isolate corresponding sequences from other plants. In this manner, methods such as PCR, hybridization, and the like can be used to identify such sequences based on their sequence homology to the sequence set forth herein. Sequences isolated based on their sequence identity to known abundant corn seed proteins and the entire 50 kD gamma-zein, 18 kD alpha-globulin, or 50 kD legumin 1 sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on, for example, the 50 kD gamma-zein sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire 50 kD gamma-zein, 18 kD alpha-globulin, or 50 kD legumin 1 sequence disclosed herein, or one or more portions thereof, may be used as a probe capable of specifically hybridizing to corresponding seed protein sequences and messenger RNAs. To achieve specific hybridization under a variety of conditions, such probes include sequences that are unique among the seed protein sequences of the invention and are preferably at least about 40 nucleotides in length. Such probes may be used to amplify corresponding gamma-zein, alpha-globulin, and legumin 1 sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode polypeptides that function as a seed protein and which hybridize under stringent conditions to the 50 kD gamma-zein, the 18 kD alpha-globulin protein, or the 50 kD legumin 1 sequence disclosed herein, or to fragments thereof, are encompassed by the present invention. Such sequences will be at least about 60%, 65%, 70%, 75%, 80%, 85%, 90%, 91%, 92%, 93%, 94%, 95%, 96%, 97%, 98%, or 99% or more homologous with the disclosed sequence. That is, the sequence identity of sequences may range, sharing at least about 60%, 65%, 70%, 75%, 80%, 85%, 90%, 91%, 92%, 93%, 94%, 95%, 96%, 97%, 98%, or 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local homology algorithm of Smith et al. (1981) Adv. Appl. Math. 2:482; the homology alignment algorithm of Needleman and Wunsch (1970) J. Mol. Biol. 48:443-453; the search-for-similarity-method of Pearson and Lipman (1988) Proc. Natl. Acad. Sci. 85:2444-2448; the algorithm of Karlin and Altschul (1990) Proc. Natl. Acad. Sci. USA 872264, modified as in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

Unless otherwise stated, sequence identity/similarity values provided herein refer to the value obtained using GAP version 10 using the following parameters: identity using GAP Weight of 50 and Length Weight of 3; % similarity using Gap Weight of 12 and Length Weight of 4, or any equivalent program, aligned over the full length of the sequence. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) J. Mol. Biol. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 60%, 65%, 70%, 75%, 80%, 85%, 90%, 91%, 92%, 93%, 94%, 95%, 96%, 97%, 98%, or 99% or more sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 65%, 70%, 75%, 80%, 85%, 90%, 91%, 92%, 93%, 94%, 95%, 96%, 97%, 98%, or 99% or more.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 60%, 65%, 70%, 75%, 80%, 85%, 90%, 91%, 92%, 93%, 94%, 95%, 96%, 97%, 98%, or 99% or more sequence identity to the reference sequence over a specified comparison window. Alignment can be conducted using the homology alignment algorithm of Needleman and Wunsch (1970) J. Mol. Biol. 48:443-453. An indication that two peptide sequences are substantially identical is that one peptide is immunologically reactive with antibodies raised against the second peptide. Peptides that are "substantially similar" comprise a sequence with at least 60%, 65%, 70%, 75%, 80%, 85%, 90%, 91%, 92%, 93%, 94%, 95%, 96%, 97%, 98%, or 99% or more sequence identity or sequence similarity to the reference sequence over a specified comparison window. In this case residue positions that are not identical instead differ by conservative amino acid changes.

The 50 kD gamma-zein nucleotide sequence cloned from a maize endosperm cDNA library (Example 1) and disclosed in the present invention (SEQ ID NO:1) displays sequence similarity to the other two described corn gamma-zein genes, 27 kD gamma-zein (represented herein by GenBank Accession No. P04706) and 16 kD gamma-zein (represented herein by GenBank Accession No. AAA33523). Among the elements common to these prolamins are conserved cysteines (C128, 136, and 156) thought to be involved in disulfide-bond formation critical to proper folding (Ems-McClung et. al., Plant Science, 162(1): 131-141, 2002). The 50 kD gamma-zein was named due to its apparent molecular weight by migration in SDS-PAGE. This cDNA encodes a 295 amino acid protein and also shows sequence similarity to seed proteins of other plant species. For example, wheat alpha-gliadin (GenBank-ID:TAU51305, Accession No. U51305). The 50 kD gamma-zein DNA sequences isolated from different inbred lines showed an unusually low level of polymorphism. Only one single nucleotide polymorphism (SNP) (a 3 bp insertion) was detected along the entire cDNA sequence from DNA isolated from the inbred lines Mo17 and B73. The 50 kD gamma-zein gene has been located on chromosome 7, bin 7.03.

The 18 kD alpha-globulin nucleotide sequence was also cloned from a maize endosperm cDNA library (Example 5) and is disclosed in the present invention (SEQ ID NO:3). The 18 kD alpha-globulin was named due to its similarity to a rice seed globulin (rice alpha-globulin, GenBank Accession No. D50643). This cDNA encodes a 206 amino acid protein. Unlike the case of the 50 kD gamma-zein, there is no other abundantly expressed maize gene known closely related to alpha-globulin in maize. The 18 kD alpha-globulin cDNA shows sequence similarity to seed proteins from other cereals including rice, wheat, and oats and distantly to maize proteins with the conserved domain pfam00234.11 (see below). Different maize inbred lines showed considerable allelism in the 18 kD alpha-globulin gene including SNP's. The 18 kD alpha-globulin gene has been located on chromosome 6, bin 6.05.

Alpha-globulins are accumulated in seed storage tissues during seed development and serve as nitrogen reserves for the growing seedling during germination. They are homologues of abundant seed proteins in other plants (e.g. rice). These seed proteins can therefore be categorized as abundant seed proteins.

Corn alpha-globulin belongs to a plant protein family that is preferentially expressed in seed. This protein family contains the conserved domain pfam00234.11, Tryp_alpha_amyl.

Description: Trypsin-alpha-amylase inhibitor domain, Alpha-Amylase Inhibitor (AAI) subgroup. These cereal-type alpha-amylase inhibitors are composed of 120-160 residues, form 5 disulfide bonds and inhibit amylases from birds, bacilli, insects and mammals. They are related to the other members of the AAI family (plant lipid transfer proteins and seed storage proteins), the disulfide-bonding pattern varies between members.

Polypeptides belonging to this protein family contain three regions with conserved cysteine residues. Members of this gene family from other plant species (e.g. puroindulin from wheat, GenBank Account No. gi_509109) are only about 25% identical to alpha-globulin, but shares the conserved cysteines.

Corn alpha-globulin and rice alpha-globulin (Account No. JC4784) are 46% identical on the amino acid level, but are 80%-100% identical in the cysteine domains.

Domain 1:

The first of these regions (SPLDACRQVLDRQLTG) is 100% identical between rice and corn over 16 aa residues. The Cys residue followed by an Arg residue is conserved also in other members of this protein family found in other plant species.

Domain 2:

The second of these regions (CCQQLQDVSRECR-CAAIR) is 100% identical between rice and corn over 18 aa residues. The two consecutive cysteine residues followed by 9 amino acids and a CysArgCys tripeptide are conserved in other members of this protein family.

The 50 kD legumin 1 nucleotide sequence was also cloned from a maize endosperm cDNA library (Example 8) and is disclosed in the present invention (SEQ ID NO:5). The 50 kD legumin 1 was named due to its similarity to 11S globulins found in other plant species: the so-called legumins. The 50 kD legumin 1 appears to be encoded by a single gene in the maize genome. It belongs to the 11S globulin superfamily and is closely related to legumins from other cereals (also called glutenins in rice and wheat or globulins in oat) and dicot plants. The 50 kD legumin polypeptide sequence may be missing the evolutionary conserved 11S globulin pro-protein proteolytic site (Asn-Gly bond between the acidic chain and basic chain legumin regions) which makes it unique among the legumin protein superfamily (Yamagata, et. al., J. Exp. Bot., 54 (384):913-922, 2003). This cDNA encodes a 483 amino acid protein with a predicted N-terminal endoplasmic reticulum import signal peptide of 36 amino acids. The 50 kD legumin 1 DNA sequences isolated from different inbred lines showed a considerable level of polymorphism. The 50 kD legumin 1 gene has been mapped to chromosome 6, Bin 6.01.

Expressed sequence tags of nucleotide sequences from Sorghum and Sugar Cane indicating a close relationship have been determined in public databases (genebank Account No. for sorghum EST: OV1_21_C09 and for sugar cane EST: CA202717). Clones of cDNA represented by these ESTs have been consequently sequenced in their entirety and are disclosed in the present invention Seq ID 22 and Seq ID 24. The encoded sorghum and sugarcane polypeptides (Seq ID 23 and 25) are closely related to maize 50 kD legumin 1 and share with this protein the unique property of a missing the evolutionary conserved 11S globulin pro-protein proteolytic site.

The chromosomal location of the genes corresponding to the known maize seed proteins and the three cDNA's of the present invention are known (see Woo et al, et seq) or have been determined as stated above. Knowing the map position of a gene is important and useful if it correlates with a trait, as is the case for the encoded polypeptides of the present invention. Certain alleles of these genes can, for instance, have an impact on seed hardness, starch extractability, energy availability, etc as is described in detail infra. Considerable knowledge has been accumulated regarding the so called Quantitative Trait Loci (QTL). Linkage of a gene to a QTL is of significance regarding the impact of this gene on the corresponding trait. Further, the map position can be used for marker assisted breeding, which is a very economical and time saving way to introduce alleles into elite germplasm. Alternatively, SNP's can also be used to screen a wide variety of germplasm for advantageous alleles.

The 50 kD gamma-zein protein of the present invention displays a high cysteine content and is therefore predicted to have a high number of disulfide bonds or high "disulfide status", as is observed for the other gamma-zein proteins. By "disulfide status" is intended the portion of cysteine residues within a protein that participate in disulfide bonds or disulfide bridges. Such disulfide bonds can be formed between the sulfur of a first cysteine residue and the sulfur of a second cysteine residue. It is recognized that such first and second cysteine residues can occur as part of a single polypeptide chain, or alternatively, can occur on separate polypeptide chains referred to herein as "inter-molecular disulfide bonds". When "disulfide status" is used in reference to a seed or part thereof, the "disulfide status" of such a seed or part thereof is the total disulfide status of the proteins therein.

The disulfide-rich, gamma-zein protein fraction in corn has been implicated as a major determinant of the poor amino acid content of this grain which contributes to its low nutrient content. In addition, as a result of the high-disulfide status of this gamma-zein fraction of corn endosperm it can also be a significant contributor to the wet-milling properties of corn grain. For example, in the wet-milling process, the higher the number of disulfide bonds, the greater the requirement for chemical reductants to break these bonds and to maximize the release of starch granules. It is believed that extensive disulfide bonding negatively impacts the process of wet-milling.

The intermolecular disulfide bridges of the gamma-zeins, along with the hydrophobic beta-zein, and alpha- and delta-zeins, are also important for the formation and maintenance of protein bodies. These protein bodies contribute to the physical properties of the grain that also affect the wet-milling process. In the wet-milling process, chemical reductants are required to break protein disulfide bonds to maximize starch yield and quality (Hoseney, R. C. (1994), Principles of Cereal *Science and Tech.*, (Ed.2)). The use in wet mills of odorous chemical such as sulfur dioxide and bisulfite requires extensive precautions and poses significant environmental problems.

Similar to that described for a decrease in the number of disulfide bonds, a decrease in the number of protein bodies can also be expected to improve the efficiency of the wet-milling process. Zein proteins interact during formation of protein bodies (through intermolecular disulfide bonds and hydropobic interactions), and these interactions are important for the formation of proteolytically stable complexes. Though not limited by any theory of action, a decrease in the expression of two or three gamma-zein genes can be expected to have an additive effect on the reduction of protein bodies resulting in a corresponding improvement in wet-milling properties.

The wet-milling properties of the corn grain of the present invention can be analyzed using a small-scale simulated wet-milling process incorporating or leaving out a reducing agent (bisulfite) in the steep water as used by Eckhoff et al., (1996, *Cereal Chem.* 73:54-57).

In addition to the positive impact that reducing agents have on the release of starch granules in the wet-milling process, it has also been shown that reducing agents can increase the dry matter digestibility of sorghum and corn and, thus, improve their feed properties. This result is supported by the results of data from in vitro digestibility assays described in the present invention (Examples 2-4) that demonstrate that reducing agents increase the dry matter digestibility or energy availability of corn. See also: Hamaker, B. R., et al., 1987, Improving the in vitro protein digestibility of sorghum with reducing agents, *Proc. Natl. Acad. Sci.* USA 84:626-628.

The "energy value", or "caloric value" of a feed or food, which is determined by energy density or gross energy (GE) content and by energy availability, is also termed "metabolizable energy (ME) content." (see Wiseman, J., and Cole, D. J. A., (1987), *Animal Production* 45(1):117-122)

As used herein, "energy availability" means the degree to which energy-rendering nutrients are available to the animal, often referred to as energy conversion (ratio of metabolizable energy content to gross energy content). One way energy availability may be determined is with in vivo balance trials, in which excreta are collected by standard methodology (e.g., Sibbald, I. R., *Poultry Science,* 58(5):1325-29 (1979); McNab and Blair, *British Poultry Science* 29(4):697-708 (1988)). Energy availability is largely determined by food or feed digestibility in the gastro-intestinal tract, although other factors such as absorption and metabolic utilization also influence energy availability.

"Digestibility" is defined herein as the fraction of the feed or food that is not excreted in feces or urine. Digestibility is a component of energy availability. It can be further defined as digestibility of specific constituents (such as carbohydrates or protein) by determining the concentration of these constituents in the foodstuff and in the excreta. Digestibility can be estimated using in vitro assays, which is routinely done to screen large numbers of different food ingredients and plant varieties. In vitro techniques, including assays with rumen inocula and/or enzymes for ruminant livestock (e.g. Pell and Schofield, *Journal of Dairy Science* 76(4):1063-1073 (1993)) and various combinations of enzymes for monogastric animals reviewed in Boisen and Eggum, *Nutrition Research Reviews* 4:141-162 (1991) are also useful techniques for screening transgenic materials for which only limited sample is available.

The enzyme digestible dry matter (EDDM) assay used in these experiments as an indicator of in vivo digestibility is known in the art and can be performed according to the methods described in Boisen and Fernandez (1997) Animal Feed Science and Technology 68:277-286, and Boisen and Fernandez (1995) Animal Feed Science and Technology 51:29-43; which are herein incorporated in their entirety by reference. The actual in vitro method used for determining EDDM in this patent application is a modified version of the above protocol as described in Example 2. These data indicate that reducing the number of disulfide bonds in the seed of sorghum and corn can increase the dry matter digestibility of grain from these crops while retaining a "normal" i.e.: vitreous phenotype. It is also likely that a decrease in the disulfide-status of other grains would have a similar positive effect on their digestibility properties.

While seed with extensive disulfide bonding exhibits poor wet-milling properties and decreased dry matter digestibility, a high disulfide-status has also been correlated with increased seed hardness and improved dry-milling properties. In fact, the transcript level of the 50 kD maize gamma-zein gene has been shown to be largely affected in several opacity mutants (o2, o5, and o9) and in opaque hordothionin-12 (U.S. Pat. No. 5,990,389) corn. These data indicate that this 50 kD maize gamma-zein is a good gene candidate for altering other grain quality traits such as grain hardness. Assays for seed hardness are well known in the art and include such methods as those used in the present invention, described in Pomeranz et al. (1985) Cereal Chemistry 62:108-112; herein incorporated in its entirety by reference.

In another embodiment of the invention, methods are provided for improving maize grain quality by over-expressing the QPM allele to maintain the hard, vitreous kernel phenotype of corn grain while transgenically optimizing the amino acid profile of maize protein. In some instances, the hard, vitreous kernel phenotype and the balance amino acid content traits are dominant or semi-dominant traits. For example, the exemplary QPM allele provides improvements in kernel properties in an alpha-zein suppressed background even if a wild-type allele of the 27 kD gamma-zein gene is present in the genome.

Based on its amino acid sequence, the 18 kD alpha-globulin can also be expected to have a high number of disulfide bonds and to participate in intermolecular protein cross-linking. For this reason, over-expression of the 18 kD alpha-globulin protein can be predicted to increase seed hardness. The ability to confer seed hardness is particularly useful in the case of soft kernel phenotypes that are induced by mutation or transgenic polypeptides. An increase in the levels of the 18 kD alpha-globulin can be used as a method for improving the dry-milling properties of soft kernel phenotypes.

In addition to its high cysteine content, the 18 kD alpha-globulin protein also possesses a relatively high percentage of the essential amino acids tryptophan (4.6% by weight, cysteine (5.1% by weight), and methionine (3.9% by weight). For this reason, transgenic over-expression of the 18 kD alpha-globulin protein can be expected to significantly increase the percentage of tryptophan and sulfur-containing amino acids in corn grain and, thus, increase the nutritional value of the grain.

The "nutritional value" of a feed or food is defined as the ability of that feed or food to provide nutrients to animals or humans. The nutritional value is determined by 3 factors: concentration of nutrients (protein & amino acids, energy, minerals, vitamins, etc.), their physiological availability during the processes of digestion, absorption and metabolism, and the absence (or presence) of anti-nutritional compounds.

Similar to the 18 kD alpha-globulin, the 50 kD legumin 1 protein also possesses a relatively high percentage of essential amino acids. This protein contains 6.7%, 0.7%, 2.2%, 1.1%, 3.6%, and 2.7% by weight of lysine, tryptophan, methionine, cysteine, isoleucine, and threonine, respectively. For this reason, transgenic over-expression of the 50 kD legumin 1 protein can also be expected to increase the nutritional value of the grain.

In addition to its desirable amino acid content, the 50 kD legumin 1 protein is assembled differently than other legumin polypeptides. As a result of the missing downstream proteolytic cleavage sequence (see Yamagata et al., et seq.), the 50 kD legumin 1 protein is not cleaved into acidic and basic chains. Instead this legumin assembles into 9S polypeptide primers (presumably in the endoplasmic reticulum) and does not undergo assembly into 11S globulin hexamers. The assembly properties of this 50 kD legumin 1 polypeptide could contribute to unique food processing properties of protein extracts from seed expressing this protein. For example, the 50 kD legumin 1 polypeptide could be ectopically expressed in soybean seed and protein isolates from corresponding soybean seed display altered functionalities such as solubility under acidic conditions, improved water-holding capacity and the like.

Another feature of the 50 kD legumin 1 polypeptide is a string of histidine residues that can function as a metal binding site. Native 50 kD legumin 1 polypeptide binds with high affinity to nickel chelation columns. This property can be used to purify corn legumin 1 in bulk from complex protein mixtures and to purify other polypeptides of interest through the production of fusion proteins. The metal chelation properties of the 50 kD legumin 1 polypeptide could also be of importance for bio-remediation or food health (antioxidant) applications. Additionally, in cereal grain such as maize or sorghum transgenically overexpressing the 50 kD legumin 1 polypeptide, the Zn and Fe chelating properties of the 50 kD legumin 1 polypeptide may result in an increased concentrations of Zn and Fe in the grain and in increased bio-availability of these micro-nutrient from the diet.

Similar to the over expression of the 18 kD alpha-globulin maize grain, the over-expression of the 50 kD corn legumin 1 protein unexpectedly also resulted in a significant increase of grain digestibility (See Example 11). Endosperm from transgenic corn grain over-expressing corn either alpha-globulin or corn legumin was investigated by immuno-Electron Microscopy (EM). Both transgenic proteins were found to accumulate in non-zein storage organelles, which appear greatly enhanced in number and in size in the transgenic endosperm samples, compared to control EM images obtained from endosperm from non-transgenic corn. Thus the investigation of endosperm structure for similar changes in protein storage organelle number and sizes may be used to select transgenic corn lines transformed with unrelated seed proteins or foreign non-seed protein to screen for events carrying a highly digestible endosperm trait.

It has also been demonstrated that proteolytic digestion of the alcohol-soluble seed protein fraction (prolamins) from wheat, barley, oats, and rye is known to give rise to anti-nutritional peptides able to adversely affect the intestinal mucosa of coeliac patients (Silano and Vincenzi (1999) Nahrung 43:175-184). Furthermore, the alpha-, beta-, and gamma-gliadins present in the prolamin-like protein fraction of wheat are capable of inducing coeliac disease (Friis et al. (1994) Clin. Chim. Acta. 231:173-183). The alpha-gliadin and gamma-gliadin from wheat have also been identified as major allergens (Maruyama et al. (1998) Eur. J. Biochem. 256:604. For these reasons the methods of the present invention are also directed to the elimination or the reduction of the levels of at least one seed protein in wheat, barley, oats, or rye to produce a grain with eliminated or reduced anti-nutritional or allergenic properties.

The compositions and methods of the invention are useful for modulating the levels of at least one seed protein in seeds. By "modulate" is defined herein as an increase or decrease in the level of a seed protein within seed of a genetically altered plant relative to the level of that protein in seed from the corresponding wild-type plant (i.e., a plant not genetically altered in accordance with the methods of the present invention).

The terms "inhibit," "inhibition," "inhibiting", "reduced", "reduction" and the like as used herein refer to any decrease in the expression or function of a target gene product, including any relative decrement in expression or function up to and including complete abrogation of expression or function of the target gene product. The term "expression" as used herein in the context of a gene product refers to the biosynthesis of that gene product, including the transcription and/or translation of the gene product. Inhibition of expression or function of a target gene product (i.e., a gene product of interest) can be in the context of a comparison between any two plants, for example, expression or function of a target gene product in a genetically altered plant versus the expression or function of that target gene product in a corresponding wild-type plant. Alternatively, inhibition of expression or function of the target gene product can be in the context of a comparison between plant cells, organelles, organs, tissues, or plant parts within the same plant or between plants, and includes comparisons between developmental or temporal stages within the same plant or between plants. Any method or composition that down-regulates expression of a target gene product, either at the level of transcription or translation, or down-regulates functional activity of the target gene product can be used to achieve inhibition of expression or function of the target gene product.

The term "inhibitory sequence" encompasses any polynucleotide or polypeptide sequence that is capable of inhibiting the expression of a target gene product, for example, at the level of transcription or translation, or which is capable of inhibiting the function of a target gene product. Examples of inhibitory sequences include, but are not limited to, full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

Inhibitory sequences are designated herein by the name of the target gene product. Thus, for example, an "27 kD gamma zein inhibitory sequence" would refer to an inhibitory sequence that is capable of inhibiting the expression of 27 kD gamma zein, for example, at the level of transcription and/or translation, or which is capable of inhibiting the function of 27 kD gamma zein. When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (i.e., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (i.e., inhibits expression or function of the target gene product).

Conversely, the terms "increase," "increased," and "increasing" in the context of the methods of the present invention refer to any increase in the expression or function of a gene product, including any relative increment in expression or function. As with inhibition, increases in the expression or function of a gene product of interest (i.e., a target gene product) can be in the context of a comparison between any two plants, for example, expression or function of a target gene product in a genetically altered plant versus the expression or function of that target gene product in a corresponding wild-type plant. Alternatively, increases in the expression or function of the target gene product can be in the context of a comparison between plant cells, organelles, organs, tissues, or plant parts within the same plant or between plants, and includes comparisons between developmental or temporal stages within the same plant or between plants. Any method or composition that up-regulates expression of a target gene product, either at the level of transcription or translation, or up-regulates functional activity of the target gene product can be used to achieve increased expression or function of the target gene product. For example, a method that increases oil production in a plant can be any method that increases the total oil content or the percent oil content of that plant relative to that observed in another plant, for example a comparison between a genetically modified plant and a corresponding wild-type plant, any method that increases oil content of a cell, organelle, organ, tissue, or plant part relative to a different cell, organelle, organ, tissue, or plant part within the same plant or between two plants, or any method that increases oil content of a cell, organelle, organ, tissue, plant part, or whole plant relative to that observed during different developmental or temporal stages within the same plant or another plant.

In one embodiment, methods are particularly directed to reducing the level of zein proteins, such as, but not limited to, 16 kD, the 27 kD protein and the 50 kD gamma-zein proteins to improve the nutritional value and industrial use of grain. Another embodiment is directed to the reduction or elimination of the alpha-zein of maize. In another embodiment, the levels of alpha-zeins and of gamma-zeins are reduced in maize grain resulting in an increase in digestibility. Yet another embodiment is directed to the reduction or elimination of the alpha-, beta-, and gamma-gliadins of wheat, barley, rye, and oats to eliminate or ameliorate the anti-nutritional or allergenic effects of these proteins. In another embodiment, the levels of the alpha-globulin protein or the corn legumin 1 protein in plant seed are modulated to affect the nutritional value, or the hardness of the seed. Another embodiment is directed to the reduction of the major zein seed proteins and the concurrent increase of the levels of the alpha-globulin protein or the corn legumin 1 protein to incrementally or synergistically improve the grain digestibility. Other embodiments of the invention include methods directed to screening for particular plant phenotypes based on antibodies specific for the polypeptides of the invention, or using SNP's of the nucleotide sequences of the invention.

Reduction of the level of the 16 kD, the 27 kD protein or the 50 kD gamma-zein proteins in plant seed can be used to improve the nutritional value and industrial use of such grain. The methods of the invention can be useful for producing grain that is more rapidly and extensively digested than grain with normal/wild-type gamma-zein protein levels.

Because the inhibition of the 27 kD gamma-zein trait is dominant or semi-dominant, improvements in grain digestibility can be obtained by introducing it into specific pollinators (i.e., high oil corn) using conventional methods and/or the top-cross technology found in U.S. Pat. No. 5,704,160. In addition, reducing the levels of other seed proteins, such as beta-zein, in conjunction with inhibition of one or more gamma-zein genes can result in further grain improvement including improved digestibility.

Thus, inhibition of gamma-zein genes can be used to increase the nutritional value of seed, particularly by increasing the energy availability of seed. Reduction in the gamma-zein levels in such seed can be at least about 20%, 30%, 40%, 50%, 60%, 70%, 80%, 90% and up to 100%. Energy availability can be improved by at least 3%, 6%, 9%, 12%, 15%, 20% and greater.

Reduction of the level of alpha-zein proteins in plant seed can be used to improve the nutritional value and industrial use of such grain. The methods of the invention are also useful for producing grain that is more rapidly and extensively digested than grain with normal gamma-zein protein levels.

Inhibition of alpha-zein genes can be used to increase the nutritional value of seed, particularly by increasing the energy availability of seed. Reduction in the alpha-zein levels in such seed can be at least about 20%, 30%, 40%, 50%, 60%, 70%, 80%, 90% and up to 100%. Energy availability can be improved by at least 3%, 6%, 9%, 12%, 15%, 20% and greater.

It has been discovered that the improvement in energy availability by inhibition of alpha-zeins is in part independent on the levels of gamma-zein or interaction with gamma-zein proteins. Thus the combined inhibition of alpha-zein and gamma-zein proteins (either in breeding crosses or in independent transgenic events and/or in mutants or by means of stacked transgenic constructs) shows an increase in digestibility greater than inhibition of either alpha-zein or gamma-zein protein alone.

Similarly, the combination of inhibiting either, or both, alpha- or gamma-zein proteins, with over-expressing either, or both, 18 kD alpha-globulin or 50 kD corn legumin 1, leads to an increase in grain digestibility greater than inhibition of alpha- and gamma-zein proteins alone or increasing levels of 18 kD alpha-globulin and/or 50 kD corn legumin 1 alone.

Methods of the invention are also directed to the reduction or elimination of the expression of one or more specific prolamin-like proteins in the grain of wheat, barley, oats, and rye that are known to give rise to anti-nutritional peptides. These proteins include, but are not limited to, the alpha-, beta-, and gamma-gliadins of wheat. Grain and grain products possessing reduced levels of these proteins would not possess such negative characteristics as inducing coeliac disease or stimulating an allergic response.

It is noted that modifications made to the grain by the present invention typically do not compromise grain handling properties with respect to mechanical damage: taking into account that grain handling procedures are adapted to specific properties of the modified grain. Mechanical damage to grain is a well-described phenomenon (e.g., McKenzie, B. A., *Am Soc Ag Engineers* (No: 85-3510): 10 pp, 1985) that contributes to dust in elevators and livestock facilities, and which may increase susceptibility to pests. Grain damage can be quantified and assessed by objective measures (e.g., Gregory, J. M., et al., *Am Soc. Ag. Engineers* (no. 91-1608): 11 pp, 1991) such as kernel density and test weight. See also: McKenzie, B. A. 1985, supra.

The invention also encompasses modulation of an 18 kD alpha-globulin protein or a corn legumin 1 protein to affect the nutritional value and/or the hardness of plant seed. A decrease in or an elimination of the expression of at least one of these proteins results in seed with decreased nutritional value. Such grain has applications for use in diet food products. Alternatively, an increase in the levels of these proteins in plant seed would result in an increase in the nutritional value of the seed. The levels of the maize 18 kD alpha-globulin protein (SEQ ID NO:4) can be increased in maize seed, resulting in seed that can be predicted to possess at least about 20%, 30%, 40%, 50%, 60%, 70%, 80%, 90%, 100%, 110%, 120%, 130%, 140%, 150%, and up to a 300% increase in tryptophan and sulfur-containing amino acids relative to grain of wild-type plants. The level of the corn legumin 1 protein can be similarly increased in maize seed to increase the level of essential amino acids in the grain. Food products and feed based on such seed will have a higher nutritional value based on the increased levels of essential amino acids.

In addition to the increase in nutritional value, an increase in the level of the 18 kD alpha-globulin protein in plant seed can be predicted to result in grain possessing altered hardness. This is due to an increase in non-zein protein accumulated in non-zein storage organelles relative to grain from wild-type plants, and has applications for improving the dry-milling properties of such modified grain. Introduction of this trait into corn plants with inferior kernel phenotypes, particularly inferior kernel phenotypes induced by the introduction of other transgenic polypeptides including, but not limited to, hordothionin 12 (U.S. Pat. No. 5,990,389), can ameliorate or eliminate the undesirable dry-milling properties of such grain by altering seed hardness.

In another embodiment, the levels of the 50 kD legumin 1 polypeptide are increased in cereal grain for the purpose of increasing the metal chelating properties of the grain. The unique string of histidine residues present in the 50 kD legumin 1 polypeptide function as a metal chelating site. Products produced from such grain could be used for bio-remediation, in food health (antioxidant) applications, or in biofortification (increase of zinc and iron bioavailability).

Methods are provided for modulating the level of at least one seed protein in plant seed including, but not limited to, seed proteins such as: zeins, such as the 50 kD gamma-zein (SEQ ID NO:2),), the 27 kD gamma-zein (Accession No. P04706), the 16 kD gamma-zein (Accession No. AAA33523), the 15 kD beta-zein (Accession No. P06673) the delta zeins (Woo, et al) the alpha-zeins (Song et al, 2002, 2001), and the like, globulins, such as the 18 kD alpha-globulin (SEQ ID NO:4), legumins such as the corn legumin 1 (SEQ ID NO:6), the kafarins, the alpha-, beta-, and gamma-gliadins and the like.

While not critical to the invention, the methods of the invention comprise either increasing or decreasing the level of a target gene product. Methods for inhibiting gene expression are well known in the art. Although any method know in the art for reducing the level of protein in a plant could be used, possible methods for reducing protein include, but are not limited to, homology-dependent gene silencing, antisense technology, co-suppression including, for example, RNA interference (RNAi), micro RNA and the like, site-specific recombination, site-specific integration, mutagenesis including transposon tagging, and biosynthetic competition, homologous recombination, and gene targeting, alone or in combination. Depending upon the intended goal, the level of at least one seed protein may be increased, decreased, or eliminated entirely as described below.

Methods of the invention can be utilized to alter the level of any seed protein found within a particular plant species, including but not limited to, the alpha-, beta-, delta-, gamma-zeins of maize, and alpha-globulins of maize, the legumin 1 and other seed proteins of maize, rice and sorghum, and the alpha-, beta-, and gamma-gliadins of wheat, barley, rye, and oats.

In many instances the nucleotide sequences for use in the methods of the present invention, are provided in transcriptional units with for transcription in the plant of interest. A transcriptional unit is comprised generally of a promoter and a nucleotide sequence operably linked in the 3' direction of the promoter, optionally with a terminator.

By "operably linked" is intended a functional linkage between a promoter and a second sequence, wherein the promoter sequence initiates and mediates transcription of the DNA sequence corresponding to the second sequence. The expression cassette will include 5' and 3' regulatory sequences operably linked to at least one of the sequences of the invention.

Generally, in the context of an over expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The methods of transgenic expression can be used to increase the level of at least one seed protein in grain. The methods of transgenic expression comprise transforming a plant cell with at least one expression cassette comprising a promoter that drives expression in the plant operably linked to at least one nucleotide sequence encoding a seed protein. Methods for expressing transgenic genes in plants are well known in the art.

In other instances the nucleotide sequences for use in the methods of the invention are provided in transcriptional units as co-supression cassettes for transcription in the plant of interest. Transcription units can contain coding and/or non-coding regions of the genes of interest. Additionally, transcription units can contain promoter sequences with or without coding or non-coding regions. The co-suppression cassette may include 5' (but not necessarily 3') regulatory sequences, operably linked to at least one of the sequences of the invention. Co-supression cassettes used in the methods of the invention can comprise sequences of the invention in so-called "inverted repeat" structures. The cassette may additionally contain a second copy of the fragment in opposite direction to form an inverted repeat structure: opposing arms of the structure may or may not be interrupted by any nucleotide sequence related or unrelated to the nucleotide sequences of the invention. (see Fiers et al. U.S. Pat. No. 6,506,559). The transcriptional units are linked to be co-transformed into the organism. Alternatively, additional transcriptional units can be provided on multiple over-expression and co-suppression cassettes.

The methods of transgenic co-suppression can be used to reduce or eliminate the level of at least one seed protein in grain. One method of transgenic co-suppression comprise transforming a plant cell with at least one transcriptional unit containing an expression cassette comprising a promoter that drives transcription in the plant operably linked to at least one nucleotide sequence transcript in the sense orientation encoding at least a portion of the seed protein of interest. Methods for suppressing gene expression in plants using nucleotide sequences in the sense orientation are known in the art. The methods generally involve transforming plants with a DNA construct comprising a promoter that drives transcription in a plant operably linked to at least a portion of a nucleotide sequence that corresponds to the transcript of the endogenous gene. Typically, such a nucleotide sequence has substantial sequence identity to the sequence of the transcript of the endogenous gene, at least about 65%, 70%, 75%, 80%, 85%, 90%, 91%, 92%, 93%, 94%, 95%, 96%, 97%, 98%, or 99% or more sequence identity over the entire length of the sequence. Furthermore, portions, rather than the entire nucleotide sequence, of the polynucleotides may be used to disrupt the expression of the target gene product. Generally, sequences of at least 10, 15, 20, 21, 22, 23, 24, 25, 26, 27, 28, 29, 30, 35, 40, 45, 50, 55, 60, 65, 70, 75, 80, 85, 90, 95, 100, 200 nucleotides, or greater may be used. See U.S. Pat. Nos. 5,283,184 and 5,034,323; herein incorporated by reference.

The endogenous gene targeted for co-suppression may be a gene encoding any seed protein that accumulates as a seed protein in the plant species of interest, including, but not limited to, the seed genes noted above. For example, where the endogenous gene targeted for co-suppression is the 50 kD gamma-zein gene disclosed herein, co-suppression is achieved using an expression cassette comprising the 50 kD gamma-zein gene sequence, or variant or fragment thereof.

Additional methods of co-suppression are known in the art and can be similarly applied to the instant invention. These methods involve the silencing of a targeted gene by spliced hairpin RNA's and similar methods also called RNA interference and promoter silencing (see Smith et al. (2000) Nature 407:319-320, Waterhouse and Helliwell (2003)) Nat. Rev. Genet. 4:29-38; Waterhouse et al. (1998) Proc. Natl. Acad. Sci. USA 95:13959-13964; Chuang and Meyerowitz (2000) Proc. Natl. Acad. Sci. USA 97:4985-4990; Stoutjesdijk et al. (2002) Plant Phystiol. 129:1723-1731; and Patent Application WO 99/53050; WO 99/49029; WO 99/61631; WO 00/49035 and U.S. Pat. No. 6,506,559, each of which is herein incorporated by reference). For the purpose of this invention the term "co-suppression" is used to collectively designate gene silencing methods based on mechanisms involving the expression of sense RNA molecules, aberrant RNA molecules, double-stranded RNA molecules, micro RNA molecules and the like.

The expression cassette for co-suppression may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, International Publication No. WO 02/00904, herein incorporated by reference. In other embodiments of the invention, inhibition of the expression of a protein of interest may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants.

In one embodiment, the polynucleotide to be introduced into the plant comprises an inhibitory sequence that encodes a zinc finger protein that binds to a gene encoding a protein of the invention resulting in reduced expression of the gene. In particular embodiments, the zinc finger protein binds to a regulatory region of a zein gene, a legumin gene or a globulin gene. In other embodiments, the zinc finger protein binds to a messenger RNA encoding a seed protein and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 20030037355; each of which is herein incorporated by reference.

Methods for antisense suppression can be used to reduce or eliminate the level of at least one seed protein in grain. The methods of antisense suppression comprise transforming a plant cell with at least one expression cassette comprising a promoter that drives expression in the plant cell operably linked to at least one nucleotide sequence that is antisense to a nucleotide sequence transcript of such a gamma-zein gene. By "antisense suppression" is intended the use of nucleotide sequences that are antisense to nucleotide sequence transcripts of endogenous plant genes to suppress the expression of those genes in the plant.

Methods for suppressing gene expression in plants using nucleotide sequences in the antisense orientation are known in the art. The methods generally involve transforming plants with a DNA construct comprising a promoter that drives expression in a plant operably linked to at least a portion of a nucleotide sequence that is antisense to the transcript of the endogenous gene. Antisense nucleotides are constructed to hybridize with the corresponding mRNA. Modifications of the antisense sequences may be made as long as the sequences hybridize to and interfere with expression of the corresponding mRNA. In this manner, antisense constructions having at least about 70%, 75%, 80%, 85%, 90%, 91%, 92%, 93%, 94%, 95%, 96%, 97%, 98%, or 99% or more sequence identity to the corresponding antisense sequences may be used. Furthermore, portions, rather than the entire nucleotide sequence, of the antisense nucleotides may be used to disrupt the expression of the target gene. Generally, sequences of at least 10 nucleotides, 50 nucleotides, 100 nucleotides, 200 nucleotides, or greater may be used.

Methods for transposon tagging can be used to reduce or eliminate the level of at least one seed protein in grain. The methods of transposon tagging comprise insertion of a transposon within an endogenous plant seed gene to reduce or eliminate expression of the seed protein.

Methods for transposon tagging of specific genes in plants are well known in the art (see for example, Maes et al. (1999) Trends Plant Sci. 4:90-96; Dharmapuri and Sonti (1999) FEMS Microbiol. Lett. 179:53-59; Meissner et al. (2000) Plant J. 22:265-274; Phogat et al. (2000) J. Biosci. 25:57-63; Walbot (2000) Curr. Opin. Plant Biol. 2:103-107; Gai et al. (2000) Nuc. Acids Res. 28:94-96; Fitzmaurice et al. (1999) Genetics 153:1919-1928). In addition, the TUSC process for selecting Mu-insertions in selected genes has been described (Bensen et al. (1995) Plant Cell 7:75-84; Mena et al. (1996) Science 274:1537-1540; U.S. Pat. No. 5,962,764, which is herein incorporated by reference).

Other methods for inhibiting or eliminating the expression of endogenous genes are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted (for examples of these methods see Ohshima et al. (1998) Virology 243:472-481; Okubara et al. (1994) Genetics 137:867-874; Quesada et al. (2000) Genetics 154:421-436. In addition, a fast and automatable method for screening for chemically induced mutations, TILLING, (Targeting Induced Local Lesions In Genomes), using a denaturing HPLC or selective endonuclease digestion of selected PCR products is also applicable to the instant invention (see McCallum et al. (2000) Nat. Biotechnol. 18:455-457).

Mutation breeding is another of many methods that could be used to introduce new traits into an elite line. Mutations that occur spontaneously or are artificially induced can be useful sources of variability for a plant breeder. The goal of induced mutagenesis is to increase the rate of mutation for a desired characteristic. Mutation rates can be increased b many different means including: temperature; long-term seed storage; tissue culture conditions; radiation such as X-rays, Gamma rays (e.g., Cobalt 60 or Cesium 137), neutrons, (product of nuclear fission by Uranium 235 in an atomic reactor, Beta radiation (emitted from radioisotopes such as P32, or C14), or ultraviolet radiation (preferably from 2500 to 2900 nm); or chemical mutagens such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis, the trait may then be incorporated into existing germplasm by traditional breeding techniques, such as backcrossing. Details of mutation breeding can be found in "Principals of Cultivar Development" Fehr, 1993 (Macmillan Publishing Company), the disclosures of which are incorporated herein by reference. In addition, mutations created in other lines may be used to produce a backcross conversion of elite lines that comprise such mutations.

Other methods for inhibiting or eliminating the expression of genes include the transgenic application of transcription factors (Pabo, C. O., et al. (2001) Annu Rev Biochem 70, 313-40; and Reynolds, L., et al (2003), Proc Natl Acad Sci USA 100, 1615-20.), and homologous recombination methods for gene targeting (see U.S. Pat. No. 6,187,994).

Similarly, it is possible to eliminate the expression of a single gene by replacing its coding sequence with the coding sequence of a second gene using homologous recombination technologies (see Bolon, B. Basic Clin. Pharmacol. Toxicol. 95:4, 12,154-61 (2004); Matsuda and Alba, A., Methods Mol. Bio. 259:379-90 (2004); Forlino, et. al., J. Biol. Chem. 274: 53, 37923-30 (1999)). For example, by using the knock-out/knock-in technology, the coding sequence of the 27 kD gamma-zein protein can be replaced by the coding sequence of the 18 kD alpha-globulin resulting in suppression of 27 kD gamma-zein protein expression and in over-expression of the alpha-globulin protein.

In some embodiments, the polynucleotide expressed by the expression cassette of the invention is catalytic RNA or has ribozyme activity specific for the messenger RNA of a protein of interest. Thus, the polynucleotide causes the degradation of the endogenous messenger RNA, resulting in reduced expression of one or more proteins. This method is described, for example, in U.S. Pat. No. 4,987,071, herein incorporated by reference.

In some embodiments of the invention, the polynucleotide comprises an inhibitory sequence that encodes an antibody that binds to at least one isoform of a seed protein, and reduces the level of the seed protein. In another embodiment, the binding of the antibody results in increased turnover of the antibody-antigen complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

Methods of biosynthetic competition with other high-sulfur-containing proteins are used to reduce the levels of at least one seed protein in plant seed. The methods of biosynthetic competition comprise transforming plant cells with at least one expression cassette comprising a promoter that drives expression in the plant cell operably linked to at least one nucleotide sequence encoding a protein selected from the group consisting of delta-zeins, hordothionin 12, and other naturally occurring or engineered high-sulfur-containing proteins. In some cases the competing protein may possess a high lysine content in addition to a high sulfur content to further increase the nutritional value of the grain.

Biosynthetic competition of seed proteins with other sulfur-rich proteins occurs naturally. This natural process can be manipulated to reduce the levels of certain seed proteins, because the synthesis of some seed proteins is transcriptionally and/or translationally controlled by the nitrogen and/or sulfur supply in the developing seed. The expression of recombinant polypeptides, including the ectopic (transgenic) expression of seed proteins or other high-sulfur-, high-nitrogen-containing proteins, can have a substantial impact on intracellular nitrogen and sulfur pools. Thus, the expression of these proteins can result in suppression of the expression of other seed proteins such as, for example, the high-sulfur containing gamma-zein proteins.

Plant transformants containing a desired genetic modification as a result of any of the above described methods resulting in increased, decreased or eliminated expression of the seed protein of the invention can be selected by various methods known in the art. These methods include, but are not limited to, methods such as SDS-PAGE analysis, immunoblotting using antibodies which bind to the seed protein of interest, single nucleotide polymorphism (SNP) analysis, or assaying for the products of a reporter or marker gene, and the like.

Another embodiment is directed to the screening of transgenic maize plants for specific phenotypic traits conferred by the expression, or lack thereof, of known corn seed proteins and the 50 kD gamma-zein, the 18 kD alpha-globulin, or the 50 kD legumin 1 polypeptides of the invention. The specific phenotypic traits for which this method finds use include, but are not limited to, all of those traits listed herein. Maize lines can be screened for a particular phenotypic trait conferred by the presence or absence of known corn seed proteins and the 50 kD gamma-zein, the 18 kD alpha-globulin, or the 50 kD legumin 1 protein using an antibody that binds selectively to one of these polypeptides. In this method, tissue from the maize line of interest is contacted with an antibody that selectively binds the seed-protein polypeptide for which the screen is designed. The development and use of antibodies for the detection of know corn seed proteins and of the 50 kD gamma-zein, the 18 kD alpha-globulin, or the 50 kD legumin 1 proteins is described in Woo, et al, et seq. The amount of antibody binding is then quantified and is a measure of the amount of the seed-protein polypeptide present in the maize line. Methods of quantifying polypeptides by immunodetection in this manner are well known in the art.

An additional embodiment is directed to the use of the 50 kD legumin 1 protein to purify a polypeptide of interest based on the metal chelating properties of the 50 kD legumin 1 polypeptide. In this case recombinant DNA techniques known in the can be used to produce an expression cassette encoding a heterologous polypeptide consisting of the 50 kD legumin 1 polypeptide or a fragment thereof fused to a polypeptide of interest. The expression cassette can be introduced into either a eucaryotic or a bacterial host cell and the protein expressed in the host cell. The protein can then be isolated from the cells by an appropriate purification scheme using standard metal chelating column techniques such as high affinity nickel chelating columns that are commercially available. The legumin 1 nucleotide sequence can be fused to either the N-terminus or C-terminus of the nucleotide sequence encoding the polypeptide of interest.

In the practice of certain specific embodiments of the present invention, a plant is genetically altered to have a suppressed or increased level of one or more seed proteins in seed and/or to ectopically express one or more seed or other high-sulfur, high-lysine-containing protein. Those of ordinary skill in the art realize that this can be accomplished in any one of a number of ways. For example, each of the respective coding sequences for such proteins can be operably linked to a promoter and then joined together in a single continuous fragment of DNA comprising a multigenic expression cassette. Such a multigenic expression cassette can be used to transform a plant to produce the desired outcome utilizing any of the methods of the invention including sense and antisense suppression and biosynthetic competition. Alternatively, separate plants can be transformed with expression cassettes containing one of the desired set of coding sequences. Transgenic plants resulting from any or a combination of methods including any method to modulate protein levels, can be selected by standard methods available in the art. These methods include, but are not limited to, methods such as immunoblotting using antibodies which bind to the proteins of interest, SNP analysis, or assaying for the products of a reporter or marker gene, and the like. Then, all of the desired coding sequences and/or transposon tagged sequences can be brought together into a single plant through one or more rounds of cross pollination utilizing the previously selected transformed plants as parents.

The nucleotide sequences for use in the methods of the present invention are provided in expression cassettes for transcription in the plant of interest. Such expression cassettes are provided with a plurality of restriction sites for insertion of the 50 kD gamma-zein, the 18 kD alpha-globulin, the 50 kD legumin 1 sequence or any other sequence of the present invention to be placed under the transcriptional regulation of the regulatory regions. The expression cassettes may additionally contain selectable marker genes.

The expression cassette can include in the 5'-3' direction of transcription, a transcriptional and translational initiation region, any seed protein sequence of the invention, and optionally, a transcriptional and translational termination region functional in plants. The transcriptional initiation region, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a gene comprises a coding sequence operably linked to a transcription initiation region that is heterologous to the coding sequence. Alternatively, a gene comprises fragments of at least two independent transcripts that are linked in a single transcription unit.

While it may be preferable to express the sequences using heterologous promoters, the native promoter sequences may be used. Such constructs would alter expression levels of the proteins in the plant or plant cell. Thus, the phenotype of the plant or plant cell is altered. Alternatively, the promoter sequence may be used to alter expression. For example, the promoter (or fragments thereof) of 27 kD gamma-zein can modulate expression of the native 27 kD gamma-zein protein or other closely related proteins.

Use of a termination region is not necessary for proper transcription of plant genes but may be used as part of an expression construct. The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

Where appropriate, for example, as in the case of engineered high-sulfur-containing proteins for the method of biosynthetic competition, the gene(s) may be optimized for increased expression in the transformed plant. That is, the genes can be synthesized using plant-preferred codons for improved expression. See, for example, Campbell and Gowri (1990) Plant Physiol. 92:1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschlei et al. (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Bairn et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

The above list of selectable marker genes is not meant to be limiting. Any selectable marker gene can be used in the present invention.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96:8774-8778; herein incorporated by reference.

A number of promoters can be used in the practice of the invention. The promoters can be selected based on the desired outcome. The nucleic acids can be combined with constitutive, tissue-preferred, or other promoters for expression in plants, more preferably a promoter functional during seed development.

Such constitutive promoters include, for example, the core promoter of the Rsyn7 promoter and other constitutive promoters disclosed in WO 99/43838; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible and tetracycline-repressible promoters (see, for example, Gatz et al. (1991) Mol. Gen. Genet. 227:229-237, and U.S. Pat. Nos. 5,814,618 and 5,789,156), herein incorporated by reference.

Tissue-preferred promoters can be utilized to target enhanced protein expression within a particular plant tissue. Tissue-preferred promoters include, but are not limited to: Yamamoto et al. (1997) Plant J. 12(2)255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kD zein); and milps (myo-inositol-1-phosphate synthase; see U.S. Pat. No 6,225,529 herein incorporated by reference). The 27 kD gamma-zein is a preferred endosperm-specific promoter. Glb-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kD zein, 22 kD zein, 27 kD zein, 10 kD delta-zein, waxy, shrunken 1, shrunken 2, globulin 1, etc.

In certain embodiments the nucleic acid sequences of the present invention can be combined with any combination of polynucleotide sequences of interest or mutations in order to create plants with a desired phenotype. For example, the polynucleotides of the present invention can be combined with any other polynucleotides of the present invention, such as any combination of SEQ ID NOS: 1, 3, 5, or with other seed storage protein genes or variants or fragments thereof such as: zeins, fatty acid desaturases, lysine ketoglutarate, lec1, or Agp. The combinations generated can also include multiple copies of any one of the polynucleotides of interest. The polynucleotides or mutations of the present invention can also be combined with any other gene or combination of genes to produce plants with a variety of desired trait combinations including, but not limited to, traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; 5,703,409 and 6,800,726); high lysine (Williamson et al. (1987) Eur. J. Biochem. 165:99-106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12: 123)); and thioredoxins (U.S. application Ser. No. 10/005, 429, filed Dec. 3, 2001)), the disclosures of which are herein incorporated by reference. The polynucleotides of the present invention can also be combined with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al. (1986) Gene 48:109); lectins (Van Damme et al. (1994) Plant Mol. Biol. 24:825); fumonisin detoxification genes (U.S. Pat. No. 5,792, 931); avirulence and disease resistance genes (Jones et al. (1994) *Science* 266:789; Martin et al. (1993) Science 262: 1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)), the disclosures of which are herein incorporated by reference. One could also combine the polynucleotides or mutations of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These combinations can be created by any method including, but not limited to, cross breeding plants by any conventional or TopCross methodology, by homologous recombination, site specific recombination, or other genetic modification. If the traits are combined by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. Traits may also be combined by transformation and mutation by any known method.

Methods of the invention can be utilized to alter the level of at lease one seed protein in seed from any plant species of interest. Plants of particular interest include grain plants that provide seeds of interest including grain seeds such as corn, wheat, barley, rice, sorghum, rye, oats, etc. The present invention may be used for many plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), oats, and barley.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include, but are not limited to: microinjection (Crossway et al. (1986) Biotechniques 4:320-334), electroporation (Riggs et al. (1986) Proc. Natl. Acad. Sci. USA 83:5602-5606, *Agrobacterium*-mediated transformation (Townsend et al., U.S. Pat. No. 5,563,055; Zhao et al., U.S. Pat. No. 5,981,840; Cai et al., U.S. patent application Ser. No. 09/056,418), direct gene transfer (Paszkowski et al. (1984) EMBO J. 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923-926). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bowen et al., U.S. Pat. No. 5,736,369 (cereals); Bytebier et al. (1987) Proc. Natl. Acad. Sci. USA 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via *Agrobacterium tumefaciens*); all of which are herein incorporated by reference.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the protein of interest of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways, under plant forming conditions. See, for example, McCormick et al. (1986) Plant Cell Reports 5:81-84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

In addition, the desired genetically altered trait can be bred into other plant lines possessing desirable agronomic characteristics using conventional breeding methods (see Example 3) and/or top-cross technology. The top-cross method is taught in U.S. Pat. No. 5,704,160 herein incorporated in its entirety by reference.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of heterologous coding sequences of the two parental plants can be selected from all of the progeny by standard methods available in the art as described infra for selecting transformed plants. If necessary, the selected progeny can be used as either the pollen donor or pollen recipient in a subsequent cross pollination.

It has been shown that the response in digestibility to the treatment of grain with DTT is inversely related to the digestibility of untreated grain (Boisen and Eggum, Nutrition Research Reviews 4:141-162 (1991)).

Digestibility of immature grain (grain at late dough or silage maturity stage) is equally improved by pretreatment with reducing agents (DTT) as mature grain. The same can be expected for low gamma-zein corn as the effects of DTT pretreatment, and low gamma-zein corn, on digestibility are virtually the same. Improvements in digestibility of immature grain through the methods of the present invention can be extrapolated to improvements in digestibility of silage—about half of which consists of immature grain. The improvements in digestibility with DTT pretreatment is inversely related to the intrinsic digestibility of untreated grain. For this reason, corn lines of low intrinsic digestibility can be expected to be more amenable to genetic modification through the method of the invention than those of higher digestibility. This aspect of the invention enables those of skill in the art of breeding to make rapid advances in introgressing a low gamma-zein trait into the appropriate elite germplasm.

This invention allows for the improvement of grain properties such as increased digestibility/nutrient availability, nutritional value, silage quality, and efficiency of wet or dry milling in maize strains already possessing other desirable characteristics.

Corn grain with reduced gamma-zein protein content offers the following advantages:

First, ground corn grain with a reduced gamma-zein protein content offer increased energy availability and protein digestibility to monogastric livestock (see Example 2). "Monogastric animals" include but are not limited to: pigs, poultry, horses, dogs, cats, rabbits and rodents.

It can be deduced from analysis of the in vitro experimental data provided herein that the corn grain from maize genetically altered to contain reduced gamma-zein protein levels will have a 5% increase in metabolizable energy for poultry and pigs. Using this assumption the following replacement value can be assigned to the high energy availability trait in grain resulting from the reduction of gamma-zein protein. Five percent of 1665 kcal/lb equals about 83 kcal/lb. Taking into account that a bushel of corn contains 56-60 lbs, the 83 kcal/lb difference amounts to a gain of 4650-5000 kcal/bu. This difference in available energy is equivalent to 1.3-1.4 lb fat, which, at 12 cts/lb, is worth 15-17 cents per bushel.

Second, corn grain with a reduced gamma-zein protein content possess improved ruminant (e.g.: cattle sheep, and goats) feed quality through increased digestibility (see Example 2). Grain is fed to ruminants in minimally processed form, and the rigid protein structure of corn endosperm has been shown to constitute a large impediment to microbial digestion in the rumen, which can be partly overcome by predigestion with protease (McAllister et al. (1993) J. Anim. Sci. 71:205-212). A reduced gamma-zein protein content imparts a similar or even larger improvement to ruminal digestion of whole corn.

Third, corn grain with reduced levels of gamma-zein proteins has an increased response to feed processing. The nutrient availability from whole corn grain can be increased by extensive processing (steam-flaking or extrusion) resulting in starch gelatinization and protein disulfide bond reduction (Blackwood and Richardson, 1994). The response to processing is sometimes lower than expected. The heat and/or shearing force applied during processing causes rearrangements of protein disulfide bonds, which may partly counteract the improvement in digestibility resulting from starch gelatinization. The response to steam-flaking of corn and sorghum grain is negatively correlated with protein disulfide content (Blackwood and Richardson, 1994). For low gamma-zein corn or low kafarin sorghum the extent of disulfide rearrangements during processing is reduced, which allows for a more uniform response to steam-flaking, and which can be expected to reduce the energy required in steam-flaking or grinding processes.

Fourth, corn grain with a lower gamma-zein protein content has improved silage quality for dairy cattle, especially for silage harvested at late maturity. Although silage is harvested at earlier maturity than grain, a certain degree of dry-down (and protein disulfide formation) has already occurred by the time the crop is ensiled, especially under dry and hot conditions. Our work has shown that pretreatment with a reducing agent of immature, dough-stage corn kernels, sampled at silage maturity, resulted in drastically improved in vitro digestibility, a strong indication that the protein disulfide imposed barriers to digestion had already been established. (data in Example 2). Hence, the digestibility of the "yellow portion" of corn silage can be expected to be higher for grain with a reduced gamma-zein protein content. Increased digestibility will be especially notable in the case of silage made from mature corn and for high-yielding dairy cows in which high passage rates do not allow for extensive ruminal digestion.

Fifth, corn grain with a reduced gamma-zein protein content will have an increased efficiency of wet milling. An increase in wet-milling efficiency and starch recovery can be expected due to the lower disulfide content of grain with reduced gamma-zein protein content. Efficiencies in the processes of wet milling also include reduced steeping time and/or reduced need for chemical reductants such as sulfur dioxide and sodium bisulfite. The use of fewer chemicals will improve wet-milling economics and reduce environmental pollution.

| Table of Sequence ID Nos. | | |
|---|---|---|
| SEQ ID NO: | Gene Name | Amino Acid/Nucleotide |
| 1 | 50 kD gamma-zein | Nucleotide |
| 2 | 50 kD gamma-zein | Amino Acid |
| 3 | 18 kD alpha-globulin | Nucleotide |
| 4 | 18 kD alpha-globulin | Amino Acid |
| 5 | 50 kD corn legumin1 | Nucleotide |
| 6 | 50 kD corn legumin1 | Amino Acid |
| 7 | 50 kD gamma-zein, B73 | Nucleotide |
| 8 | 50 kD gamma-zein, Mo17 | Nucleotide |
| 9 | 18 kD alpha-globulin, B73 | Nucleotide |

Table of Sequence ID Nos.

| SEQ ID NO: | Gene Name | Amino Acid/Nucleotide |
|---|---|---|
| 10 | 18 kD alpha-globulin, Mo17 | Nucleotide |
| 11 | TUSC primer 170 | Nucleotide |
| 12 | TUSC primer 296 | Nucleotide |
| 13 | MU primer 9242 | Nucleotide |
| 14 | TUSC primer 008 | Nucleotide |
| 15 | TUSC primer 009 | Nucleotide |
| 16 | Chimeric alpha-zein | Nucleotide |
| 17 | Chimeric silencing seq. | Nucleotide |
| 18 | 15 kD beta-zein | Nucleotide |
| 19 | 15 kD beta-zein | Amino Acid |
| 20 | High sulfur zein | Nucleotide |
| 21 | High sulfur zein | Amino Acid |
| 22 | Sorghum legumin1 | Nucleotide |
| 23 | Sorghum legumin1 | Amino Acid |
| 24 | Sugarcane legumin1 | Nucleotide |
| 25 | Sugarcane legumin1 | Amino Acid |
| 26 | GZ-W64A promoter | Nucleotide |
| 27 | GZ-W64A terminator | Nucleotide |
| 28 | QPM allele | Nucleotide |
| 29 | QPM allele | Amino Acid |
| 30 | 27 kD gamma-zein, wild type | Nucleotide |
| 31 | 27 kD gamma-zein, wild type | Amino Acid |
| 32 | 27 kD gamma-zein, deletion | Nucleotide |

EXAMPLES

Maize lines (transgenic and transposon-mutagenized) have been developed with increased or decreased levels of specific endosperm proteins. For several of the obtained lines, experimental evidence indicates that the introduced changes result in improved grain properties.

Example 1

Cloning and Transgenic Co-Suppression of a Novel Maize 50 kD Gamma-Zein

A 50 kD gamma-zein nucleotide sequence was cloned from a maize endosperm cDNA library (mid and late development). Based on EST numbers 50 kD gamma-zein transcripts are relatively abundant (compared to other seed protein transcripts) and represent approximately 0.5% of the endosperm mRNA during mid development. A large variation in the abundance of 50 kD gamma-zein transcripts has been observed between different inbred lines (transcript profiling results). The 50 kD gamma-zein gene has been located on chromosome 7, bin 7.03

The 50 kD gamma-zein cDNA sequences isolated from different inbred lines show an unusually low level of polymorphism. Only one SNP (a 3 bp insertion) was detected along the entire cDNA sequence from DNA isolated from the inbred lines Mo17 and B73 (the SNP is bold and in lower case). See also SEQ ID NOS: 7 and 8.

```
50 kD gamma-zein, B73 partial
CCAGCAGCAGCAACACCAACAACAACAAGTTCACATGCAACCACAAAAAC

ATCAGCAACAACAAGAAGTTCATGTTCAACAACAACAACAACAACCGCAG

CACCAACAACAACAACAACAACAacaGCACCAACAACAACATCAATGTGA

AGGCCAACAACAACATCACCAACAATCACAAGGCCATGTGCAACAACACG

AACAGAGCCATGAGCAACACCAAGGACAGAGCCATGAGCAACAACATCAA

CAACAATTCCAGGGTCATGACAAGCAGCAACAACCACAACAGCCTCAGCA

ATATCAGCAGGGCCAGGAAAAATC 50 kD gamma-zein, Mo17 partial
CCAGCAGCAGCAACACCAACAACAACAAGTTCACATGCAACCACAAAAAC

ATCAGCAACAACAAGAAGTTCATGTTCAACAACAACAACAACAACCGCAG

CACCAACAACAACAACAACAACA***GCACCAACAACAACATCAATGTGA

AGGCCAACAACAACATCACCAACAATCACAAGGCCATGTGCAACAACACG

AACAGAGCCATGAGCAACACCAAGGACAGAGCCATGAGCAACAACATCAA

CAACAATTCCAGGGTCATGACAAGCAGCAACAACCACAACAGCCTCAGCA

ATATCAGCAGGGCCAGGAAAAATC
```

The 50-kD gamma-zein transformation event described herein was one of various high-digestibility events produced. The event was generated with a construct containing the 27 kD gamma-zein promoter, 50 kD gamma-zein ORF in sense orientation, and 27-kD gamma zein terminator using particle bombardment. It was found to be reduced in all known gamma zein proteins, i.e., 50 kD-, 27 kD-, and 16 kD gamma-zein. Protein gel & 50 kD gamma-zein Western blots of segregating CS50 events were performed to confirm co-suppression. The kernel phenotype of the transgenic seed was normal (i.e., vitreous).

Segregating kernels from transgenic corn co-suppressed in 50 kD gamma-zein were ground to a fine meal and subjected to the monogastric in vitro digestibility assay as described in Example 2 to determine Enzyme Digestible Dry Matter (EDDM). EDDM of 50 kD gamma-zein co-suppressed grain was improved by 3.0 percentage units. An overnight soak in 10 mM of the strong reducing agent dithiothreietol (DTT), known to maximize in vitro digestibility, improved digestibility slightly beyond that reached with 50 kD gamma-zein co-suppression (by 1.4 percentage units).

Example 2

In Vitro Enzyme Digestible Dry Matter (EDDM) Assay

Corn grain was ground in a micro Wiley Mill (Thomas Scientific, Swedesboro, N.J.) through a 1 mm screen; 0.5 g of ground corn sample was placed in a pre-weighed nylon bag (50 micron pore size) and heat sealed. Approximately 40 bags were placed in an incubation bottle with 2 L of 0.2M phosphate buffer (pH 2.0) containing pepsin (0.25 mg/ml). Samples were incubated in a Daisy II incubator (ANKOM Technology, Fairport, N.Y.) at 39° C. for 2 hours. After 2 hours, samples were placed in a mesh bag and washed for 2 minutes with cold water in a washer (Whirlpool) using delicate cycle. Samples were then transferred into 2 L of 0.2M phosphate buffer (pH 6.8) containing pancreatin (5.0 mg/ml) and incubated at 39° C. for 4 or 6 hours. Samples were washed for 2 minutes as described earlier. Samples were then dried overnight at 55° C. and weighed. The difference in sample weight before and after incubation was expressed as percentage of enzyme digestible dry matter digestibility (EDDM). EDDM data generated by in vitro digestibility assay could vary with genetic backgrounds, field conditions and locations in which the plants are grown. Hence the absolute EDDM values could vary for the same transgene with different genetic backgrounds, field conditions and locations in which they are grown.

Example 3

Transgenic Co-Suppression of 27 kD Gamma-Zein

Events in which the expression level of 27 kD gamma-zein protein was reduced to less than 5% of wild-type as determined by SDS-PAGE and immunoblotting were obtained with three different transgenic constructs.

One event was generated with a construct containing the 27 kD gamma-zein promoter, 27 kD gamma-zein ORF in sense orientation (GenBank Accession No: AF371261), and the 27-kD gamma-zein terminator using *Agrobacterium*-mediated transformation (see Example 12). It was found to be reduced in 27 kD-, and 16 kD-gamma-zein. The kernel phenotype of the transgenic seed was normal (i.e., vitreous).

A second event was generated with a construct containing the CZ19B1 promoter (U.S. Pat. No. 6,225,529), 27 kD gamma-zein ORF in sense orientation, and the 27-kD gamma-zein terminator using *Agrobacterium*-mediated transformation (see Example 12). It also was found to be reduced in 27 kD-, and 16 kD-gamma-zein. The kernel phenotype of the transgenic seed was normal (i.e., vitreous).

Finally, several events were produced with a construct containing the CZ19B1 promoter, an inverted repeat comprised of 303 bp of the 27 kD gamma-zein cDNA in sense orientation and 303 bp of the 27-kD gamma-zein cDNA in anti-sense orientation. The sequence of this hairpin is found at positions 1-303 of SEQ ID NO:17. The construct contained no terminator and was transformed using *Agrobacterium*-mediated transformation (see Example 12). About 90% of the transgenic maize events generated with this construct were found to be reduced in 27 kD-, and 16 kD-gamma-zein. The kernel phenotype of the transgenic seed was normal (i.e., vitreous).

The endosperm protein profiles of grain in which the 27 kD gamma-zein gene was co-suppressed showed more than a 95% suppression of the protein and an additional reduction of more than 60% in the level of the 16 kD gamma-zein protein, and an approximate three- to five-fold increase in the level of the 15 kD beta-zein protein. Even with the significant decrease in high disulfide containing gamma-zein proteins, grain from these events showed a normal (vitreous) phenotype and were of unaltered test weight and hardness. This result was unexpected as the decrease in the disulfide content, and specifically the decrease in 27 kD gamma-zein, might have been expected to result in grain with a soft or opaque phenotype (see Lopez and Larkins, 1991).

Assays for seed hardness are well known in the art and include such methods as those used in the present invention, described in Pomeranz et al. *Cereal Chemistry* 61(2):147-150 (1984), herein incorporated in its entirety by reference. In essence, breaking susceptibility and grain hardness are measured by density, near-infrared reflectance or average particle size of ground material. The three measure of hardness are highly, linearly, and positively correlated provided the maize samples are homogenous in terms of starch composition (such as waxy, regular or high amylose), and in protein, oil, and ash content.

Assays for the vitreous phenotype are well known in the art and include such methods as those used in the present invention, described in: Erasmus and Taylor (2004). *J. Science of Food and Agriculture*, 84 (9): 920-930, herein incorporated in its entirety by reference. Briefly, the intensity of translucency in maize is linearly correlated to the percentage of kernel illumination ($r=0.99$, $p<0.001$) when placed on a round illuminated area smaller than the projected area of the kernel, allowing light to shine through. Translucency as a percentage of the whole kernel and vitreous endosperm (mass %), was $r=0.77$. Translucency as a percentage of the whole kernel and opaque endosperm (mass %), was $r=-0.72$. Translucency varied by 29.5% between the lowest and highest values, and vitreous endosperm (mass %) varied by 16.8% between the lowest and highest values.

The co-suppression trait was shown to be dominant. Various normal and transgenic maize lines, as well as commercial hybrids, were pollinated with pollen from the gamma-zein co-suppressing events with the result of total suppression of gamma-zein protein in the hemizygous endosperm as determined by SDS-PAGE and immunoblotting. Therefore, the gamma-zein gene co-suppression trait can be introduced into specific pollinators (i.e., high oil corn) using conventional methods and/or the top-cross technology found in U.S. Pat. No. 5,704,160.

$T_3$-segregating grain was phenotyped for gamma-zein protein levels and were divided into two samples, one with wild-type gamma-zein protein levels and a second with reduced gamma-zein protein levels (less than 10% of wild-type). Ground corn from both samples was subjected to an in vitro energy availability assay. The enzyme digestible dry matter (EDDM) assay used in these experiments as an indicator of in vivo digestibility, is known in the art and was performed using enzymes, buffers, and digestion conditions described in Example 2 and Boisen and Fernandez (1997) Animal Feed Science and Technology 68: 277-286); and Boisen and Fernandez (1995) Animal Feed Science and Technology 51:29-43, which are herein incorporated in their entirety by reference. The results clearly indicated that ground corn from gamma-zein co-suppressed grain were more rapidly and extensively digested than corn with normal gamma-zein protein levels, by as much as 20% at the 4 hour time point and as much as an additional 6% at the 6 hr time point.

The role of disulfide bridges in the digestion of corn was investigated in co-suppressed gamma-zein versus control grain. As expected, pretreatment with a strong reducing agent (10 mM DTT) increased the enzyme digestible dry matter (EDDM) level (4 hour digestion) of control grain by 16% but not that of the gamma-zein gene co-suppressed grain. A similar result was observed for various low gamma-zein TopCross hybrids (e.g.: with public grain hybrids 3394 and 32J55). Hence, the impact of DTT on digestibility apparently involves the reduction of disulfides of cysteine residues in gamma-zein proteins. Phenotyped kernel samples (those with normal levels of 27 kD gamma-zein protein and those with low levels of 27 kD gamma-zein protein) from segregating ears from the same events were analyzed using a small-scale simulated wet-milling process incorporating or leaving out a reducing agent (bisulfite) in the steep water (Eckhoff et al., (1996) Cereal Chem. 73:54-57). Similar to the digestibility assay, the reductant had a lesser impact on starch extractability in grain containing low levels of 27 kD gamma-zein protein compared to wild-type grain.

Eighty-three Pioneer inbred lines and 34 Pioneer hybrid lines, representing a wide spectrum of germplasm, were pollinated with pollen from a gamma-zein co-suppressing event with the result of greater than 95% suppression of gamma-zein protein in the hemizygous endosperm as determined by SDS-PAGE and immunoblotting. The same inbred and hybrid lines were grown at the same locations and self-pollinated to provide trait controls. Ears from the crossed inbred and hybrid plants as well as from the control plants were harvested and analyzed for EDDM at the four-hour time point (see Example 2). The results clearly indicated that ground corn from gamma-zein co-suppressed grain were more rapidly and extensively digested than corn with normal gamma-zein protein levels, by as much as 20% at the 4 hour time point. Moreover the grain digestibility of the crossed conversions obtained generally a similar high level of digestibility, i.e. grain conversions derived from poor digestible inbred and hybrid lines generally improved with a larger margin than grain from crosses with lines of higher digestibility (for example, at the 4 hour time point an improvement from 40% to 60% EDDM digestibility in a low digestible line and from 57% to 60% in a high digestible line).

Rumen in situ dry matter digestibility of co-suppressed (i.e. low) 27 kD gamma-zein corn in a top-cross onto three Pioneer grain hybrids: 3394, 35N05, and 32K61, were compared with a control top-cross and with the grain parent. Coarsely ground mature grain samples were weighed into pre-tared nylon bags (4 replicates each). The bags were sealed and placed in the rumen of a fistulated steer for 18 hrs, then washed to remove microbial mass, ovendried, and weighed. Ruminal digestibility of the low gamma-zein grain was on average, 9% higher than the control top-cross and 5% higher than that of the grain parent. (See also: Nocek, J. E. 1988. *In situ and other methods to estimate ruminal protein and energy digestibility*. J. Dairy Sci. 71:2051-2069).

The same samples subjected to the in situ digestion procedure were also evaluated by an automated in vitro gas production method as described by Pell and Schofield (1993, supra). Coarsely ground mature grain samples were weighed into fermentation flasks (9 replicates each). The flasks were inoculated with buffered rumen fluid and incubated at 38° C. for 24 hrs, during which the volume of the fermentation gas was automatically recorded. Average gas production was 2.5 and 3 gas volume (ml) higher for low gamma-zein topcrosses as compared to control top-cross and the grain parent at 15 hours after incubation with rumen fluid.

Immature kernels of various wild-type inbreds & hybrids, sampled at various stages of seed development and maturation, consistently respond to DTT pretreatment in the monogastric in vitro assay when sampled 1 month after pollination or later. The improvement in digestibility with DTT (20% at the 4 hour timepoint) points at a consistent inhibitory role of protein disulfide bonds on digestibility of wild-type kernels from about 28 DAP onwards. From these results one can conclude that kernels harvested at dough stage or silage maturity (approximately 40-45 DAP) would benefit from reduced gamma-zein levels. We also applied DTT pretreatment prior to monogastric in vitro digestion of 27 kD gamma-zein co-suppressed immature kernels (33 DAP), with no apparent effect, similar to our observations for low gamma-zein mature grain. Given the response to DTT for wild-type immature kernels from 28 DAP through maturity, the lack of DTT response for low gamma-zein kernels of any maturity, and the observed improvements in ruminal digestibility of mature low gamma-zein grain, one can deduce, with very high likelihood, that ruminal digestibility of silage maturity kernels will be improved with gamma-zein reduction.

Co-suppressed (i.e. low) 27 kD gamma-zein corn produced as a top-cross onto Pioneer grain hybrid 3394 was compared with a control top-cross and with the grain parent in a chicken feeding trial. A 21-day chick growth trial was performed with digestibility measurements, which demonstrated increased (by 2 percentage units) in vivo dry matter digestibility and increased energy conversion efficiency (by 2%) for the low gamma-zein topcross. In addition, in vivo protein digestibility was improved by 9 percentage units (from 69 to 78%), representing a 13% increase. The increase in protein digestibility resulted in a 29% decrease in nitrogen excretion into the environment.

The same low gamma-zein topcross was also compared with the control topcross in a pig in vivo digestion trial. Metabolizable Energy content of the low gamma zein topcross amounted to 3646 kcal/kg, 73 kcal (or 2%) higher than the control topcross. Protein digestibility was improved from 75.8 to 79.8% for the low gamma-zein topcross. This represents a 4% improvement in protein digestibility, and a 15% reduction in nitrogen excretion into the environment.

Example 4

Suppression of 27 kD Gamma-Zein Through Interruption of the 27 kD Gamma-Zein Gene by Transposon Tagging A maize line containing a Mu-insertion in the 27 kD gamma-zein coding region was isolated using the method of U.S. Pat. No. 5,962,764.

Briefly, a population of F1 maize plants produced by crossing Mutator-active lines (see Bennetzen et. al., Curr Top Microbiol Immunol 1996, 204:195-229 and Chandler, et al., Adv Genet. 1992, 30:77-122) with inbred/hybrid lines and a collection of the F2 seed from each plant are available for screening of mutations (Mu insertion alleles) in genes of known sequence.

Prospective insertion alleles are identified by successive rounds of PCR/DNA dot blot hybridization (using gene-specific primers) first on DNA pools, subsequently on DNA from individuals, as described below:

Pool screening was initiated with 27 kD gamma-zein primers 296 (SEQ ID NO:11) and 170 (SEQ ID NO:12) in combination with Mu TIR primer 9242 (SEQ ID NO:13). Pools were selected for fragment sizing based on signal intensity and reproducibility.

Bands were detected in fifteen of the sixteen pools selected for fragment sizing with primer 170.

In pool screening with primer 296 in conjunction with Mu TIR primer 9242, several intense, reproducible signals were detected. Sixteen pools were selected for fragment sizing from these signals; bands were detected by hybridization in three pools.

An individual master plate was constructed with the nine best pools for which bands were detected. The nine pools were selected based on the putative insertion location of mutator in the gene and possibly the promoter region.

Screening of individual alleles with primers 296 and 170 conjointly with Mu TIR primer 9242 was initiated. Several strong, reproducible signals were detected with both primers 296 and 170. Four individual alleles were cross confirmed with both primers. Seed was advanced for analysis based on pedigree relationship, signal intensity, and reproducibility. Non-mutant seed was used for negative controls.

Many Mu insertions detected by PCR are false-positives due to somatic insertion activity of Mu elements.

In confirmatory PCR, one Mu insertion allele in family PV03 80 B-06 appeared heritable. That is, the insertion was proven to be a germinal event into the 27 kD gamma-zein gene that was able to transmit through the germline into F2 progeny. The heritable TUSC Mu insertion allele into the 27 kD gamma zein gene was renamed "TUSC27".

The material originating from this source was advanced genetically, predominately via backcrossing strategies, to create material suitable for feeding trials, energy availability studies, and product development applications.

Grain from progeny of this TUSC27 line was tested in the in vitro digestibility assay (EDDM) with essentially similar results as observed with the 27 kD gamma-zein gene co-suppressed lines (see Example 3). Seed from this progeny is represented by, but not limited to, ATCC Dep. No: PTA-6323.

Four F2 hybrid grain lines containing TUSC27 were assayed for dry matter digestibility (EDDM) using the procedure of Example 2 against four wild-type lines. Two of the F2 hybrids in PHN46 background (PHP38×PHN46, and PH09B×PHN46) showed 2-5% improvement in digestibility over the wild-type lines. The F2 hybrid in PH581 backgrounds (PH705×PH581) showed 9% improvement and the hybrid in a PH3KP background (PH705×PH3KP) showed 3% improvement over its wild-type line. All F2 hybrids showed 2-8% improvement in EDDM over the control hybrid 3335—a commercially available "high digestibility" line not altered in seed storage protein content. All hybrid maize lines used have been deposited with the Patent Depository of the American Type Culture Collection (ATCC), Manassas, Va.

The trait was semi-dominant rather than recessive: that is the 27 kD gamma-zein level in endosperm showed a strong gene-dosage effect.

Example 5

Suppression of 27 kD Gamma-Zein by Over-Expression of High-Sulfur Proteins Through Competition for Biosynthetically Available Pools of Sulfur Amino Acids Transgenic plants expressing the 18 kD delta-zein protein or the engineered high-lysine, high-sulfur protein hordothionin 12 (U.S. Pat. No. 5,990,389) in the endosperm showed an 80% decrease in gamma-zein protein levels, possibly due to limitations of free sulfur-amino acid pools. Seed from these events were tested essentially under the same conditions as seed from gamma-zein gene co-suppressing events (see Example 2) using the in vitro digestibility assay in both the presence and absence of disulfide reducing agents. The results obtained were similar to those described in the previous two Examples. The reduced levels of gamma-zein protein had a large positive impact on dry matter digestibility in the absence of DTT. Plants expressing high-sulfur protein showed 6% improvement in EDDM dry matter digestibility. The improvement in digestibility in this case is not as high as in CS27 (example 3). This could be due to the higher residual level of gamma zein in high-sulfur protein plants as compared to CS27. Maize plants ectopically expressing 18 kD delta-zein protein or hordothionin 12 protein in corn endosperm were both produced using the top-cross technology. Comparable results were also obtained using hemizygous seed from top-crossed elite inbreds and hybrids with hordothionin 12 corn as the male parent. Grain from these plants showed improved digestibility, and therefore improved energy availability.

Example 6

Cloning of a Novel Maize 18 kD Alpha-Globulin

An 18 kD alpha-globulin full-length cDNA (B73 allele) was cloned from a maize endosperm library (mid and late development). Based on EST numbers alpha-globulin transcripts are relatively rare (compared to other seed protein transcripts) and represent approximately 0.1% of the endosperm mRNA during mid development. Different maize inbred lines showed considerable allelism including several SNP's. The 18 kD alpha-globulin gene has been located on chromosome 6, bin 6.05.

The coding region of the B73 allele is 618 bp. The encoded 206 amino acid sequence of the pro-polypeptide contains a predicted N-terminal ER import signal peptide of 23 amino acids. Remarkable is the string of tryptophane (W) residues ("tryptophane box"), which has been also observed in puroindolins from wheat. Puroindolins in wheat have been associated with grain hardness. The 18 kD alpha-globulin of the present invention and the puroindolins are distantly evolutionary related and belong both to the 2S albumin gene superfamily.

SNP's and Alleles

Different corn inbred lines show considerable allelism. For example, sequence fragments isolated from B73 and Mo17 are shown below. The two alleles differ by mostly insertions '*' and a few SNP's (lower case bold). (See also SEQ ID NOS: 9 and 10).

```
18 kD alpha-globulin, B73 allele, partial
AATTCGCCCTTGTCATTCTGGATTTGCACGCGCACAGTACACATGCTGCG tCTTGCACgTCGCGCCGACTCgCTtT*********AACCaTGGTAGCTAG

TACTGGTCGCCGCCGGAGAAGATGCTGCACTCCTGGGGCTCCGACAGCCG

GCACATCATCGGCAACCCCGCGGCGTACTCCCGGGCCTTCGTAAGCCTCA

CGCGGCCGATCCTTGGCCCGCCGCCGGTGGTGCCGGGACGACACGGTGGA

TACATCTGCcgcTGGccaCCCTgaCCgtagCCGTATCCCTCTCCTGGCCG

GCTGCAGGGGTAGTAGTAGCCCCCCTGTCCTCCTCCTCCTCCCTGCGGCG

GCGGCTGCTGCTGCCGCCCCCATGGCCACCAGCCTTTCTCCAGcGGCGGC

ATGGCCTCCTCGTAGCCCCTGACCATGCTCCGGATGGCGGCGCAGCGGCA

CTCGCGGCTCACGTCCTGGAGCTGCTGGCAGCACCGCATCCGGAGCCCGG

TGCCCCACCGGAACGGGCCAACGCCGCCGCCGcCGCCGCCGCCGGTTAGC

TGCCGGTCGAGGAAAGGGCG 18 kD alpha-globulin, Mo17 allele, partial
AATTCGCCCTTGTCATTCTGGATTTGCACGCGCACAGTACACATGCTGCG

CCTTGCACGTCGCGCCGACTCACTCTTTTTTTTTAACCCTGGTAGCTAG

TACTGGTCGCCGCCGGAGAAGATGCTGCACTCCTGGGGCTCCGACAGCCG

GCACATCATCGGCAACCCCGCGGCGTACTCCCGGGCCTTCGTAAGCCTCA

CGCGGCCGATCCTTGGCCC******GGTGGTGCCGGGACGACACGGTGGA

TACATCTGCGTTTGGTATCCCTCTCCTGCCC*****************G

GCTGCAGGGGTAGTAGTAGCCCCCCTGTCCTCCTCCTCCTCCCTGCGGCG

GCGGCTGCTGCTGCCGCCCCCATGGCCACCAGCCTTTCTCCAGAGGCGGC

ATGGCCTCCTCGTAGCCCCTGACCATGCTCCGGATGGCGGCGCAGCGGCA

CTCGCGGCTCACGTCCTGGAGCTGCTGGCAGCACCGCATCCGGAGCCCGG

TGCCCCACCGGAACGGGCC*********GCCGACGCCGCCGCCGGTTAGC

TGCCGGTCGAGGAAAGGGCG
```

Example 7

Transgenic Expression of 18 kD Alpha-Globulin in Maize

The cDNA encoding the maize 18 kD alpha-globulin was placed under the control of the strong endosperm specific 27 kD gamma-zein promoter and introduced into maize plants by *Agrobacterium*-mediated transformation. Several transgenic events were identified that had increased levels alpha-globulin protein as demonstrated by SDS-PAGE and staining of gels with Coomassie blue. A prominent band was visible at a molecular weight corresponding to the 18 kD protein extracted from transgenic seed, but absent from protein extracted similarly from wild type seed. The seed of transformants and progeny overexpressing 18 kD alpha-globulin is phenotypically normal (vitreous).

The identity of the polypeptide migrating at 18 kD in the polyacrylamide gel was confirmed by immune blotting using 18 kD alpha-globulin protein specific antibodies. In seed of transgenic plants, the 18 kD alpha-globulin protein accumulated to levels of between 2-5% of the SDS-sample buffer (60 mM Tris, pH 6.8, 100 mM DTT, 2% SDS) extractable seed protein. Seed expressing these amounts of omega zein protein contained 0.162% tryptophan per dry weight compared to No. 2 yellow corn having 0.06% tryptophan amounting to a greater-than 100% increase in tryptophan levels. Also, sulfur amino acid content was increased by about 80%.

In vitro dry matter digestibility of corn overexpressing 18 kD alpha-globulin was determined using the monogastric EDDM assay.

18 kD Alpha-globulin overexpression resulted in improved 4 hr EDDM by 10.6 percentage units. An overnight soak in 10 mM of the strong reducing agent dithiothreietol (DTT), known to maximize in vitro digestibility. DTT treatment improved digestibility beyond that reached with 18 kD alpha-globulin overexpression (by 3.4 percentage units), indicated that the improvement in digestibility attainable with removing digestion-limiting disulfide bonds is partially additive to the improvement obtained with alpha-globulin over-expression. Similarly, improvements made by combining gamma-zein co-suppression and 18 kD alpha-globulin overexpression can be expected to be partially additive.

Example 8

Preparation of Maize 18 kD Alpha-Globulin-Specific Antibodies

Standard methods for the production of antibodies were used such as those described in Harlow and Lane (1988) *Antibodies: A Laboratory Manual* (Cold Spring Harbor, N.Y.: Cold Spring Harbor Laboratory; incorporated herein in its entirety by reference. Specifically, antibodies for 18 kD alpha-globulin polypeptides were produced by injecting female New Zealand white rabbits (Bethyl Laboratory, Montgomery, Tex.) six times with homogenized polyacrylamide gel slices containing 100 micrograms of PAGE purified alpha-globulin polypeptide. The alpha-globulin polypeptide was purified by sub-cloning into a pET28 vector resulting in an insert encoding a His-tag fusion of the alpha-globulin polypeptide. The fusion protein was expressed in *E. coli* BL21 (DE3) cells and purified from the lysate by Nickel chelation chromatography. The denatured purified fusion protein was used for immunization.

Animals were then bled at two week intervals. The antibodies were further purified by affinity-chromatography with Affigel 15 (BioRad)-immobilized antigen as described by Harlow and Lane (1988) *Antibodies: A Laboratory Manual*, Cold Spring Harbor, N.Y. The affinity column was prepared with purified 18 kD alpha-globulin protein essentially as recommended by BioRad®. Immune detection of antigens on PVDF blots was carried out following the protocol of Meyer et al. (1988) J. Cell. Biol. 107:163; incorporated herein in its entirety by reference, using the ECL kit from Amersham (Arlington Heights, Ill.).

Example 9

Cloning and Sequencing of Maize, *Sorghum* and Sugarcane 50 kD Legumin 1 Protein A 50 kD legumin 1 nucleotide sequence was cloned from a maize endosperm cDNA library (mid and late development). Based on EST numbers 50 kD legumin 1 transcripts are relatively abundant (compared to other seed protein transcripts) and represent approximately 0.5% of the endosperm mRNA during mid development. The 50 kD legumin 1 DNA sequences isolated from different inbred lines showed a considerable level of polymorphism. The 50 kD legumin 1 gene has been mapped to chromosome 6, Bin 6.01.

Expressed sequence tags of nucleotide sequences from sorghum and sugarcane indicated the presence of legumin genes (genebank Account No. for sorghum EST: OV1_21_C09 and for sugarcane EST: CA202717) in the genome of these cereals. Clones of cDNA represented by these ESTs were sequenced and compared to maize 50 kD legumin 1. Both the sorghum and the sugarcane cDNA and their encoded polypeptide sequences showed a close phylogenetic relationship between the maize, sorghum and sugarcane sequences. Both the sorghum and the sugarcane legumin polypeptide sequences share 85% overall identity with corn legumin 1. All three share the unique property of missing an evolutionary conserved 11S globulin pro-protein cleavage site.

Example 10

Preparation of Maize 50 kD Legumin 1-Specific Antibodies

Antibodies to this protein were prepared essentially as described for the 18 kD alpha-globulin polypeptide.

Example 11

Transgenic Expression of 50 kD Legumin 1 in Maize

Additional copies of the 50 kD legumin 1 cDNA under control of the strong endosperm specific 27 kD gamma-zein promoter were introduced into transgenic corn plants. Several maize lines were identified that over-express the 50 kD legumin 1 protein. Over-expression was demonstrated by SDS-PAGE and staining of the gels with Coomassie blue. A prominent band was visible at 50 kD in protein extracted from transgenic seed but absent in protein from wild type seed. The identity of the polypeptide band was confirmed to be the 50 kD legumin 1 protein by immune blotting using the 50 kD legumin 1 protein specific antibodies. In the seed of transgenic maize plants over-expressing the 50 kD legumin 1 protein, this protein accumulates to levels of between 2-5% of the SDS-sample buffer (60 mM Tris, pH 6.8, 100 mM DTT, 2% SDS) extractable seed protein. The seed over-expressing the 50 kD legumin 1 protein showed a normal (vitreous) phenotype. In addition to overexpression of the 50 kD legumin 1, independent transformants were also obtained in which the legumin 1 gene was silenced as evidenced by reduced protein level using immune blotting. These events were also silenced for the 27 kD gamma-zein, by apparent promoter-induced silencing. Finally, one event was obtained in which the 27 kD gamma-zein was silenced, but the 50 KD legumin 1 clearly overexpressed as assessed by SDS-PAGE/ Coomassie blue staining and immune blotting. Seed from all these events were phenotypically normal (vitreous).

Two segregating events, both silenced for 27 kD gamma-zein, but only one overexpressing the corn legumin 1, were evaluated in the monogastric EDDM assay. 50 kD legumin 1 overexpression in low gamma-zein background resulted in improved grain digestibility by about 3.2 percentage units.

These results showed not only that overexpression of corn 50 kD legumin 1 improves digestibility, but that these improvements are additive to those obtained with 27 kD gamma-zein co-suppression.

Example 12

*Agrobacterium*-Mediated Transformation of Maize

For *Agrobacterium*-mediated transformation of maize, a nucleotide sequence encoding a protein of the present invention was operably linked to either the 27 kD gamma-zein promoter or the maize CZ19B1 promoter, and the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of *Agrobacterium*, where the bacteria are capable of transferring the nucleotide sequence of interest to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step is contemplated. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). The immature embryos were cultured on solid medium with a selective agent resulting in the selective growth of transformed cells. The callus was then regenerated into plants (step 5: the regeneration step), and calli grown on selective medium were cultured on solid medium to regenerate the plants.

Example 13

*Agrobacterium*-Mediated Transformation of Sorghum

For *Agrobacterium*-mediated transformation of sorghum the method of Cai et al. can be employed (U.S. patent application Ser. No. 09/056,418), the contents of which are hereby incorporated by reference). This method can be employed with a nucleotide sequence encoding any of the proteins of the present invention using the promoters described in Example 12 herein, or another suitable promoter.

Example 14

Transformation of Maize Embryos by Particle Bombardment

Immature maize embryos from greenhouse donor plants are bombarded with a plasmid containing the nucleotide sequence encoding a protein of the present invention operably linked to a selected promoter plus a plasmid containing the selectable marker gene PAT (Wohlleben et al. (1988) *Gene* 70:25-37) that confers resistance to the herbicide Bialaphos. Transformation is performed as follows.
Preparation of Target Tissue The ears are surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.
Preparation of DNA A plasmid vector comprising the nucleotide sequence encoding a protein of the present invention operably linked to a promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.
Particle Gun Treatment The sample plates are bombarded at level #4 in particle gun #HE34-1 or #HE34-2. All samples receive a single shot at 650 PSI, with a total of ten aliquots taken from each tube of prepared particles/DNA.
Subsequent Treatment Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the desired phenotypic trait.

Bombardment and Culture Media

Bombardment medium (560Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-1$H_2O$ following adjustment to pH 5.8 with KOH); 3.0 g/l Gelrite (added after bringing to volume with D-1$H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-1$H_2O$ after adjusting to pH 5.6); 3.0 g/l Gelrite (added after bringing to volume with D-1$H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-1$H_2O$ after adjusting pH to 5.6); and 6 g/l bacto-agar (added after bringing to volume with polished D-1$H_2O$), sterilized and cooled to 60° C.

Example 15

Transformation of Rice Embryogenic Callus by Bombardment

Embryogenic callus cultures derived from the scutellum of germinating seeds serve as the source material for transformation experiments. This material is generated by germinating sterile rice seeds on a callus initiation media (MS salts, Nitsch and Nitsch vitamins, 1.0 mg/l 2,4-D and 10 µM $AgNO_3$) in the dark at 27-28° C. Embryogenic callus proliferating from the scutellum of the embryos is then transferred to CM media (N6 salts, Nitsch and Nitsch vitamins, 1 mg/l 2,4-D, Chu et al., 1985, Sci. Sinica 18:659-668). Callus cultures are maintained on CM by routine sub-culture at two week intervals and used for transformation within 10 weeks of initiation.

Callus is prepared for transformation by subculturing 0.5-1.0 mm pieces approximately 1 mm apart, arranged in a circular area of about 4 cm in diameter, in the center of a circle of Whatman #541 paper placed on CM media. The plates with callus are incubated in the dark at 27-28 C for 3-5 days. Prior to bombardment, the filters with callus are transferred to CM supplemented with 0.25 M mannitol and 0.25 M sorbitol for 3 hr. in the dark. The petri dish lids are then left ajar for 20-45 minutes in a sterile hood to allow moisture on tissue to dissipate.

Circular plasmid DNA from two different plasmids one containing the selectable marker for rice transformation and one containing the nucleotide of the invention, are co-precipitated onto the surface of gold particles. To accomplish this, a total of 10 µg of DNA at a 2:1 ratio of trait:selectable marker DNAs is added to a 50 µl aliquot of gold particles resuspended at a concentration of 60 mg ml-[1]. Calcium chloride (50 µl of a 2.5 M solution) and spermidine (20 µl of a 0.1 M solution) are then added to the gold-DNA suspension as the tube is vortexing for 3 min. The gold particles are centrifuged in a microfuge for 1 sec and the supernatant removed. The gold particles are then washed twice with 1 ml of absolute ethanol and then resuspended in 50 µl of absolute ethanol and sonicated (bath sonicator) for one second to disperse the gold particles. The gold suspension is incubated at −70 C for five minutes and sonicated (bath sonicator) if needed to disperse the particles. Six µl of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28-29 inches Hg. The macrocarrier is accelerated with a helium shock wave using a rupture membrane that bursts when the He pressure in the shock tube reaches 1080-1100 psi. The tissue is placed approximately 8 cm from the stopping screen and the callus is bombarded two times. Five to seven plates of tissue are bombarded in this way with the DNA-coated gold particles. Following bombardment, the callus tissue is transferred to CM media without supplemental sorbitol or mannitol.

Within 3-5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates incubated in the dark for 4 weeks at 27-28° C. After 4 weeks, transgenic callus events are identified, transferred to fresh SM plates and grown for an additional 2 weeks in the dark at 27-28° C.

Growing callus is transferred to RM1 media (MS salts, Nitsch and Nitsch vitamins, 2% sucrose, 3% sorbitol, 0.4% gelrite+50 ppm hyg B) for 2 weeks in the dark at 25° C. After 2 weeks the callus is transferred to RM2 media (MS salts, Nitsch and Nitsch vitamins, 3% sucrose, 0.4% gelrite+50 ppm hyg B) and placed under cool white light (~40 µEm$^{-2}$s$^{-1}$) with a 12 hr photoperiod at 25° C. and 30-40% humidity. After 2-4 weeks in the light, callus generally begins to organize, and form shoots. Shoots are removed from surrounding callus/media and gently transferred to RM3 media (1/2×MS salts, Nitsch and Nitsch vitamins, 1% sucrose+50 ppm hygromycin B) in phytatrays (Sigma Chemical Co., St. Louis, Mo.) and incubation is continued using the same conditions as described in the previous step.

Plants are transferred from RM3 to 4" pots containing Metro mix 350 after 2-3 weeks, when sufficient root and shoot growth has occurred. Plants are grown using a 12 hr/12 hr light/dark cycle using ~30/18° C. day/night temperature regimen.

Example 16

Breeding Crosses Made with Transgenic or Mutant High-Digestible-Grain Corn Lines A transgenic line that segregated for co-suppressed 4-coumarate ligase (4CL) was planted and the segregating progeny was either self-fertilized or pollinated with the transgenic low gamma-zein line. Ground grain samples were subjected to a two-stage in-vitro-mimicking small intestinal digestion procedure as described in Example 2 followed by an additional step that included viscozyme that mimics large-intestinal fermentation (Boisen and Fernandez, 1997, Animal Feed Science and Technology 68:277-286). The improvement in digestibility for low gamma-zein corn in this two-stage assay, and the independent improvement obtained with 4CL co-suppression were additive as indicated by an approximately 2% increase in EDDM value for 4CL grains that was top-crossed with CS27 pollen as compared to 4CL grains top-crossed with control pollen.

Example 17

Isolation of Kafirin sequences from *Sorghum*

Kafirin fragments for RNAi cassette construction are obtained by PCR amplification from kafirin cDNA clones. For this purpose a sorghum cDNA library from developing endosperm (20 days after pollination) is constructed and EST sequences are obtained from 1000 randomly selected cDNA clones. The EST sequences are clustered into EST contigs and analyzed to determine the complete transcript sequences and the relative expression levels of kafirin genes. Based on this analysis conserved regions of the most abundantly expressed kafirin genes are selected for PCR amplification and up to six amplified fragments are spliced in tandem, converted into a chimeric self-complimentary hairpin construct and inserted into an endosperm-specific 27 kD gamma-zein promoter cassette.

Example 18

Modulating Seed Proteins in *Sorghum*

Building of vectors for *Agrobacterium*-mediated plant transformation. A plant transformation vector for the delivery of the two tandem-assembled RNAi gene suppression cassettes are constructed. Each step of vector construction is performed by standard DNA analysis techniques (See, for example, Sambrook et al. (1989) *Molecular Cloning: A Laboratory Manual* (Cold Spring Harbor, Laboratory Press, Plainview, N.Y.; or Gelvin et al., *Plant Molecular Biology Manual* (1990); each incorporated herein in its entirety by reference.). After completion, the region between the T-DNA borders of each vectors is sequenced in its entirety using standard sequencing technology.

DNA fragments for biolistic transformation (PMI system) Gene cassettes for biolistic transformation are isolated as linear DNA fragments from source plasmids after restriction digestion. Purification of DNA fragments by agarose electrophoresis are carried out twice to minimize the risk of contamination with plasmid backbone fragments (notably bacterial antibiotic markers).
Transformation

*Agrobacterium*-mediated transformation of sorghum is performed by the method described in Example 12.

Biolistic transformation is done by co-bombarding minimal concentrations of linearized transgene fragments and the PMI selectable marker cassettes. This strategy has been successfully used to minimize DNA rearrangements in transgenic plants (Loc, et al., 2002; Breitler, et. al., 2002) and reduces the risk of trait loss due to transgene silencing. The PMI system (see above) addresses concerns often associated with transgenic crops by avoiding herbicide resistance for selection.

For each vector or construct 200 independent events are initially generated. This number produces at least 5 efficacious, high quality T0 events per vector available after event sorting for the breeding program. All T0 plants are grown in the greenhouse and self-pollinated. A minimum of 50 T1 seeds per event are harvested.
Event Sorting-Molecular Analysis Event analysis has two major components: 1) PCR for trait gene copy number, absence of vector backbone DNA, herbicide gene elimination, and Southern for rearrangement analysis; and 2) digestibility, seed protein and micronutrient analysis.

1) High-copy number and rearranged events and events with integrated vector backbone will be eliminated because of regulatory concerns (T0 plants). Because of gene flow issues, only events that do not contain the herbicide marker gene after *Agrobacterium*-mediated transformation are selected for breeding. Typically at least 50% of the events segregate for the marker gene. Segregation and elimination of the marker gene are assayed by PCR of 50 segregating T2 plants.

Seedlings that contain only the trait genes are transferred to pots for propagation. The seeds harvested from these marker-free plants are used for event analysis and trait gene expression analysis.

The trait efficacy of the remaining events are assessed by protein expression analysis (protein electrophoresis, immune blotting) and by grain composition analysis. Altered expression of kafirin genes can easiest be assayed in stained protein gels. Zein-antibodies that cross-react with corresponding kafirins are used.

These analysis techniques performed on single seed are routine and are well known to those of skill in the art. Grain samples are further evaluated for grain quality characteristics (hardness, grain moisture, test weight) and grain yield. The outcome of this analysis is the selection of 5 events (per transformation experiment) for breeding and field release.

Example 19

Transgenic Down Regulation of Alpha-Zein (CS19,CSAZ)

Expression cassettes were made comprising a chimeric maize alpha-zein fusion of polynucleotide fragments from the coding regions of 19 KD alpha-zein clone D1 (563 bp), 19 KD alpha-zein clone B1 (536 bp), and 22 KD alpha-zein (610 bp) (SEQ ID NO: 16). The cassette included a selectable marker gene such as PAT (Wohlleben et al (1988) Gene 70:25-37, or BAR for resistance to Basta/phosphinothricin were constructed. The polynucleotides were operably linked to the CZ19B1 promoter to direct expression to maize endosperm. The construction of such expression cassettes is well known to those of skill in the art in light of the present disclosure. See, for example, e.g., Sambrook et al. (1989) *Molecular Cloning: A Laboratory Manual* (Cold Spring Harbor, Laboratory Press, Plainview, N.Y.; Gelvin et al. Plant Molecular Biology Manual (1990); each incorporated herein in its entirety by reference.

Corn was transformed as described in Example 14 using particle bombardment. Seeds from 30 transgenic events were analyzed for protein profiles by SDS-PAGE and more than 20% of the events showed segregating kernels with suppressed (>90% suppression of the alpha-zein protein when compared to non-transgenic control seed) alpha-zein protein levels (designated as CS-AZ). One event showed suppression of only the 19 kD alpha-zein (designated as CS19).

Total alpha-zein suppression (CS-AZ) resulted in improved 4 hr EEDM by 7 percentage units. Similarly, 19 kD alpha-zein suppression (CS19) resulted in improved 4 hr EEDM by 4.9 percentage units. An overnight soak in 10 mM of the strong reducing agent dithiothreietol (DTT) is known to maximize in vitro digestibility. Digestibility improved beyond that reached with 19 kD alpha-zein co-suppression (by 4.3 percentage units), indicated that the improvement in digestibility attainable with reduction of alpha-zein protein is partially additive to the improvement obtained with 19 kD alpha-zein co-suppression. Similarly, improvements made by combining 27 kD gamma-zein co-suppression and total alpha-zein suppression or with 19 kD alpha-zein co-suppression over-expression have been found to be to be partially additive (See Example 24).

Example 20

Combination of Over-Expressed Corn Legumin and Co-Suppressed 27 kD Gamma-Zein

A construct is made that links in tandem a selectable marker gene, a corn legumin over-expression cassette and a 27 KD gamma-zein co-suppression cassette. The selectable marker gene consists of PAT for resistance to Basta/phosphinothricin. The corn legumin coding sequence is placed under the transcriptional control of the maize GZ-W64A promoter and terminator (SEQ ID NOs:26 and 27) (Reina, M. et al, (1990), Nucleic Acids Res., 18:6426) to drive expression in maize endosperm as described in Example 11. The 27 KD gamma-zein co-suppression cassette contains the CZ19B1 promoter, and an inverted repeat with 27 kD gamma-zein cDNA fragments as described in Example 3. The entire construct of linked cassettes is transformed into maize by *Agrobacterium*-mediated transformation and resulting T0 plants are pollinated by a non-transgenic male parent corn plant.

Seed from transgenic events are analyzed for their seed protein profile by SDS-PAGE and Coomassie-staining of gels. In the protein profiles of kernels, about 90% of events indicate a 1:1 segregation of wildtype seed protein profiles and altered seed protein profile phenotypes. About 90% of the transgenic maize events generated with this construct are found to contain segregating kernels that are reduced in 27 kD-, and 16 kD-gamma-zein by at least 50% (dry weight; i.e.: "low gamma-zein phenotype") and about 30% of the transgenic events are found to contain segregating kernels that are increased in corn legumin by at least 200% (dry weight; i.e.: "high corn legumin protein phenotype") in addition to the reduced gamma-zein protein phenotype. The kernel phenotype of the transgenic seed is normal (i.e., vitreous).

Segregating seed from low gamma-zein/high corn legumin protein transgenic events are analyzed by SDS-PAGE for their seed protein phenotypes and sorted into two batches of 50 seed each. One batch contains seed with wild type seed protein phenotype (controls) and the second batch contains seed with low gamma-zein/high corn legumin protein phenotypes. The seed of both batches are ground and analyzed by the EDDM assay. The analysis shows improved EDDM digestibility of the seed sample with low gamma-zein/high corn legumin protein phenotypes compared to the seed sample with the wild type seed protein phenotype.

Moreover, the EDDM improvement in the sample derived from low gamma-zein/high corn legumin seed is greater than in seed samples with only a low 27 kD gamma-zein content (Example 3) or in seed samples with only a high corn legumin protein content (Example 11); showing a partially additive effect of the suppression of gamma-zein and the increased expression of corn legumin on grain digestibility.

Example 21

Combination of Over-Expressed Corn Alpha-Globulin and Co-Suppressed 27 kD Gamma-Zein A construct is made comprising a tandem-linked corn alpha-globulin over-expression cassette, a 27 KD gamma-zein co-supression cassette, and selectable marker cassette. The selectable marker cassette consists of the ubiquitin promoter, PAT selectable marker (for resistance to Basta/phosphinothricin) and PINII terminator. The corn alpha-globulin coding sequence (SEQ ID NO:3) is placed under the transcriptional control of the maize GZ-W64A promoter and terminator (SEQ ID NOs:26 and 27) to drive expression in maize endosperm as described in Example 11. The 27 KD gamma-zein co-suppression cassette contains the CZ19B1 promoter, and an inverted repeat with 27 kD gamma-zein cDNA fragments as described in Example 3. The entire construct of linked cassettes is transformed into maize by *Agrobacterium*-mediated transformation and resulting T0 plants are pollinated by a nontransgenic male parent corn plant.

Seed from transgenic events are analyzed for their seed protein profile by SDS-PAGE and Coomassie-staining of gels. The protein profiles of kernels in about 90% of events indicate a 1:1 segregation of wildtype seed protein profiles to altered seed protein profile phenotypes. About 90% of the transgenic maize events generated with this construct are found to contain segregating kernels that are reduced in 27 kD-, and 16 kD-gamma-zein by at least 50% (dry weight; e.g.: "low gamma-zein phenotype") and about 30% of the transgenic events are found to contain segregating kernels that are increased in corn alpha-globulin by at least 500% (dry weight; e.g.: "high corn alpha-globulin protein phenotype") in addition to the reduced gamma-zein protein phenotype. The kernel phenotype of the transgenic seed is normal (i.e., vitreous).

Segregating seed from low gamma-zein/high corn alpha-globulin protein transgenic events are analyzed by SDS-PAGE for their seed protein phenotypes and sorted into two batches of 50 seed each. One batch contains seed with wild type seed protein phenotype (controls) and the second batch contains seed with low gamma-zein/high corn alpha-globulin protein phenotypes.

The seed of both batches are ground and analyzed by the EDDM assay. The analysis shows improved EDDM digestibility of the sample with seed with low gamma-zein/high corn alpha-globulin protein phenotypes compared to the EDDM digestibility of the wild type seed sample. Moreover, the EDDM improvement in the low gamma-zein/high corn alpha-globulin seed is greater than in seed samples with only a low 27 kD gamma-zein content (Example 3), or in seed samples with only a high corn alpha-globulin protein content (Example 7), demonstrating a partially additive effect on grain digestibility of the suppression of gamma-zein and the increased expression of corn alpha-globulin.

Example 22

Transgenic Over-Expression of Combination of Alpha-Globulins and Corn Legumin 1

A construct is made comprising a tandem-linked corn alpha-globulin over-expression cassette, a corn legumin overexpression cassette and selectable-marker cassette. The selectable marker cassette consists of the ubiquitin promoter, PAT selectable marker (for resistance to Basta/phosphinothricin) and PINII terminator. The corn alpha-globulin coding sequence is placed under the transcriptional control of the maize floury2 22 kD alpha-zein promoter and terminator to drive expression in maize endosperm. The corn legumin overexpression cassette contains the corn legumin coding sequence placed under the transcriptional control of the maize GZ-W64A promoter and terminator to drive expression in maize endosperm as described in Example 11. The entire construct of linked cassettes is transformed into maize by *Agrobacterium*-mediated transformation and resulting T0 plants are pollinated by a nontransgenic male parent corn plant.

Seed from transgenic events are analyzed for their seed protein profile by SDS-PAGE and Coomassie-staining of gels. The protein profiles of kernels in about 90% of events indicate a 1:1 segregation of wild-type seed protein profiles to altered seed protein profile phenotypes. About 50% of the transgenic maize events generated with this construct are found to contain segregating kernels that are increased in corn alpha-globulin by at least 500% (dry weight; e.g.: "high corn alpha-globulin protein phenotype") and in corn legumin by at least 200% (dry weight; e.g.: "high corn legumin phenotype"). The kernel phenotype of the transgenic seed is normal (i.e., vitreous).

Segregating seed from high corn legumin/high corn alpha-globulin protein transgenic events are analyzed by SDS-PAGE for their seed protein phenotypes and sorted into two batches of 50 seed each. One batch contains seed with wild type seed protein phenotype (controls) and the second batch contains seed with high corn legumin/high corn alpha-globulin protein phenotypes. The seed of both batches are ground and analyzed by the EDDM assay. The analysis shows improved EDDM digestibility of the seed sample with high corn legumin/high corn alpha-globulin protein phenotypes compared to the EDDM digestibility of the seed sample with wild-type seed protein phenotype. Moreover, the EDDM improvement in the sample derived from high corn legumin/ high corn alpha-globulin seed is greater than in samples from seed with only a high corn legumin content (Example 11) or in samples from seed with only a high corn alpha-globulin protein content (Example 7), demonstrating a partially additive effect of the increased expression of corn legumin and the increased expression of corn alpha-globulin on grain digestibility.

Example 23

Down Regulation of 27 kD Gamma-Zein and Alpha-Zeins

A construct is made comprising a tandem-linked selectable marker cassette, and a 27 KD gamma-zein/22 kD alpha-zein/ 19 kD alpha-zein clone B/19 kD alpha-zein clone D co-supression cassette. The selectable marker cassette consists of the ubiquitin promoter, PAT selectable marker (for resistance to Basta/phosphinothricin) and PINII terminator. The co-suppression cassette contains the CZ19B1 promoter and an inverted repeat with fragments of the 27 kD gamma-zein cDNA, the 19 kD alpha-zein B1 cDNA, the 19 kD alpha-zein D1 cDNA and the 22 kD alpha-zein 1 cDNA (SEQ ID NO: 17). The transcriptional fusion is arranged as an inverted repeat around a spliceable ADH1 INTRON1 to effect silencing of all genes and genes highly similar to genes represented in the fusion.

The entire construct of linked cassettes is transformed into maize by *Agrobacterium*-mediated transformation and resulting T0 plants are pollinated by a nontransgenic male parent corn plant.

Seed from transgenic events are analyzed for their seed protein profile by SDS-PAGE and Coomassie-staining of gels. The protein profiles of kernels in about 90% of events indicate a 1:1 segregation of wild-type seed protein profiles to altered seed protein profile phenotypes. About 90% of the transgenic maize events generated with this construct are found to contain segregating kernels that are reduced in 27 kD- and 16 kD-gamma-zein, all 22 kD alpha-zein proteins, and all 19 kD alpha-zein proteins. These zeins are suppressed by at least 90% (dry weight; e.g.: "low gamma-zein/low alpha-zein phenotype") in about 90% of the altered seed protein events. Segregating seed from low gamma-zein/low alpha-zein transgenic events are analyzed by SDS-PAGE for their seed protein phenotypes and sorted into two batches of 50 seed each. One batch contains seed with wild type seed protein phenotype (controls) and the second batch contains seed with low gamma-zein/low alpha-zein protein phenotypes.

The seed of both batches are ground and analyzed by the EDDM assay. The analysis shows improved EDDM digestibility of the seed sample with low gamma-zein/low alpha-zein protein phenotypes compared to the wild-type seed sample. Moreover, the EDDM improvement in the low gamma-zein/low alpha-zein seeds sample is greater than in seed samples with only a low 27 kD gamma-zein content (Example 3) or in seed samples with only a low alpha-zein protein content (Example 19); demonstrating a partially additive effect of the suppression of gamma-zein and the suppression of alpha-zeins on grain digestibility.

Example 24

Combined Down-Regulation of 27 kD and 16 kD Gamma-Zein, 22 kD and 19 kD Alpha-Zein and Over-Expression of Alpha-Globulin, 15 kD Beta-Zein, and 18 kD Delta Zein A stacked construct (SEQ ID NO: 17) was constructed which included the following expression cassettes: floury2 promoter::18 KD alpha-globulin coding sequence::floury2 terminator; ZM-LEG1A PRO (the promoter from the maize legumin gene): HSZ (high sulfur zein) coding sequence::ZM-LEG1 terminator; GZ-W64A Pro::15 KD Beta Zein coding sequence::GZ-W64A terminator; and the CZ19B1 promoter driving a transcriptional fusion of fragments of 27 KD gamma-zein, both 19 KD alpha-zeins, 22 KD alpha-zein, and Lysine Ketoglutarate Reductase (LKR; Arruda P, et al, (2000), Trends Plant Sci. 5:324-330). The transcriptional fusion was arranged as an inverted repeat around a spliceable ADH1 INTRON1 to effect silencing of all five genes represented in the fusion.

The entire construct of linked cassettes was transformed into maize by *Agrobacterium*-mediated transformation. 361 T0 plants derived from 252 independent events were obtained and pollinated by a nontransgenic male parent corn plant. From those 361 ears, 302 ears contained more than 50 kernels per ear.

Four to six seed from each of these ears were analyzed by SDS-PAGE for their protein profiles. This analysis identified 273 ears (90%) that contained seeds segregating for altered seed protein profiles: that is the 27 kD- and 16 kD gamma-zeins, all 22 kD- and all 19 kD alpha-zein proteins were suppressed by at least 90% (dry weight) Strong protein bands migrating in SDS-PAGE gels with apparent molecular weights of 15 kD, 18 kD and 50 kD were observed.

The identity of the 15 kD protein as the 15 kD beta-zein, of the 18 kD protein as the 18 kD corn alpha-globulin and 18 kD delta-zein proteins and of the 50 kD protein as the 50 kD corn legumin was confirmed by immuno-blotting using beta-zein, alpha-globulin, delta-zein and corn legumin specific antibodies (Woo et al) with seed extracts from 9 selected events. Moreover, the suppression of LKR was also confirmed in these events by immuno-blotting. These results demonstrated a very high rate of combined efficacy of the co-suppression cassette and the linked over-expression cassettes.

Segregating seed from 9 events showing the low gamma-zein/low alpha-zein/high corn legumin/high alpha-globulin/high 18 kD delta-zein/high beta-zein phenotype ("altered seed protein phenotype") were analyzed by SDS-PAGE for their seed protein phenotypes. Each event was sorted into two batches of 50 seeds each. The seed weights of each pair of batches were determined and showed no significant difference.

Meal was prepared from each sample (nine events, two batches each) and analyzed for its amino acid composition and protein content. For all events, the average protein content was reduced in the altered seed protein phenotype samples by 10% (dry weight), the lysine content was increased by >70% (dry weight) and the tryptophane content was increased by >60% (dry weight).

Meal was prepared from each of the pairs of batches of six events and analyzed for EDDM at the 6 hr. time point. The altered seed protein phenotype samples showed, on average, an improvement of 9.8 percentage points compared to the segregating control samples.

In the segregating control, an overnight soak in 10 mM of dithiothreietol (DTT), improved digestibility by 3.7 percentage units. In transgenic corn there was no additional improvement in digestibility. The effect of DTT on digestibility mimics the impact of the suppression of gamma-zein on grain digestibility. Thus the difference between the improved digestibility of 3.7 percentage units due to DTT treatment and the improved digestibility in the altered seed protein phenotype samples (9.8 percentage units) was an indicator for the added digestibility improvement to EDDM digestibility attributable to the suppression of alpha-zein proteins, overexpression of alpha-globulin and overexpression of corn legumin. This demonstrated that digestibility of the transgenic, altered seed protein phenotype, grains improved beyond that attainable by only removing digestion-limiting disulfide bonds (associated with gamma-zein), or by only removing alpha-zeins or by only over-expressing either alpha-globulin or corn legumin as single transgene events. The digestibility trait of the combination of co-suppression and over-expression cassettes was partially additive to digestibility effects obtained with the non-combined, co-suppression or over-expression cassettes in independent transgenic events.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for making a genetically modified maize plant with grain having increased energy availability compared to the corresponding unmodified plant and a hard vitreous endosperm, the method comprising:
   a) introducing into a maize plant cell an expression cassette with means for stably decreasing the level of a gamma-zein selected from the group consisting of 27 kD and 50 kD gamma-zein, wherein the means for stable decrease is co-suppression, or homology-dependent gene silencing targeting a gamma-zein selected from the group consisting of 27 kD and 50 kD gamma-zein;
   b) regenerating a genetically modified maize plant from the cell; and
   c) selecting for a genetically modified maize plant with grain having increased energy availability and a hard vitreous endosperm, wherein the increased energy availability and hard vitreous endosperm being due the stably decreased level of a gamma-zein selected from the group consisting of 16 kD, 27 kD, and 50 kD gamma-zein.

2. The method of claim 1, further comprising obtaining genetically modified progeny plants of one or more generations with increased energy availability.

3. The method of claim 1, further comprising introducing into a maize plant cell an expression cassette with means for stably increasing the level of a cereal plant globulin selected from the group consisting of an alpha-globulin and a legumin1 protein.

4. The method of claim 2, wherein the progeny plants are obtained by selfing, crossing with another plant or clonal propagation.

5. The method of claim 1, further comprising processing the grain or feeding the grain to animals.

6. A method for making a genetically modified maize plant with grain having increased energy availability compared to the corresponding unmodified plant and a hard vitreous endosperm, the method comprising:
   a) transforming a maize cell with an expression cassette comprising an isolated nucleic acid selected from the group consisting of:
      i) a polynucleotide of at least 21 contiguous nucleotides of the complement of SEQ ID NO: 1, wherein the polynucleotide encodes an RNA that mediates RNA interference of an mRNA encoding the polypeptide set forth in SEQ ID NO: 2; and
      ii) a DNA sequence comprising the polynucleotide of (i), and the complement of the polynucleotide of (i), wherein the transcript encoded by the DNA sequence is capable of forming a double stranded RNA;
   b) regenerating a genetically modified maize plant from the maize cell; and c) selecting for a genetically modified maize plant with grain having increased energy availability and a hard vitreous endosperm.

7. The method of claim 1, further comprising introducing into a maize plant cell an expression cassette with means for stably decreasing the level of alpha zein.

8. The method of claim 1 or 7, further comprising introducing into a maize plant cell an expression cassette with means for stably increasing the level of a zein selected from the group consisting of 15 kD beta zein and 18 kD delta zein.

9. The method of claim 3, further comprising introducing into a maize plant cell an expression cassette with means for stably increasing the level of zein selected from the group consisting of 15 kD beta zein and 18 kD delta zein.

* * * * *

SEQUENCE LISTING

```
<160> NUMBER OF SEQ ID NOS: 27

<210> SEQ ID NO 1
<211> LENGTH: 1129
<212> TYPE: DNA
<213> ORGANISM: Zea mays
<220> FEATURE:
<221> NAME/KEY: CDS
<222> LOCATION: (120)...(1004)
<223> OTHER INFORMATION: 50 kD gamma-zein prolamin/PTA 2272

<400> SEQUENCE: 1
gtgtatttgc actcatgcat cacaaaacat ccttctatca gtaccatcaa tcatcattca        60
tcttagtagt ataggcacca aatcaaatct gcaacatcaa ttatctaact ccaaaaacc        119 atg aag ctg gtg ctt gtg gtt ctt gct ttc att gct tta gta tca agt        167
Met Lys Leu Val Leu Val Val Leu Ala Phe Ile Ala Leu Val Ser Ser
 1               5                  10                  15 gtt tct tgt aca cag aca ggc ggc tgc agc tgt ggt caa caa caa agc        215
Val Ser Cys Thr Gln Thr Gly Gly Cys Ser Cys Gly Gln Gln Gln Ser
             20                  25                  30 cat gag cag caa cat cat cca caa caa cat cat cca caa aaa caa caa        263
His Glu Gln Gln His His Pro Gln Gln His His Pro Gln Lys Gln Gln
         35                  40                  45 cat caa cca cca cca caa cat cac cag cag caa cac caa caa caa        311
His Gln Pro Pro Pro Gln His His Gln Gln Gln His Gln Gln Gln
     50                  55                  60 caa gtt cac atg caa cca caa aaa cat cag caa caa caa gaa gtt cat        359
```

```
Gln Val His Met Gln Pro Gln Lys His Gln Gln Gln Glu Val His
 65                  70                  75                  80 gtt caa caa caa caa caa caa ccg cag cac caa caa caa caa caa        407
Val Gln Gln Gln Gln Gln Gln Pro Gln His Gln Gln Gln Gln Gln
                 85                  90                  95 caa cag cac caa caa caa cat caa tgt gaa ggc caa caa cat cac        455
Gln Gln His Gln Gln Gln His Gln Cys Glu Gly Gln Gln His His
            100                 105                 110 caa caa tca caa ggc cat gtg caa caa cac gaa cag agc cat gag caa    503
Gln Gln Ser Gln Gly His Val Gln Gln His Glu Gln Ser His Glu Gln
        115                 120                 125 cac caa gga cag agc cat gag caa caa cat caa caa caa ttc cag ggt    551
His Gln Gly Gln Ser His Glu Gln Gln His Gln Gln Gln Phe Gln Gly
    130                 135                 140 cat gac aag cag caa caa cca caa cag cct cag caa tat cag cag ggc    599
His Asp Lys Gln Gln Gln Pro Gln Gln Pro Gln Gln Tyr Gln Gln Gly
145                 150                 155                 160 cag gaa aaa tca caa cag caa caa tgt cat tgc cag gag cag caa cag    647
Gln Glu Lys Ser Gln Gln Gln Gln Cys His Cys Gln Glu Gln Gln Gln
                165                 170                 175 act aca agg tgc agc tat aac tac tat agc agt agc tca aat cta aaa    695
Thr Thr Arg Cys Ser Tyr Asn Tyr Tyr Ser Ser Ser Ser Asn Leu Lys
            180                 185                 190 aat tgt cat gaa ttc cta agg cag cag tgc agc cct ttg gta atg cct    743
Asn Cys His Glu Phe Leu Arg Gln Gln Cys Ser Pro Leu Val Met Pro
        195                 200                 205 ttt ctc caa tca cgt ttg ata caa cca agt agc tgc cag gta ttg cag    791
Phe Leu Gln Ser Arg Leu Ile Gln Pro Ser Ser Cys Gln Val Leu Gln
    210                 215                 220 caa caa tgt tgt cat gat ctt agg cag att gag cca caa tac att cac    839
Gln Gln Cys Cys His Asp Leu Arg Gln Ile Glu Pro Gln Tyr Ile His
225                 230                 235                 240 caa gca atc tac aac atg gtt caa tcc ata atc cag gag gag caa caa    887
Gln Ala Ile Tyr Asn Met Val Gln Ser Ile Ile Gln Glu Glu Gln Gln
                245                 250                 255 caa caa cca tgt gag tta tgt gga tct caa caa gct act cca aag tgc    935
Gln Gln Pro Cys Glu Leu Cys Gly Ser Gln Gln Ala Thr Pro Lys Cys
            260                 265                 270 ggt ggc aat ctt gac agc agc aca ata cct acc atc aat gtg cgg ctt    983
Gly Gly Asn Leu Asp Ser Ser Thr Ile Pro Thr Ile Asn Val Arg Leu
        275                 280                 285 gta cca ctc ata cta cca aaa taatccatgc agcagcaatg acattagtgg      1034
Val Pro Leu Ile Leu Pro Lys
    290                 295 tgtttgcaat tgaagaattg tgtctaccta gccgttatac tcatataacg gtgttaagca 1094 ataaagtacc atacattatg atgttaaaaa aaaaa                           1129

<210> SEQ ID NO 2
<211> LENGTH: 295
<212> TYPE: PRT
<213> ORGANISM: Zea mays

<400> SEQUENCE: 2

Met Lys Leu Val Leu Val Val Leu Ala Phe Ile Ala Leu Val Ser Ser
 1               5                   10                  15

Val Ser Cys Thr Gln Thr Gly Gly Cys Ser Cys Gly Gln Gln Gln Ser
                20                  25                  30

His Glu Gln Gln His His Pro Gln Gln His His Pro Gln Lys Gln Gln
            35                  40                  45
```

-continued

```
His Gln Pro Pro Pro Gln His His Gln Gln Gln Gln His Gln Gln Gln
 50                  55                  60

Gln Val His Met Gln Pro Gln Lys His Gln Gln Gln Gln Glu Val His
 65                  70                  75                  80

Val Gln Gln Gln Gln Gln Gln Pro Gln His Gln Gln Gln Gln Gln Gln
                 85                  90                  95

Gln Gln His Gln Gln Gln His Gln Cys Glu Gly Gln Gln Gln His His
            100                 105                 110

Gln Gln Ser Gln Gly His Val Gln Gln His Glu Gln Ser His Glu Gln
        115                 120                 125

His Gln Gly Gln Ser His Glu Gln Gln His Gln Gln Phe Gln Gly
    130                 135                 140

His Asp Lys Gln Gln Pro Gln Gln Pro Gln Gln Tyr Gln Gln Gly
145                 150                 155                 160

Gln Glu Lys Ser Gln Gln Gln Cys His Cys Gln Glu Gln Gln
                165                 170                 175

Thr Thr Arg Cys Ser Tyr Asn Tyr Ser Ser Ser Asn Leu Lys
            180                 185                 190

Asn Cys His Glu Phe Leu Arg Gln Gln Cys Ser Pro Leu Val Met Pro
    195                 200                 205

Phe Leu Gln Ser Arg Leu Ile Gln Pro Ser Ser Cys Gln Val Leu Gln
    210                 215                 220

Gln Gln Cys Cys His Asp Leu Arg Gln Ile Glu Pro Gln Tyr Ile His
225                 230                 235                 240

Gln Ala Ile Tyr Asn Met Val Gln Ser Ile Gln Glu Glu Gln Gln
                245                 250                 255

Gln Gln Pro Cys Glu Leu Cys Gly Ser Gln Gln Ala Thr Pro Lys Cys
            260                 265                 270

Gly Gly Asn Leu Asp Ser Ser Thr Ile Pro Thr Ile Asn Val Arg Leu
        275                 280                 285

Val Pro Leu Ile Leu Pro Lys
    290                 295

<210> SEQ ID NO 3
<211> LENGTH: 950
<212> TYPE: DNA
<213> ORGANISM: Zea mays
<220> FEATURE:
<221> NAME/KEY: CDS
<222> LOCATION: (111)...(728)
<223> OTHER INFORMATION: 18 kD alpha-globulin/PTA 2274

<400> SEQUENCE: 3
aaaaaaaccc cctcgtcgat caccaccaaa gaacacagta actagcagct agcacatcaa      60
acaagtggcg acagacaaag atttgtgagg gtgatccgcg ctgagaagag atg gct       116
                                                         Met Ala
                                                           1 aag atc gcc gcg gcg gcg gcg gcg gcg ctg tgc ttc gcg gcc ctg gtg    164
Lys Ile Ala Ala Ala Ala Ala Ala Ala Leu Cys Phe Ala Ala Leu Val
        5                  10                  15 gcc gtg gcc gtc tgc caa ggc gag gtc gag cgg cag agg ctc agg gac    212
Ala Val Ala Val Cys Gln Gly Glu Val Glu Arg Gln Arg Leu Arg Asp
     20                  25                  30 ctg cag tgc tgg cag gag gtc cag gag agc ccg ctc gac gcg tgc cgc    260
Leu Gln Cys Trp Gln Glu Val Gln Glu Ser Pro Leu Asp Ala Cys Arg
 35                  40                  45                  50 cag gtc ctc gac cgg cag cta acc ggc ggc ggc ggc ggc ggc ggc gtt    308
Gln Val Leu Asp Arg Gln Leu Thr Gly Gly Gly Gly Gly Gly Gly Val
```

```
                         55                      60                      65
ggc ccg ttc cgg tgg ggc acc ggg ctc cgg atg cgg tgc tgc cag cag       356
Gly Pro Phe Arg Trp Gly Thr Gly Leu Arg Met Arg Cys Cys Gln Gln
            70                      75                      80 ctc cag gac gtg agc cgc gag tgc cgc tgc gcc gcc atc cgg agc atg       404
Leu Gln Asp Val Ser Arg Glu Cys Arg Cys Ala Ala Ile Arg Ser Met
        85                      90                      95 gtc agg ggc tac gag gag gcc atg ccg ccg ctg gag aaa ggc tgg tgg       452
Val Arg Gly Tyr Glu Glu Ala Met Pro Pro Leu Glu Lys Gly Trp Trp
    100                     105                     110 cca tgg ggg cgg cag cag cag ccg ccg cag gga gga gga gga gga           500
Pro Trp Gly Arg Gln Gln Gln Pro Pro Gln Gly Gly Gly Gly Gly
115                     120                     125                 130 cag ggg ggc tac tac tac ccc tgc agc cgg cca gga gag gga tac ggc       548
Gln Gly Gly Tyr Tyr Tyr Pro Cys Ser Arg Pro Gly Glu Gly Tyr Gly
            135                     140                     145 tac ggt cag ggt ggc cag cgg cag atg tat cca ccg tgt cgt ccc ggc       596
Tyr Gly Gln Gly Gly Gln Arg Gln Met Tyr Pro Pro Cys Arg Pro Gly
        150                     155                     160 acc acc ggc ggc ggg cca agg atc ggc cgc gtg agg ctt acg aag gcc       644
Thr Thr Gly Gly Gly Pro Arg Ile Gly Arg Val Arg Leu Thr Lys Ala
    165                     170                     175 cgg gag tac gcc gcg ggg ttg ccg atg atg tgc cgg ctg tcg gag ccc       692
Arg Glu Tyr Ala Ala Gly Leu Pro Met Met Cys Arg Leu Ser Glu Pro
180                     185                     190 cag gag tgc agc atc ttc tcc ggc ggc gac cag tac tagctaccat            738
Gln Glu Cys Ser Ile Phe Ser Gly Gly Asp Gln Tyr
195                     200                     205 ggttaaagcg agtcggcgcg aggtgcaaga cgcagcatgt gtactgtgcg cgtgcaaatc     798
cagaatgacg tagctctgac gtgggctcgc aatattgtcg cgtgttcgtt acaataatga     858
taataactat gaggaataaa tatgggaatg ttgccagata gtactggcgc cggttcttca     918
aaaaaaaaaa aaaaaaaaaa aaaaaaaaaa aa                                    950

<210> SEQ ID NO 4
<211> LENGTH: 206
<212> TYPE: PRT
<213> ORGANISM: Zea mays

<400> SEQUENCE: 4

Met Ala Lys Ile Ala Ala Ala Ala Ala Ala Leu Cys Phe Ala Ala
 1               5                  10                  15

Leu Val Ala Val Ala Val Cys Gln Gly Glu Val Glu Arg Gln Arg Leu
                20                  25                  30

Arg Asp Leu Gln Cys Trp Gln Glu Val Gln Glu Ser Pro Leu Asp Ala
            35                  40                  45

Cys Arg Gln Val Leu Asp Arg Gln Leu Thr Gly Gly Gly Gly Gly
        50                  55                  60

Gly Val Gly Pro Phe Arg Trp Gly Thr Gly Leu Arg Met Arg Cys Cys
 65                  70                  75                  80

Gln Gln Leu Gln Asp Val Ser Arg Glu Cys Arg Cys Ala Ala Ile Arg
                85                  90                  95

Ser Met Val Arg Gly Tyr Glu Glu Ala Met Pro Pro Leu Glu Lys Gly
            100                 105                 110

Trp Trp Pro Trp Gly Arg Gln Gln Gln Pro Pro Gln Gly Gly Gly
        115                 120                 125

Gly Gly Gln Gly Gly Tyr Tyr Tyr Pro Cys Ser Arg Pro Gly Glu Gly
    130                 135                 140
```

```
Tyr Gly Tyr Gly Gln Gly Gly Gln Arg Gln Met Tyr Pro Pro Cys Arg
145                 150                 155                 160

Pro Gly Thr Thr Gly Gly Pro Arg Ile Gly Arg Val Arg Leu Thr
            165                 170                 175

Lys Ala Arg Glu Tyr Ala Ala Gly Leu Pro Met Met Cys Arg Leu Ser
        180                 185                 190

Glu Pro Gln Glu Cys Ser Ile Phe Ser Gly Gly Asp Gln Tyr
        195                 200                 205

<210> SEQ ID NO 5
<211> LENGTH: 1679
<212> TYPE: DNA
<213> ORGANISM: Zea mays
<220> FEATURE:
<221> NAME/KEY: CDS
<222> LOCATION: (34)...(1485)
<223> OTHER INFORMATION: 50 kD legumin-1 prolamin/PTA 2273

<400> SEQUENCE: 5
gcacgaggag cgagcgagca gaggcagcgc aca atg gcg gcg gca ata gta ctc         54
                                     Met Ala Ala Ala Ile Val Leu
                                       1               5 tcc ggc cag gtg cgg ccg ctt ccc tcg tcg ctg ccc ctg tcc ctg ctg        102
Ser Gly Gln Val Arg Pro Leu Pro Ser Ser Leu Pro Leu Ser Leu Leu
       10                  15                  20 ctg ctc ctc ctc ctg tgc tgc tcc ggc acc tcg tgg gga tgg agc acg        150
Leu Leu Leu Leu Leu Cys Cys Ser Gly Thr Ser Trp Gly Trp Ser Thr
   25                  30                  35 tcc cgg gga gga gcc gcc agg gag tgc ggc ttc gat ggc aag ctg gag        198
Ser Arg Gly Gly Ala Ala Arg Glu Cys Gly Phe Asp Gly Lys Leu Glu
40                  45                  50                  55 gcc ctg gag ccg cgc cac aag gtg cag tct gag gcc ggc tcc gtc cag        246
Ala Leu Glu Pro Arg His Lys Val Gln Ser Glu Ala Gly Ser Val Gln
                60                  65                  70 tac ttc agc cgg ttc aac gaa gcc gac cgg gag ctc acc tgc gcc ggc        294
Tyr Phe Ser Arg Phe Asn Glu Ala Asp Arg Glu Leu Thr Cys Ala Gly
            75                  80                  85 atc ttc gcc gtc cgc gtc gtc gtc gac gcc atg ggc ctc ctg ctc cct        342
Ile Phe Ala Val Arg Val Val Val Asp Ala Met Gly Leu Leu Leu Pro
        90                  95                 100 cga tac tcc aac gtc cat tcg ctt gtc tac atc gtc caa ggg aga ggg        390
Arg Tyr Ser Asn Val His Ser Leu Val Tyr Ile Val Gln Gly Arg Gly
    105                 110                 115 atc att ggg ttc tcg ttt ccg gga tgc caa gag gag acc cag cag cag        438
Ile Ile Gly Phe Ser Phe Pro Gly Cys Gln Glu Glu Thr Gln Gln Gln
120                 125                 130                 135 cag tat gga tac gga tat gga tat gga cac cat cac cag cat gac            486
Gln Tyr Gly Tyr Gly Tyr Gly Tyr Gly His His His Gln His Asp
                140                 145                 150 cac cac aag atc cac cga ttc gag cag ggc gac gtg gtg gcc atg ccg        534
His His Lys Ile His Arg Phe Glu Gln Gly Asp Val Val Ala Met Pro
            155                 160                 165 gcc ggc gcc cag cac tgg ctg tac aac gac ggc gac gcg ccg ctt gtg        582
Ala Gly Ala Gln His Trp Leu Tyr Asn Asp Gly Asp Ala Pro Leu Val
        170                 175                 180 gcg gtc tac gtc ttc gac gag aac aac aac atc aac cag ctc gag cct        630
Ala Val Tyr Val Phe Asp Glu Asn Asn Asn Ile Asn Gln Leu Glu Pro
    185                 190                 195 tcc atg agg aaa ttt ttg ctg gct ggg ggc ttc agc aag ggg cag ccc        678
Ser Met Arg Lys Phe Leu Leu Ala Gly Gly Phe Ser Lys Gly Gln Pro
200                 205                 210                 215
```

```
cac ttc gcc gag aac atc ttc aaa ggg atc gac gcc cgg ttc ctg agc       726
His Phe Ala Glu Asn Ile Phe Lys Gly Ile Asp Ala Arg Phe Leu Ser
                220                 225                 230 gaa gcc ctg ggc gtc agc atg cac gtc gcc gag aag ctg cag agc cgg       774
Glu Ala Leu Gly Val Ser Met His Val Ala Glu Lys Leu Gln Ser Arg
            235                 240                 245 cgt gac cag cga ggc gag atc gtc cgc gtg gag ccg gag cac ggc ttt       822
Arg Asp Gln Arg Gly Glu Ile Val Arg Val Glu Pro Glu His Gly Phe
        250                 255                 260 cac cag ctg aat ccg tcg ccg tcg tcg tcg ttt tcg ttc cca tcg           870
His Gln Leu Asn Pro Ser Pro Ser Ser Ser Phe Ser Phe Pro Ser
    265                 270                 275 tca caa gtc cag tac caa acg tgc cag cgc gac gtc gac agg cac aac       918
Ser Gln Val Gln Tyr Gln Thr Cys Gln Arg Asp Val Asp Arg His Asn
280                 285                 290                 295 gtc tgc gcc atg gag gtg agg cac agc gtc gaa cgg ctg gac cag gcc       966
Val Cys Ala Met Glu Val Arg His Ser Val Glu Arg Leu Asp Gln Ala
                300                 305                 310 gac gtc tac agc cct ggg gct ggg agg atc aca cgc ctc acc agc cac      1014
Asp Val Tyr Ser Pro Gly Ala Gly Arg Ile Thr Arg Leu Thr Ser His
            315                 320                 325 aag ttc ccc gtc ctc aac ctc gta cag atg agc gcg gtg cgg gta gac      1062
Lys Phe Pro Val Leu Asn Leu Val Gln Met Ser Ala Val Arg Val Asp
        330                 335                 340 ctg tac cag gac gcc atc atg tcg ccg ttc tgg aac ttc aac gcc cac      1110
Leu Tyr Gln Asp Ala Ile Met Ser Pro Phe Trp Asn Phe Asn Ala His
    345                 350                 355 agc gcc atg tac ggc atc agg ggc agt gca agg gtc cag gtc gcc agc      1158
Ser Ala Met Tyr Gly Ile Arg Gly Ser Ala Arg Val Gln Val Ala Ser
360                 365                 370                 375 gac aac ggg acc acg gtg ttc gac gac gtg ctc cgt gcg ggg cag ctg      1206
Asp Asn Gly Thr Thr Val Phe Asp Asp Val Leu Arg Ala Gly Gln Leu
                380                 385                 390 ctc atc gta ccc cag ggc tac ctc gtc gcc acc aag gcg cag gga gaa      1254
Leu Ile Val Pro Gln Gly Tyr Leu Val Ala Thr Lys Ala Gln Gly Glu
            395                 400                 405 ggc ttc cag tac atc gcc ttc gag acg aac cct gac acc atg gtc agc      1302
Gly Phe Gln Tyr Ile Ala Phe Glu Thr Asn Pro Asp Thr Met Val Ser
        410                 415                 420 cac gtc gcc ggg aag aac tcc gtc ctg agc gac ttg ccg gcc gcc gtc      1350
His Val Ala Gly Lys Asn Ser Val Leu Ser Asp Leu Pro Ala Ala Val
    425                 430                 435 atc gcc agc tcg tat gcc atc tcc atg gag gaa gct gca gag ctc aag      1398
Ile Ala Ser Ser Tyr Ala Ile Ser Met Glu Glu Ala Ala Glu Leu Lys
440                 445                 450                 455 aac ggt agg aag cat gag ctg gct gtg ctt act cct gct ggc agt ggc      1446
Asn Gly Arg Lys His Glu Leu Ala Val Leu Thr Pro Ala Gly Ser Gly
                460                 465                 470 agc tac caa caa ggt caa gct ggc agc gcc caa cag tag gcacaacctc       1495
Ser Tyr Gln Gln Gly Gln Ala Gly Ser Ala Gln Gln
            475                 480 agagtgatct gcctgaataa gtactcgtag actgtaataa ttaaacaaag cttgctcatg    1555
gttaaactgc gtgttgatta gtctttcaac tacatagctc taaagttttt gatacaccga    1615
gtgatttgcc agggaaaaaa tgagcagatt gttgtaagca aaaaaaaaaa aaaaaaaaaa    1675
aaaa                                                                 1679

<210> SEQ ID NO 6
<211> LENGTH: 483
```

<212> TYPE: PRT
<213> ORGANISM: Zea mays

<400> SEQUENCE: 6

Met Ala Ala Ala Ile Val Leu Ser Gly Gln Val Arg Pro Leu Pro Ser
1               5                   10                  15

Ser Leu Pro Leu Ser Leu Leu Leu Leu Leu Cys Cys Ser Gly
        20                  25                  30

Thr Ser Trp Gly Trp Ser Thr Ser Arg Gly Gly Ala Ala Arg Glu Cys
        35                  40                  45

Gly Phe Asp Gly Lys Leu Glu Ala Leu Glu Pro Arg His Lys Val Gln
        50                  55                  60

Ser Glu Ala Gly Ser Val Gln Tyr Phe Ser Arg Phe Asn Glu Ala Asp
65                  70                  75                  80

Arg Glu Leu Thr Cys Ala Gly Ile Phe Ala Val Arg Val Val Val Asp
                85                  90                  95

Ala Met Gly Leu Leu Pro Arg Tyr Ser Asn Val His Ser Leu Val
                100                 105                 110

Tyr Ile Val Gln Gly Arg Gly Ile Ile Gly Phe Ser Phe Pro Gly Cys
        115                 120                 125

Gln Glu Glu Thr Gln Gln Gln Tyr Gly Tyr Gly Tyr Gly Tyr Gly
        130                 135                 140

His His His His Gln His Asp His His Lys Ile His Arg Phe Glu Gln
145                 150                 155                 160

Gly Asp Val Val Ala Met Pro Ala Gly Ala Gln His Trp Leu Tyr Asn
                165                 170                 175

Asp Gly Asp Ala Pro Leu Val Ala Val Tyr Val Phe Asp Glu Asn Asn
                180                 185                 190

Asn Ile Asn Gln Leu Glu Pro Ser Met Arg Lys Phe Leu Leu Ala Gly
        195                 200                 205

Gly Phe Ser Lys Gly Gln Pro His Phe Ala Glu Asn Ile Phe Lys Gly
210                 215                 220

Ile Asp Ala Arg Phe Leu Ser Glu Ala Leu Gly Val Ser Met His Val
225                 230                 235                 240

Ala Glu Lys Leu Gln Ser Arg Arg Asp Gln Arg Gly Glu Ile Val Arg
                245                 250                 255

Val Glu Pro Glu His Gly Phe His Gln Leu Asn Pro Ser Pro Ser Ser
                260                 265                 270

Ser Ser Phe Ser Phe Pro Ser Ser Gln Val Gln Tyr Gln Thr Cys Gln
        275                 280                 285

Arg Asp Val Asp Arg His Asn Val Cys Ala Met Glu Val Arg His Ser
290                 295                 300

Val Glu Arg Leu Asp Gln Ala Asp Val Tyr Ser Pro Gly Ala Gly Arg
305                 310                 315                 320

Ile Thr Arg Leu Thr Ser His Lys Phe Pro Val Leu Asn Leu Val Gln
                325                 330                 335

Met Ser Ala Val Arg Val Asp Leu Tyr Gln Asp Ala Ile Met Ser Pro
                340                 345                 350

Phe Trp Asn Phe Asn Ala His Ser Ala Met Tyr Gly Ile Arg Gly Ser
        355                 360                 365

Ala Arg Val Gln Val Ala Ser Asp Asn Gly Thr Thr Val Phe Asp Asp
        370                 375                 380

Val Leu Arg Ala Gly Gln Leu Leu Ile Val Pro Gln Gly Tyr Leu Val
385                 390                 395                 400

-continued

```
Ala Thr Lys Ala Gln Gly Glu Gly Phe Gln Tyr Ile Ala Phe Glu Thr
            405                 410                 415

Asn Pro Asp Thr Met Val Ser His Val Ala Gly Lys Asn Ser Val Leu
        420                 425                 430

Ser Asp Leu Pro Ala Ala Val Ile Ala Ser Ser Tyr Ala Ile Ser Met
    435                 440                 445

Glu Glu Ala Ala Glu Leu Lys Asn Gly Arg Lys His Glu Leu Ala Val
450                 455                 460

Leu Thr Pro Ala Gly Ser Gly Ser Tyr Gln Gln Gly Gln Ala Gly Ser
465                 470                 475                 480

Ala Gln Gln

<210> SEQ ID NO 7
<211> LENGTH: 324
<212> TYPE: DNA
<213> ORGANISM: Zea mays
<220> FEATURE:
<221> NAME/KEY: allele
<222> LOCATION: (1)...(324)
<223> OTHER INFORMATION: 50kD gamma-zein, B73 partial

<400> SEQUENCE: 7
ccagcagcag caacaccaac aacaacaagt tcacatgcaa ccacaaaaac atcagcaaca      60
acaagaagtt catgttcaac aacaacaaca acaaccgcag caccaacaac aacaacaaca    120
acaacagcac caacaacaac atcaatgtga aggccaacaa caacatcacc aacaatcaca    180
aggccatgtg caacaacacg aacagagcca tgagcaacac caaggacaga gccatgagca    240
acaacatcaa caacaattcc agggtcatga caagcagcaa caaccacaac agcctcagca    300
atatcagcag ggccaggaaa aatc                                          324

<210> SEQ ID NO 8
<211> LENGTH: 321
<212> TYPE: DNA
<213> ORGANISM: Zea mays
<220> FEATURE:
<221> NAME/KEY: allele
<222> LOCATION: (1)...(321)
<223> OTHER INFORMATION: 50kD gamma-zein, Mo17 partial

<400> SEQUENCE: 8
ccagcagcag caacaccaac aacaacaagt tcacatgcaa ccacaaaaac atcagcaaca      60
acaagaagtt catgttcaac aacaacaaca acaaccgcag caccaacaac aacaacaaca    120
acagcaccaa caacaacatc aatgtgaagg ccaacaacaa catcaccaac aatcacaagg    180
ccatgtgcaa caacacgaac agagccatga gcaacaccaa ggacagagcc atgagcaaca    240
acatcaacaa caattccagg gtcatgacaa gcagcaacaa ccacacagc ctcagcaata    300 tcagcagggc caggaaaaat c                                             321

<210> SEQ ID NO 9
<211> LENGTH: 561
<212> TYPE: DNA
<213> ORGANISM: Zea mays
<220> FEATURE:
<221> NAME/KEY: allele
<222> LOCATION: (1)...(561)
<223> OTHER INFORMATION: 18 kD alpha-globulin, B73, partial

<400> SEQUENCE: 9
aattcgccct tgtcattctg gatttgcacg cgcacagtac acatgctgcg tcttgcacgt      60
cgcgccgact cgctttaacc atggtagcta gtactggtcg ccgccggaga agatgctgca    120
```

```
ctcctggggc tccgacagcc ggcacatcat cggcaacccc gcggcgtact cccgggcctt    180
cgtaagcctc acgcggccga tccttggccc gccgccggtg gtgccgggac gacacggtgg    240
atacatctgc cgctggccac cctgaccgta gccgtatccc tctcctggcc ggctgcaggg    300
gtagtagtag ccccctgtc ctcctcctcc tccctgcggc ggcggctgct gctgccgccc     360
ccatggccac cagcctttct ccagcggcgg catggcctcc tcgtagcccc tgaccatgct    420
ccggatggcg gcgcagcggc actcgcggct cacgtcctgg agctgctggc agcaccgcat    480
ccggagcccg gtgccccacc ggaacgggcc aacgccgccg ccgccgccgc cgccggttag    540
ctgccggtcg aggaaagggc g                                              561

<210> SEQ ID NO 10
<211> LENGTH: 537
<212> TYPE: DNA
<213> ORGANISM: Zea mays
<220> FEATURE:
<221> NAME/KEY: allele
<222> LOCATION: (1)...(537)
<223> OTHER INFORMATION: 18 kD alpha-globulin, Mo17 partial

<400> SEQUENCE: 10
aattcgccct tgtcattctg gatttgcacg cgcacagtac acatgctgcg ccttgcacgt     60
cgcgccgact cactctttt tttttaaccc tggtagctag tactggtcgc cgccggagaa    120
gatgctgcac tcctggggct ccgacagccg gcacatcatc ggcaaccccg cggcgtactc    180
ccgggccttc gtaagcctca cgcggccgat ccttggcccg gtggtgccgg gacgacacgg    240
tggatacatc tgcgtttggt atccctctcc tgcccggctg caggggtagt agtagccccc    300
ctgtcctcct cctcctccct gcggcggcgg ctgctgctgc cgcccccatg ccaccagcc    360 tttctccaga ggcggcatgg cctcctcgta gcccctgacc atgctccgga tggcggcgca    420
gcggcactcg cggctcacgt cctggagctg ctggcagcac cgcatccgga gcccggtgcc    480
ccaccggaac gggccgccga cgccgccgcc ggttagctgc cggtcgagga aagggcg      537

<210> SEQ ID NO 11
<211> LENGTH: 23
<212> TYPE: DNA
<213> ORGANISM: Artificial Sequence
<220> FEATURE:
<223> OTHER INFORMATION: primer 170

<400> SEQUENCE: 11
agcgccacct ccacgcatac aag                                            23

<210> SEQ ID NO 12
<211> LENGTH: 26
<212> TYPE: DNA
<213> ORGANISM: Artificial Sequence
<220> FEATURE:
<223> OTHER INFORMATION: primer 296

<400> SEQUENCE: 12
ctagctagcc agcggctata ctacag                                         26

<210> SEQ ID NO 13
<211> LENGTH: 32
<212> TYPE: DNA
<213> ORGANISM: Artificial Sequence
<220> FEATURE:
<223> OTHER INFORMATION: Mu primer 9242

<400> SEQUENCE: 13
```

-continued

```
agagaagcca acgccawcgc ctcyatttcg tc                                          32

<210> SEQ ID NO 14
<211> LENGTH: 28
<212> TYPE: DNA
<213> ORGANISM: Artificial Sequence
<220> FEATURE:
<223> OTHER INFORMATION: primer 008

<400> SEQUENCE: 14
gtcgaaccag aacagcatga agatggtc                                               28

<210> SEQ ID NO 15
<211> LENGTH: 26
<212> TYPE: DNA
<213> ORGANISM: Artificial Sequence
<220> FEATURE:
<223> OTHER INFORMATION: primer 009

<400> SEQUENCE: 15
gtactggtac tggtagagtc caccca                                                 26

<210> SEQ ID NO 16
<211> LENGTH: 1704
<212> TYPE: DNA
<213> ORGANISM: Artificial Sequence
<220> FEATURE:
<223> OTHER INFORMATION: chimeric alpha-zein construct
<221> NAME/KEY: CDS
<222> LOCATION: (1)...(563)
<223> OTHER INFORMATION: 19kD alpha-zein D1
<221> NAME/KEY: CDS
<222> LOCATION: (564)...(1101)
<223> OTHER INFORMATION: 19kD alpha-zein B1
<221> NAME/KEY: CDS
<222> LOCATION: (1102)...(1704)
<223> OTHER INFORMATION: 22kD alpha-zein

<400> SEQUENCE: 16 atg gta caa gag gcc atc caa gca agc atc tta cgg tca tta gca tta      48
Met Val Gln Glu Ala Ile Gln Ala Ser Ile Leu Arg Ser Leu Ala Leu
 1               5                  10                  15 acc ctc caa caa cca tat gct cta ttg caa cag cca tcc tta gtg cat      96
Thr Leu Gln Gln Pro Tyr Ala Leu Leu Gln Gln Pro Ser Leu Val His
             20                  25                  30 ctg tat ctc caa aga atc gcg gca caa caa cta caa caa cag ttg cta     144
Leu Tyr Leu Gln Arg Ile Ala Ala Gln Gln Leu Gln Gln Gln Leu Leu
         35                  40                  45 cca aca atc aat caa gta gtt gca gcg aac ctt gct gct tac ctc cag     192
Pro Thr Ile Asn Gln Val Val Ala Ala Asn Leu Ala Ala Tyr Leu Gln
     50                  55                  60 caa caa cag ttt ctt cca ttc aat caa cta gct ggg gtg aac cct gct     240
Gln Gln Gln Phe Leu Pro Phe Asn Gln Leu Ala Gly Val Asn Pro Ala
 65                  70                  75                  80 atc tac ttg cag gca caa cag cta cta cca ttt aac caa ctt gtc ggg     288
Ile Tyr Leu Gln Ala Gln Gln Leu Leu Pro Phe Asn Gln Leu Val Gly
                 85                  90                  95 agc cct tat gcc ttc tta ctg caa caa cag ctt ctg cca ttc cat ctg     336
Ser Pro Tyr Ala Phe Leu Leu Gln Gln Gln Leu Leu Pro Phe His Leu
            100                 105                 110 caa gct gtg gca aac att gtt gct ttc ttg aga caa caa cat ttg ttg     384
Gln Ala Val Ala Asn Ile Val Ala Phe Leu Arg Gln Gln His Leu Leu
        115                 120                 125 cca ttt tac cca caa gtt gtg gga aac att aat gcc ttc ttg caa cag     432
Pro Phe Tyr Pro Gln Val Val Gly Asn Ile Asn Ala Phe Leu Gln Gln
```

```
              130                 135                 140
caa caa ttg cta cca ttc tac cca cag aat gtg gca aac att gtt gcc    480
Gln Gln Leu Leu Pro Phe Tyr Pro Gln Asn Val Ala Asn Ile Val Ala
145                 150                 155                 160 ttc tta caa caa caa caa ttg ctg cca ttt agc caa cat gct ttg acg    528
Phe Leu Gln Gln Gln Gln Leu Leu Pro Phe Ser Gln His Ala Leu Thr
                165                 170                 175 aat cct acc acc tta ttg caa cct cga gtc caa cag gca atc gca gct    576
Asn Pro Thr Thr Leu Leu Gln Pro Arg Val Gln Gln Ala Ile Ala Ala
            180                 185                 190 ggc atc tta cct tta tca ccc ttg ttc ctc caa caa tca tca gcc cta    624
Gly Ile Leu Pro Leu Ser Pro Leu Phe Leu Gln Gln Ser Ser Ala Leu
        195                 200                 205 tta cag cag tta cct ttg gtg cat tta ttg gca caa aac atc agg gca    672
Leu Gln Gln Leu Pro Leu Val His Leu Leu Ala Gln Asn Ile Arg Ala
    210                 215                 220 caa caa cta caa caa ctt gtg cta gca aac ctt gct gcc tac tct cag    720
Gln Gln Leu Gln Gln Leu Val Leu Ala Asn Leu Ala Ala Tyr Ser Gln
225                 230                 235                 240 caa caa cag ttt ctt cca ttc aac caa cta gct gca ttg aac tct gct    768
Gln Gln Gln Phe Leu Pro Phe Asn Gln Leu Ala Ala Leu Asn Ser Ala
                245                 250                 255 tct tat ttg caa caa caa caa cta cca ttc agc cag cta tct gct gcc    816
Ser Tyr Leu Gln Gln Gln Gln Leu Pro Phe Ser Gln Leu Ser Ala Ala
            260                 265                 270 tac ccc cag caa ttt ctt cca ttc aac caa ctg aca gct ttg aac tct    864
Tyr Pro Gln Gln Phe Leu Pro Phe Asn Gln Leu Thr Ala Leu Asn Ser
        275                 280                 285 cct gct tat tta cag cag caa caa cta cta cca ttc agc cag cta gct    912
Pro Ala Tyr Leu Gln Gln Gln Gln Leu Leu Pro Phe Ser Gln Leu Ala
    290                 295                 300 ggt gtg agc cct gct acc ttc ttg aca caa cca caa ttg ttg ccg ttc    960
Gly Val Ser Pro Ala Thr Phe Leu Thr Gln Pro Gln Leu Leu Pro Phe
305                 310                 315                 320 tac cag cac gct gcg cct aac gct ggc acc ctc tta caa ctg caa caa    1008
Tyr Gln His Ala Ala Pro Asn Ala Gly Thr Leu Leu Gln Leu Gln Gln
                325                 330                 335 ttg ctg cca ttc aac caa ctt gct ttg aca aac cca aca gca ttc tac    1056
Leu Leu Pro Phe Asn Gln Leu Ala Leu Thr Asn Pro Thr Ala Phe Tyr
            340                 345                 350 caa caa ccc atc att ggt ggt gcc ctc ttt tac ccg ctt gcg gcg         1101
Gln Gln Pro Ile Ile Gly Gly Ala Leu Phe Tyr Pro Leu Ala Ala
        355                 360                 365 agc gcc tta caa caa cca att gcc caa ttg caa caa caa tcc ttg gca    1149
Ser Ala Leu Gln Gln Pro Ile Ala Gln Leu Gln Gln Gln Ser Leu Ala
    370                 375                 380 cat cta acc cta caa acc att gca acg caa caa caa caa caa cag ttt    1197
His Leu Thr Leu Gln Thr Ile Ala Thr Gln Gln Gln Gln Gln Gln Phe
385                 390                 395 ctg cca tca ctg agc cac cta gcc gtg gtg aac cct gtc acc tac ttg    1245
Leu Pro Ser Leu Ser His Leu Ala Val Val Asn Pro Val Thr Tyr Leu
                405                 410                 415
400 caa cag cag ctg ctt gca tcc aac cca ctt gct ctg gcg aac gta gct    1293
Gln Gln Gln Leu Leu Ala Ser Asn Pro Leu Ala Leu Ala Asn Val Ala
            420                 425                 430 gca tac cag caa caa caa cag ctg caa cag ttt atg cca gtg ctc agt    1341
Ala Tyr Gln Gln Gln Gln Gln Leu Gln Gln Phe Met Pro Val Leu Ser
        435                 440                 445 caa cta gcc atg gtg aac cct gcc gtc tac cta caa cta ctt tca tct    1389
Gln Leu Ala Met Val Asn Pro Ala Val Tyr Leu Gln Leu Leu Ser Ser
```

```
                         450                    455                      460
agc  ccg  ctc  gcg  gtg  ggc  aat  gca  cct  acg  tac  cta  caa  caa  cag  ttg   1437
Ser  Pro  Leu  Ala  Val  Gly  Asn  Ala  Pro  Thr  Tyr  Leu  Gln  Gln  Gln  Leu
          465                      470                     475 ctg  caa  caa  att  gta  cca  gct  ctg  act  cag  cta  gct  gtg  gca  aac  cct   1485
Leu  Gln  Gln  Ile  Val  Pro  Ala  Leu  Thr  Gln  Leu  Ala  Val  Ala  Asn  Pro
480                      485                      490                      495 gct  gcc  tac  tta  caa  cag  ttg  ctt  cca  ttc  aac  caa  ctg  gct  gtg  tca   1533
Ala  Ala  Tyr  Leu  Gln  Gln  Leu  Leu  Pro  Phe  Asn  Gln  Leu  Ala  Val  Ser
               500                      505                      510 aac  tct  gct  gcg  tac  cta  caa  cag  cga  caa  cag  tta  ctt  aat  cca  ttg   1581
Asn  Ser  Ala  Ala  Tyr  Leu  Gln  Gln  Arg  Gln  Gln  Leu  Leu  Asn  Pro  Leu
          515                      520                      525 gca  gtg  gct  aac  cca  ttg  gtc  gct  acc  ttc  ctg  cag  cag  caa  caa  caa   1629
Ala  Val  Ala  Asn  Pro  Leu  Val  Ala  Thr  Phe  Leu  Gln  Gln  Gln  Gln  Gln
               530                      535                      540 ttg  ctg  cca  tac  aac  cag  ttc  tct  ttg  atg  aac  cct  gcc  ttg  cag  caa   1677
Leu  Leu  Pro  Tyr  Asn  Gln  Phe  Ser  Leu  Met  Asn  Pro  Ala  Leu  Gln  Gln
          545                      550                      555 ccc  atc  gtt  gga  ggt  gcc  atc  ttt  tag                                      1704
Pro  Ile  Val  Gly  Gly  Ala  Ile  Phe
560                      565

<210> SEQ ID NO 17
<211> LENGTH: 1637
<212> TYPE: DNA
<213> ORGANISM: Artificial Sequence
<220> FEATURE:
<223> OTHER INFORMATION: chimeric silencing construct
<221> NAME/KEY: Misc_feature
<222> LOCATION: (1)...(303)
<223> OTHER INFORMATION: 27kD gamma-zein
<221> NAME/KEY: Misc_feature
<222> LOCATION: (334)...(559)
<223> OTHER INFORMATION: 22kD alpha-zein
<221> NAME/KEY: Misc_feature
<222> LOCATION: (586)...(808)
<223> OTHER INFORMATION: 19kD alpha-zein B1
<221> NAME/KEY: Misc_feature
<222> LOCATION: (842)...(1051)
<223> OTHER INFORMATION: 19kD alpha-zein D1
<221> NAME/KEY: Misc_feature
<222> LOCATION: (1079)...(1637)
<223> OTHER INFORMATION: LKR

<400> SEQUENCE: 17
aacagccgca tccaagcccg tgccagctgc agggaacctg cggcgttggc agcaccccga      60
tcctgggcca gtgcgtcgag ttcctgaggc atcagtgcag cccgacggcg acgccctact     120
gctcgcctca gtgccagtcg ttgcggcagc agtgttgcca gcagctcagg caggtggagc     180
cgcagcaccg gtaccaggcg atcttcggct tggtcctcca gtccatcctg cagcagcagc     240
cgcaaagcgg ccaggtcgcg gggctgttgg cggcgcagat agcgcagcaa ctgacggcga     300
tgtagcggcc ccaattgcaa caacaatcct tggcacatct aaccctacaa accattgcaa     360
cgcaacaaca caacaacag tttctgccat cactgagcca cctagccgtg gtgaaccctg      420
tcacctactt gcaacagcag ctgcttgcat ccaacccact tgctctggcg aacgtagctg     480
cataccagca acaacaacag ctgcaacagt ttatgccagt gctcagtcaa ctagccatgg     540
tgaaccctgc cgtctaccta caactacttt catctagccg tcgagactac cattcagcca     600
gctatctgct gcctaccccc agcaattttct tccattcaac caactgacag ctttgaactc     660
tcctgcttat ttacagcagc aacaactact accattcagc cagctagctg gtgtgagccc     720
tgctaccttc ttgacacaac cacaattgtt gccgttctac cagcacgctg cgcctaacgc     780
```

-continued

```
tggcaccctc ttacaactgc aacaattgca ctagcggagc caagattttt gccctccttg      840
ccctccttgc tctttcagca agcgctgcta cctcgacttt tattccacaa tgctcacaac      900
aatacctctc tccggtgaca gccgcgggat tcaatacccc aactatacaa tcctacatgg      960
tacaagaggc catccaagca agcatcttac ggtcattagc attaaccctc aacaaccat       1020 atgctctatt gcaacagcca tccttagtgc atctgtatct ccaaagaatc gccccggttt      1080
agagcacaag gaggatccat catgacgctc agtatgagga tgcaggatgc agatttcag      1140 aagacctgtc agaatgcggc cttatcatag catcaaaca acccaagctg cagatgattc       1200
tttcagatag agcgtacgct ttcttttcac acacacacaa agcccaaaaa gagaatatgc      1260
cactgttaga caagatcctt gaagaagggg tgtccttgtt tgattatgag ctaattgttg     1320
gagatgatgg gaaaagatca ctagcatttg ggaaatttgc tggtagagct ggactgatag     1380
atttcttaca tggtctcgga cagcgatatt tgagccttgg atactcgact ccatttctct    1440
ctctgggaca atctcatatg tatccttcgc tcgctgcagc caaggctgca gtcattgtcg    1500
ttgcagaaga gatagcaaca tttggacttc catccggaat tgtccgata gtgtttgtgt      1560 tcactggagt tggaaacgtc tctcagggtg cgcaggagat attcaagtta ttgccccata     1620
cctttgttga tgctgag                                                     1637
```

```
<210> SEQ ID NO 18
<211> LENGTH: 537
<212> TYPE: DNA
<213> ORGANISM: Zea mays
<220> FEATURE:
<221> NAME/KEY: CDS
<222> LOCATION: (1)...(537)
<223> OTHER INFORMATION: 15kD beta-zein

<400> SEQUENCE: 18
```

```
atg aag atg gtc atc gtt ctc gtc gtg tgc ctg gct ctg tca gct gcc       48
Met Lys Met Val Ile Val Leu Val Val Cys Leu Ala Leu Ser Ala Ala
 1               5                  10                  15 agc gcc tct gca atg cag atg ccc tgc ccc tgc gcg ggg ctg cag ggc       96
Ser Ala Ser Ala Met Gln Met Pro Cys Pro Cys Ala Gly Leu Gln Gly
             20                  25                  30 ttg tac ggc gct ggc gcc ggc ctg acg acg atg atg ggc gcc ggc ggg      144
Leu Tyr Gly Ala Gly Ala Gly Leu Thr Thr Met Met Gly Ala Gly Gly
         35                  40                  45 ctg tac ccc tac gcg gag tac ctg agg cag ccg cag tgc agc ccg ctg      192
Leu Tyr Pro Tyr Ala Glu Tyr Leu Arg Gln Pro Gln Cys Ser Pro Leu
     50                  55                  60 gcg gcg gcg ccc tac tac gcc ggg tgt ggg cag ccg agc gcc atg ttc      240
Ala Ala Ala Pro Tyr Tyr Ala Gly Cys Gly Gln Pro Ser Ala Met Phe
 65                  70                  75                  80 cag ccg ctc cgg caa cag tgc tgc cag cag cag atg agg atg atg gac      288
Gln Pro Leu Arg Gln Gln Cys Cys Gln Gln Gln Met Arg Met Met Asp
                 85                  90                  95 gtg cag tcc gtc gcg cag cag ctg cag atg atg atg cag ctt gag cgt      336
Val Gln Ser Val Ala Gln Gln Leu Gln Met Met Met Gln Leu Glu Arg
            100                 105                 110 gcc gct gcc gcc agc agc agc ctg tac gag cca gct ctg atg cag cag      384
Ala Ala Ala Ala Ser Ser Ser Leu Tyr Glu Pro Ala Leu Met Gln Gln
        115                 120                 125 cag cag cag ctg ctg gca gcc cag ggt ctc aac ccc atg gcc atg atg      432
Gln Gln Gln Leu Leu Ala Ala Gln Gly Leu Asn Pro Met Ala Met Met
    130                 135                 140 atg gcg cag aac atg ccg gcc atg ggt gga ctc tac cag tac cag ctg      480
```

```
Met Ala Gln Asn Met Pro Ala Met Gly Gly Leu Tyr Gln Tyr Gln Leu
145                 150                 155                 160 ccc agc tac cgc acc aac ccc tgt ggc gtc tcc gct gcc att ccg ccc    528
Pro Ser Tyr Arg Thr Asn Pro Cys Gly Val Ser Ala Ala Ile Pro Pro
                165                 170                 175 tac tac tga                                                        537
Tyr Tyr

<210> SEQ ID NO 19
<211> LENGTH: 178
<212> TYPE: PRT
<213> ORGANISM: Zea mays

<400> SEQUENCE: 19

Met Lys Met Val Ile Val Leu Val Val Cys Leu Ala Leu Ser Ala Ala
1               5                   10                  15

Ser Ala Ser Ala Met Gln Met Pro Cys Pro Cys Ala Gly Leu Gln Gly
                20                  25                  30

Leu Tyr Gly Ala Gly Ala Gly Leu Thr Thr Met Met Gly Ala Gly Gly
            35                  40                  45

Leu Tyr Pro Tyr Ala Glu Tyr Leu Arg Gln Pro Gln Cys Ser Pro Leu
50                  55                  60

Ala Ala Ala Pro Tyr Tyr Ala Gly Cys Gly Gln Pro Ser Ala Met Phe
65                  70                  75                  80

Gln Pro Leu Arg Gln Gln Cys Cys Gln Gln Met Arg Met Met Asp
                85                  90                  95

Val Gln Ser Val Ala Gln Leu Gln Met Met Met Gln Leu Glu Arg
                100                 105                 110

Ala Ala Ala Ala Ser Ser Ser Leu Tyr Glu Pro Ala Leu Met Gln Gln
            115                 120                 125

Gln Gln Gln Leu Leu Ala Ala Gln Gly Leu Asn Pro Met Ala Met Met
130                 135                 140

Met Ala Gln Asn Met Pro Ala Met Gly Gly Leu Tyr Gln Tyr Gln Leu
145                 150                 155                 160

Pro Ser Tyr Arg Thr Asn Pro Cys Gly Val Ser Ala Ala Ile Pro Pro
                165                 170                 175

Tyr Tyr

<210> SEQ ID NO 20
<211> LENGTH: 636
<212> TYPE: DNA
<213> ORGANISM: Zea mays
<220> FEATURE:
<221> NAME/KEY: CDS
<222> LOCATION: (1)...(636)
<223> OTHER INFORMATION: high sulfur zein

<400> SEQUENCE: 20 atg gca gcc aag atg ttt gca ttg ttt gcg ctc cta gct ctt tgt gca    48
Met Ala Ala Lys Met Phe Ala Leu Phe Ala Leu Leu Ala Leu Cys Ala
1               5                   10                  15 acc gcc act agt gct acc cat atc cca ggg cac ttg tca cca cta ctg    96
Thr Ala Thr Ser Ala Thr His Ile Pro Gly His Leu Ser Pro Leu Leu
                20                  25                  30 atg cca ttg gct acc atg aac cct tgg atg cag tac tgc atg aag caa    144
Met Pro Leu Ala Thr Met Asn Pro Trp Met Gln Tyr Cys Met Lys Gln
            35                  40                  45 cag ggg gtt gcc aac ttg tta gcg tgg ccg acc ctg atg ctg cag caa    192
Gln Gly Val Ala Asn Leu Leu Ala Trp Pro Thr Leu Met Leu Gln Gln
50                  55                  60
```

```
ctg ttg gcc tca ccg ctt cag cag tgc cag atg cca atg atg atg ccg        240
Leu Leu Ala Ser Pro Leu Gln Gln Cys Gln Met Pro Met Met Met Pro
 65              70                  75                  80 ggt atg atg cca ccg atg acg atg atg ccg atg ccg agt atg atg cca        288
Gly Met Met Pro Pro Met Thr Met Met Pro Met Pro Ser Met Met Pro
                 85                  90                  95 tcg atg atg gtg ccg act atg atg tca cca atg acg atg gct agt atg        336
Ser Met Met Val Pro Thr Met Met Ser Pro Met Thr Met Ala Ser Met
                100                 105                 110 atg ccg ccg atg atg atg cca agc atg att tca cca atg acg atg ccg        384
Met Pro Pro Met Met Met Pro Ser Met Ile Ser Pro Met Thr Met Pro
            115                 120                 125 agt atg atg cct tcg atg ata atg ccg acc atg atg tca cca atg att        432
Ser Met Met Pro Ser Met Ile Met Pro Thr Met Met Ser Pro Met Ile
130                 135                 140 atg ccg agt atg atg cca cca atg atg atg ccg agc atg gtg tca cca        480
Met Pro Ser Met Met Pro Pro Met Met Met Pro Ser Met Val Ser Pro
145                 150                 155                 160 atg atg atg cca aac atg atg aca gtg cca caa tgt tac tct ggt tct        528
Met Met Met Pro Asn Met Met Thr Val Pro Gln Cys Tyr Ser Gly Ser
                165                 170                 175 atc tca cac att ata caa caa caa caa tta cca ttc atg ttc agc ccc        576
Ile Ser His Ile Ile Gln Gln Gln Gln Leu Pro Phe Met Phe Ser Pro
            180                 185                 190 aca gca atg gcg atc cca ccc atg ttc tta cag cag ccc ttt gtt ggt        624
Thr Ala Met Ala Ile Pro Pro Met Phe Leu Gln Gln Pro Phe Val Gly
        195                 200                 205 gct gca ttc tag                                                        636
Ala Ala Phe
    210

<210> SEQ ID NO 21
<211> LENGTH: 211
<212> TYPE: PRT
<213> ORGANISM: Zea mays

<400> SEQUENCE: 21

Met Ala Ala Lys Met Phe Ala Leu Phe Ala Leu Leu Ala Leu Cys Ala
 1               5                  10                  15

Thr Ala Thr Ser Ala Thr His Ile Pro Gly His Leu Ser Pro Leu Leu
             20                  25                  30

Met Pro Leu Ala Thr Met Asn Pro Trp Met Gln Tyr Cys Met Lys Gln
         35                  40                  45

Gln Gly Val Ala Asn Leu Leu Ala Trp Pro Thr Leu Met Leu Gln Gln
     50                  55                  60

Leu Leu Ala Ser Pro Leu Gln Gln Cys Gln Met Pro Met Met Met Pro
 65              70                  75                  80

Gly Met Met Pro Pro Met Thr Met Met Pro Met Pro Ser Met Met Pro
                 85                  90                  95

Ser Met Met Val Pro Thr Met Met Ser Pro Met Thr Met Ala Ser Met
                100                 105                 110

Met Pro Pro Met Met Met Pro Ser Met Ile Ser Pro Met Thr Met Pro
            115                 120                 125

Ser Met Met Pro Ser Met Ile Met Pro Thr Met Met Ser Pro Met Ile
        130                 135                 140

Met Pro Ser Met Met Pro Pro Met Met Met Pro Ser Met Val Ser Pro
145                 150                 155                 160

Met Met Met Pro Asn Met Met Thr Val Pro Gln Cys Tyr Ser Gly Ser
```

```
                165                 170                 175
Ile Ser His Ile Ile Gln Gln Gln Gln Leu Pro Phe Met Phe Ser Pro
            180                 185                 190

Thr Ala Met Ala Ile Pro Pro Met Phe Leu Gln Gln Pro Phe Val Gly
        195                 200                 205

Ala Ala Phe
    210

<210> SEQ ID NO 22
<211> LENGTH: 1623
<212> TYPE: DNA
<213> ORGANISM: Sorghum bicolor
<220> FEATURE:
<221> NAME/KEY: CDS
<222> LOCATION: (91)...(1610)
<223> OTHER INFORMATION: Sorghum legumin1

<400> SEQUENCE: 22
ctccaccgcg gtggcggccg ctctagaact agtggatccc ccgggctgca ggcagcactc      60
tgtcagtgaa gagagtgagt gagcagaagc aat ggc ggc cgc ggc gtc act ctc     114
                                  Asn Gly Gly Arg Gly Val Thr Leu
                                    1               5 cgg caa gct gct gtt tcc ctc gtc gct gtg cct ctg cct tct cct cct     162
Arg Gln Ala Ala Val Ser Leu Val Ala Val Pro Leu Pro Ser Pro Pro
     10                  15                  20 gtg ctg ctc cgg cgc cgg cgg cgc agc agc cag cag ctc atg ggg ggc     210
Val Leu Leu Arg Arg Arg Arg Arg Ser Ser Gln Gln Leu Met Gly Gly
 25                  30                  35                  40 gtc ccg ggg agg agc cgc cag gga gtg cgg ctt cga cgg caa gct gga     258
Val Pro Gly Arg Ser Arg Gln Gly Val Arg Leu Arg Arg Gln Ala Gly
                 45                  50                  55 ggc cct gga gcc gcg cca caa ggc gca gtc cga ggc cgg ctc cgt cga     306
Gly Pro Gly Ala Ala Pro Gln Gly Ala Val Arg Gly Arg Leu Arg Arg
             60                  65                  70 gta ctt cag ccg gtt cac cga agc cga ccg gga gct cac ctg cgc tgg     354
Val Leu Gln Pro Val His Arg Ser Arg Pro Gly Ala His Leu Arg Trp
         75                  80                  85 cct ctt cgc cgt ccg tgt cgt cgt cga cgc ctt ggg cct cgt gct tcc     402
Pro Leu Arg Arg Pro Cys Arg Arg Arg Arg Leu Gly Pro Arg Ala Ser
     90                  95                 100 tcg cta ctc caa cct cca ttc gct tgt cta cat cgc cca agg gag agg     450
Ser Leu Leu Gln Pro Pro Phe Ala Cys Leu His Arg Pro Arg Glu Arg
105                 110                 115                 120 gat tat tgg gtt ctc gtt tcc ggg atg cca aga aga gac cca cca tca     498
Asp Tyr Trp Val Leu Val Ser Gly Met Pro Arg Arg Asp Pro Pro Ser
                125                 130                 135 gca gca gta tgg ata cgg ata tgg ata tga aca tca tca tca gcg ccc     546
Ala Ala Val Trp Ile Arg Ile Trp Ile     Thr Ser Ser Ser Ala Pro
                140                 145                 150 tga cga gca tca caa gat cca ccg att cca aca ggg aga tgt ggt cgc     594
    Arg Ala Ser Gln Asp Pro Pro Ile Pro Thr Gly Arg Cys Gly Arg
            155                 160                 165 cat gcc cgc cgg tgc cca gca ctg gct gta caa cga cgg cga tac gcc     642
His Ala Arg Arg Cys Pro Ala Leu Ala Val Gln Arg Arg Arg Tyr Ala
        170                 175                 180 gct tgt ggc gat cta cgt ctt cga cac aaa caa caa cat caa cca gct     690
Ala Cys Gly Asp Leu Arg Leu Arg His Lys Gln Gln His Gln Pro Ala
185                 190                 195 tga gcc ttc cat gag gaa gtt ctt gct ggc tgg ggg att cag cag ggg     738
    Ala Phe His Glu Glu Val Leu Ala Gly Trp Gly Ile Gln Gln Gly
                200                 205                 210
```

```
gca gcc cca ctt cgc cga gaa cat ctt taa agg aat cga cgc ccg gtt      786
Ala Ala Pro Leu Arg Arg Glu His Leu     Arg Asn Arg Arg Pro Val
            215             220                         225 cct gag cga agc ctt ggg tgt cag cat gca agt cgc tga gaa gct tca      834
Pro Glu Arg Ser Leu Gly Cys Gln His Ala Ser Arg     Glu Ala Ser
            230             235             240 gag ccg gcg tga aca gcg agg cga gat agt ccg tgt gga gct gga gca      882
Glu Pro Ala     Thr Ala Arg Arg Asp Ser Pro Cys Gly Ala Gly Ala
        245                 250             255 tgg cct tca cct gct caa tcc acc acc gcc gtc gtt tcc atc act aca      930
Trp Pro Ser Pro Ala Gln Ser Thr Thr Ala Val Val Ser Ile Thr Thr
260             265                 270 aga cca gta cca gca tca cca aac atg cca acg cga caa cag tcg taa      978
Arg Pro Val Pro Ala Ser Pro Asn Met Pro Thr Arg Gln Gln Ser
            275             280             285 cat ctg cac cat gga ggt gag gca cag cgt cga acg cct gga tca ggc     1026
His Leu His His Gly Gly Glu Ala Gln Arg Arg Thr Pro Gly Ser Gly
290             295             300             305 cga tgt cta cag ccc tgg tgc tgg aag gat cac acg cct gac cag cca     1074
Arg Cys Leu Gln Pro Trp Cys Trp Lys Asp His Thr Pro Asp Gln Pro
            310             315             320 caa gtt ccc aat tct caa cct cat aca gat gag cgc agt tcg agt aga     1122
Gln Val Pro Asn Ser Gln Pro His Thr Asp Glu Arg Ser Ser Ser Arg
                325             330             335 cct gta tca gga cgc cat cct gtc acc gtt ctg gaa ctt caa cgc cca     1170
Pro Val Ser Gly Arg His Pro Val Thr Val Leu Glu Leu Gln Arg Pro
            340             345             350 cag tgc cat gta cac cat cag agg ctg tgc cag ggt tca ggt cgc cag     1218
Gln Cys His Val His His Gln Arg Leu Cys Gln Gly Ser Gly Arg Gln
355             360             365 cga caa cgg gac gac ggt gtt cga cgg cgt gct tcg tgc tgg gca gct     1266
Arg Gln Arg Asp Asp Gly Val Arg Arg Ala Ser Cys Trp Ala Ala
370             375             380             385 gct cat cat acc cca ggg cta cct tgt cgc cac caa ggc gca agg aga     1314
Ala His His Thr Pro Gly Leu Pro Cys Arg His Gln Gly Ala Arg Arg
                390             395             400 agg gtt tca gta cat ctc ctt cga gac gaa cca taa ctc cat ggt cag     1362
Arg Val Ser Val His Leu Leu Arg Asp Glu Pro     Leu His Gly Gln
            405             410                     415 cca cat cgc cgg gaa gaa ctc cct ctt gag cga ttt gcc ggt cgg cgt     1410
Pro His Arg Arg Glu Glu Leu Pro Leu Glu Arg Phe Ala Gly Arg Arg
            420             425             430 cat cgc cag ctc cta tgg cgt ctc gat gga gga agc tgc aga gct gaa     1458
His Arg Gln Leu Leu Trp Arg Leu Asp Gly Gly Ser Cys Arg Ala Glu
435             440             445 gaa cag tag gaa gca tga gct cgc tgt gtt tac tac tcc tcc tgg tgg     1506
Glu Gln     Glu Ala     Ala Arg Cys Val Tyr Tyr Ser Ser Trp Trp
                450             455             460 cag cta tga tca agg tca tgt tgg cag cgc cca aca gta ggc acc tga     1554
Gln Leu     Ser Arg Ser Cys Trp Gln Arg Pro Thr Val Gly Thr
465             470             475 gag tga tct acc tga ata agt act cgt gga ctg taa taa aca aag ctt     1602
Glu     Ser Thr     Ile Ser Thr Arg Gly Leu         Thr Lys Leu
                                480                     485 gtt cat gg gtaaaaaaaa aaa                                            1623
Val His
490

<210> SEQ ID NO 23
<211> LENGTH: 490
```

```
<212> TYPE: PRT
<213> ORGANISM: Sorghum bicolor

<400> SEQUENCE: 23
```

| | | | | | | | | | | | | | | | |
|---|---|---|---|---|---|---|---|---|---|---|---|---|---|---|---|
| Asn | Gly | Gly | Arg | Gly | Val | Thr | Leu | Arg | Gln | Ala | Ala | Val | Ser | Leu | Val |
| 1 | | | | 5 | | | | | 10 | | | | | 15 | |
| Ala | Val | Pro | Leu | Pro | Ser | Pro | Val | Leu | Leu | Arg | Arg | Arg | Arg | Arg | Arg |
| | | | 20 | | | | 25 | | | | | 30 | | | |
| Ser | Ser | Gln | Gln | Leu | Met | Gly | Gly | Val | Pro | Gly | Arg | Ser | Arg | Gln | Gly |
| | | | 35 | | | | 40 | | | | | 45 | | | |
| Val | Arg | Leu | Arg | Arg | Gln | Ala | Gly | Gly | Pro | Gly | Ala | Ala | Pro | Gln | Gly |
| | 50 | | | | | 55 | | | | | 60 | | | | |
| Ala | Val | Arg | Gly | Arg | Leu | Arg | Arg | Val | Leu | Gln | Pro | Val | His | Arg | Ser |
| 65 | | | | | 70 | | | | | 75 | | | | | 80 |
| Arg | Pro | Gly | Ala | His | Leu | Arg | Trp | Pro | Leu | Arg | Arg | Pro | Cys | Arg | Arg |
| | | | | 85 | | | | | 90 | | | | | 95 | |
| Arg | Arg | Leu | Gly | Pro | Arg | Ala | Ser | Ser | Leu | Leu | Gln | Pro | Pro | Phe | Ala |
| | | | 100 | | | | | 105 | | | | | 110 | | |
| Cys | Leu | His | Arg | Pro | Arg | Glu | Arg | Asp | Tyr | Trp | Val | Leu | Val | Ser | Gly |
| | | | 115 | | | | | 120 | | | | | 125 | | |
| Met | Pro | Arg | Arg | Asp | Pro | Pro | Ser | Ala | Ala | Val | Trp | Ile | Arg | Ile | Trp |
| | 130 | | | | | 135 | | | | | 140 | | | | |
| Ile | Thr | Ser | Ser | Ser | Ala | Pro | Arg | Ala | Ser | Gln | Asp | Pro | Pro | Ile | Pro |
| 145 | | | | | 150 | | | | | 155 | | | | | 160 |
| Thr | Gly | Arg | Cys | Gly | Arg | His | Ala | Arg | Arg | Cys | Pro | Ala | Leu | Ala | Val |
| | | | | 165 | | | | | 170 | | | | | 175 | |
| Gln | Arg | Arg | Arg | Tyr | Ala | Ala | Cys | Gly | Asp | Leu | Arg | Leu | Arg | His | Lys |
| | | | 180 | | | | | 185 | | | | | 190 | | |
| Gln | Gln | His | Gln | Pro | Ala | Ala | Phe | His | Glu | Glu | Val | Leu | Ala | Gly | Trp |
| | | | 195 | | | | | 200 | | | | | 205 | | |
| Gly | Ile | Gln | Gln | Gly | Ala | Ala | Pro | Leu | Arg | Arg | Glu | His | Leu | Arg | Asn |
| | 210 | | | | | 215 | | | | | 220 | | | | |
| Arg | Arg | Pro | Val | Pro | Glu | Arg | Ser | Leu | Gly | Cys | Gln | His | Ala | Ser | Arg |
| 225 | | | | | 230 | | | | | 235 | | | | | 240 |
| Glu | Ala | Ser | Glu | Pro | Ala | Thr | Ala | Arg | Arg | Asp | Ser | Pro | Cys | Gly | Ala |
| | | | | 245 | | | | | 250 | | | | | 255 | |
| Gly | Ala | Trp | Pro | Ser | Pro | Ala | Gln | Ser | Thr | Thr | Ala | Val | Val | Ser | Ile |
| | | | 260 | | | | | 265 | | | | | 270 | | |
| Thr | Thr | Arg | Pro | Val | Pro | Ala | Ser | Pro | Asn | Met | Pro | Thr | Arg | Gln | Gln |
| | | | | 275 | | | | | 280 | | | | | 285 | |
| Ser | His | Leu | His | His | Gly | Gly | Glu | Ala | Gln | Arg | Arg | Thr | Pro | Gly | Ser |
| | 290 | | | | | 295 | | | | | 300 | | | | |
| Gly | Arg | Cys | Leu | Gln | Pro | Trp | Cys | Trp | Lys | Asp | His | Thr | Pro | Asp | Gln |
| 305 | | | | | 310 | | | | | 315 | | | | | 320 |
| Pro | Gln | Val | Pro | Asn | Ser | Gln | Pro | His | Thr | Asp | Glu | Arg | Ser | Ser | Ser |
| | | | | 325 | | | | | 330 | | | | | 335 | |
| Arg | Pro | Val | Ser | Gly | Arg | His | Pro | Val | Thr | Val | Leu | Glu | Leu | Gln | Arg |
| | | | 340 | | | | | 345 | | | | | 350 | | |
| Pro | Gln | Cys | His | Val | His | His | Gln | Arg | Leu | Cys | Gln | Gly | Ser | Gly | Arg |
| | | | | 355 | | | | | 360 | | | | | 365 | |
| Gln | Arg | Gln | Arg | Asp | Asp | Gly | Val | Arg | Arg | Ala | Ser | Cys | Trp | Ala | |
| | 370 | | | | | 375 | | | | | 380 | | | | |
| Ala | Ala | His | His | Thr | Pro | Gly | Leu | Pro | Cys | Arg | His | Gln | Gly | Ala | Arg |
| 385 | | | | | 390 | | | | | 395 | | | | | 400 |

```
Arg Arg Val Ser Val His Leu Leu Arg Asp Glu Pro Leu His Gly Gln
                405                 410                 415

Pro His Arg Arg Glu Glu Leu Pro Leu Glu Arg Phe Ala Gly Arg Arg
            420                 425                 430

His Arg Gln Leu Leu Trp Arg Leu Asp Gly Gly Ser Cys Arg Ala Glu
        435                 440                 445

Glu Gln Glu Ala Ala Arg Cys Val Tyr Tyr Ser Ser Trp Gln Leu
    450                 455                 460

Ser Arg Ser Cys Trp Gln Arg Pro Thr Val Gly Thr Glu Ser Thr Ile
465                 470                 475                 480

Ser Thr Arg Gly Leu Thr Lys Leu Val His
            485                 490

<210> SEQ ID NO 24
<211> LENGTH: 1712
<212> TYPE: DNA
<213> ORGANISM: Saccharum officinale
<220> FEATURE:
<221> NAME/KEY: CDS
<222> LOCATION: (100)...(1677)
<223> OTHER INFORMATION: Sugarcane legumin1

<400> SEQUENCE: 24
cgcctgcagg taccggtccg gaattcccgg gtcgacccac gcgtccgccc acgcgtccgc     60
tgtcgtcagt cgtcactgaa gagagtgagc agaagcaac aat ggc ggc ggc act        114
                                             Asn Gly Gly Gly Thr
                                                  1               5 ctc cgg caa gct gct gcc gct tcc ctc ctc cct gtg cct gtg cct gct       162
Leu Arg Gln Ala Ala Ala Ala Ser Leu Leu Pro Val Pro Val Pro Ala
             10                  15                  20 tct cct cct gtg ctg ctc cgg ctc tgg cgc cgg cgc agc cag cag ctc       210
Ser Pro Pro Val Leu Leu Arg Leu Trp Arg Arg Arg Ser Gln Gln Leu
             25                  30                  35 atg ggg ggc gtc ccg ggg agg agc cgc cag gga gtg cgg ttt cga cga       258
Met Gly Gly Val Pro Gly Arg Ser Arg Gln Gly Val Arg Phe Arg Arg
         40                  45                  50 caa gct gga ggc cct gga gcc gcg cca caa ggt gca gtc cga ggc cgg       306
Gln Ala Gly Gly Pro Gly Ala Ala Pro Gln Gly Ala Val Arg Gly Arg
     55                  60                  65 ctc cgt cga gta ctt cag ccg att cac cga agc cga ccg gga gct cac       354
Leu Arg Arg Val Leu Gln Pro Ile His Arg Ser Arg Pro Gly Ala His
 70                  75                  80                  85 ctg cgc cgg cat ctt cgc cgt ccg cgt cgt cgt gga cgc ctt ggg cct       402
Leu Arg Arg His Leu Arg Arg Pro Arg Arg Arg Gly Arg Leu Gly Pro
                 90                  95                 100 cct tct tcc tcg cta ctc caa cct cca ttc tct ggt cta cat cat aca       450
Pro Ser Ser Ser Leu Leu Gln Pro Pro Phe Ser Gly Leu His His Thr
            105                 110                 115 agg gag agg gat tat tgg gtt ctc gtt tcc ggg atg cca aga aga gac       498
Arg Glu Arg Asp Tyr Trp Val Leu Val Ser Gly Met Pro Arg Arg Asp
        120                 125                 130 cca cca tca gca gca gta tgc ata cgg ata tgg ata tga aca tca tca       546
Pro Pro Ser Ala Ala Val Cys Ile Arg Ile Trp Ile     Thr Ser Ser
    135                 140                 145 tca tca gcg ccc tga cga gca tca caa gat cca ccg att cga aca ggg       594
Ser Ser Ala Pro     Arg Ala Ser Gln Asp Pro Pro Ile Arg Thr Gly
150                 155                 160 aga cgt ggt ggc cat gcc ggc cgg tgc tca gca ctg gct gta caa cga       642
Arg Arg Gly Gly His Ala Gly Arg Cys Ser Ala Leu Ala Val Gln Arg
            165                 170                 175
```

```
cgg caa tgc gcc gct tgt ggc gat cta cgt ctt cga cac aaa caa caa    690
Arg Gln Cys Ala Ala Cys Gly Asp Leu Arg Leu Arg His Lys Gln Gln
180             185                 190                 195 cat caa cca gct tga gcc ttc cat gag gaa gtt ctt gct ggc tgg ggg    738
His Gln Pro Ala     Ala Phe His Glu Glu Val Leu Ala Gly Trp Gly
        200                 205                 210 att cag caa ggg gca gat cca ctt cgc cga gaa cat ctt taa agg aat    786
Ile Gln Gln Gly Ala Asp Pro Leu Arg Arg Glu His Leu     Arg Asn
215                 220                 225 cga cgc ccg gtt cct gag cga agc cct ggg tgt cag cat gaa tgt cac    834
Arg Arg Pro Val Pro Glu Arg Ser Pro Gly Cys Gln His Glu Cys His
230                 235                 240 taa gaa gct tca gag ccg aca tga cca gcg ggg cga aat agt ccg tgt    882
    Glu Ala Ser Glu Pro Thr     Pro Ala Gly Arg Asn Ser Pro Cys
                245                 250                 255 gga gct gga gca tgg cct tca cct cct gaa tcc acc atc gtc gtc gtc    930
Gly Ala Gly Ala Trp Pro Ser Pro Pro Glu Ser Thr Ile Val Val Val
        260                 265                 270 att tcc atc act aca aga cca gta cca aca tca cca aac atg tca acg    978
Ile Ser Ile Thr Thr Arg Pro Val Pro Thr Ser Pro Asn Met Ser Thr
275                 280                 285 cga cga cag cca taa cat ctg cgc cat ggc ggt gag gca cag cgt cga   1026
Arg Arg Gln Pro     His Leu Arg His Gly Gly Glu Ala Gln Arg Arg
                290                 295                 300 acg cct tga tca ggc cga cgt cta cag ccc tgg tgc tgg gag gat cac   1074
Thr Pro     Ser Gly Arg Arg Leu Gln Pro Trp Cys Trp Glu Asp His
                305                 310                 315 acg cct gac cag cca caa gtt ccc aat tct caa cct cat aca gat gag   1122
Thr Pro Asp Gln Pro Gln Val Pro Asn Ser Gln Pro His Thr Asp Glu
        320                 325                 330 cgc ggt gcg agt aga cct ata tca gga tgc cat cct gtc gcc gtt ctg   1170
Arg Gly Ala Ser Arg Pro Ile Ser Gly Cys His Pro Val Ala Val Leu
335                 340                 345 gaa ctt caa cgc cca cag cgc cat gta cac cat cag agg ctg tgc cag   1218
Glu Leu Gln Arg Pro Gln Arg His Val His His Gln Arg Leu Cys Gln
350                 355                 360                 365 ggt tca ggt cgc cag cga caa tgg gac gac cgt gtt cga cgg cgt gct   1266
Gly Ser Gly Arg Gln Arg Gln Trp Asp Asp Arg Val Arg Arg Arg Ala
            370                 375                 380 tcg tcc tgg gca gct gtt cat cat acc cca ggg cta cct tgt cgc cac   1314
Ser Ser Trp Ala Ala Val His His Thr Pro Gly Leu Pro Cys Arg His
                385                 390                 395 caa ggc gca agg aga agg gtt cca gta cat atc cat cga gat gaa ccc   1362
Gln Gly Ala Arg Arg Arg Val Pro Val His Ile His Arg Asp Glu Pro
        400                 405                 410 caa ctc cat ggt cag cca cat tgc cgg gaa gaa ctc cgt ctt cag caa   1410
Gln Leu His Gly Gln Pro His Cys Arg Glu Glu Leu Arg Leu Gln Gln
415                 420                 425 ttt gcc ggt cgg cat cat cgc cag ctc gta tgg cgt ctc cat gga gga   1458
Phe Ala Gly Arg His His Arg Gln Leu Val Trp Arg Leu His Gly Gly
430                 435                 440                 445 agc tgc aga gct gaa gaa cag tag aaa gca tga gct tgc tgt gtt tac   1506
Ser Cys Arg Ala Glu Glu Gln     Lys Ala     Ala Cys Cys Val Tyr
                450                             455 tcc tgg tgg cag cta tga tca agg tca tgt tgg cag cgc cca aca gta   1554
Ser Trp Trp Gln Leu     Ser Arg Ser Cys Trp Gln Arg Pro Thr Val
                460                 465                 470 ggc acc tta gag tga tct gct tga ata agt tat cgt gga ctg taa taa   1602
Gly Thr Leu Glu     Ser Ala     Ile Ser Tyr Arg Gly Leu
        475             480                 485
```

```
aca aag ctt gtt cat ggt taa act gca tgt ctg cat gga tga atc ttt    1650
Thr Lys Leu Val His Gly     Thr Ala Cys Leu His Gly     Ile Phe
    490                 495                 500 caa cta cat agc tcg tca aat aaa aca actgaactga agtgagtaat           1697
Gln Leu His Ser Ser Ser Asn Lys Thr
505 gtttcaaaaa aaaaa                                                    1712

<210> SEQ ID NO 25
<211> LENGTH: 509
<212> TYPE: PRT
<213> ORGANISM: Saccharum officinale

<400> SEQUENCE: 25

Asn Gly Gly Gly Thr Leu Arg Gln Ala Ala Ala Ser Leu Leu Pro
  1               5                  10                  15

Val Pro Val Pro Ala Ser Pro Pro Val Leu Arg Leu Trp Arg Arg
             20                  25                  30

Arg Ser Gln Gln Leu Met Gly Gly Val Pro Gly Arg Ser Arg Gln Gly
             35                  40                  45

Val Arg Phe Arg Arg Gln Ala Gly Gly Pro Gly Ala Ala Pro Gln Gly
 50                  55                  60

Ala Val Arg Gly Arg Leu Arg Arg Val Leu Gln Pro Ile His Arg Ser
 65                  70                  75                  80

Arg Pro Gly Ala His Leu Arg His Leu Arg Arg Pro Arg Arg
                 85                  90                  95

Gly Arg Leu Gly Pro Pro Ser Ser Leu Leu Gln Pro Pro Phe Ser
                100                 105                 110

Gly Leu His His Thr Arg Glu Arg Asp Tyr Trp Val Leu Val Ser Gly
            115                 120                 125

Met Pro Arg Arg Asp Pro Pro Ser Ala Ala Val Cys Ile Arg Ile Trp
    130                 135                 140

Ile Thr Ser Ser Ser Ser Ala Pro Arg Ala Ser Gln Asp Pro Pro Ile
145                 150                 155                 160

Arg Thr Gly Arg Arg Gly Gly His Ala Gly Arg Cys Ser Ala Leu Ala
                165                 170                 175

Val Gln Arg Arg Gln Cys Ala Ala Cys Gly Asp Leu Arg Leu Arg His
            180                 185                 190

Lys Gln Gln His Gln Pro Ala Ala Phe His Glu Glu Val Leu Ala Gly
        195                 200                 205

Trp Gly Ile Gln Gln Gly Ala Asp Pro Leu Arg Arg Glu His Leu Arg
    210                 215                 220

Asn Arg Arg Pro Val Pro Glu Arg Ser Pro Gly Cys Gln His Glu Cys
225                 230                 235                 240

His Glu Ala Ser Glu Pro Thr Pro Ala Gly Arg Asn Ser Pro Cys Gly
                245                 250                 255

Ala Gly Ala Trp Pro Ser Pro Glu Ser Thr Ile Val Val Ile
            260                 265                 270

Ser Ile Thr Thr Arg Pro Val Pro Thr Ser Pro Asn Met Ser Thr Arg
        275                 280                 285

Arg Gln Pro His Leu Arg His Gly Gly Glu Ala Gln Arg Arg Thr Pro
    290                 295                 300

Ser Gly Arg Arg Leu Gln Pro Trp Cys Trp Glu Asp His Thr Pro Asp
305                 310                 315                 320

Gln Pro Gln Val Pro Asn Ser Gln Pro His Thr Asp Glu Arg Gly Ala
                325                 330                 335
```

```
Ser Arg Pro Ile Ser Gly Cys His Pro Val Ala Val Leu Glu Leu Gln
            340                 345                 350

Arg Pro Gln Arg His Val His His Gln Arg Leu Cys Gln Gly Ser Gly
        355                 360                 365

Arg Gln Arg Gln Trp Asp Asp Arg Val Arg Arg Ala Ser Ser Trp
370                 375                 380

Ala Ala Val His His Thr Pro Gly Leu Pro Cys Arg His Gln Gly Ala
385                 390                 395                 400

Arg Arg Arg Val Pro Val His Ile His Arg Asp Glu Pro Gln Leu His
                405                 410                 415

Gly Gln Pro His Cys Arg Glu Glu Leu Arg Leu Gln Gln Phe Ala Gly
            420                 425                 430

Arg His His Arg Gln Leu Val Trp Arg Leu His Gly Gly Ser Cys Arg
                435                 440                 445

Ala Glu Glu Gln Lys Ala Ala Cys Cys Val Tyr Ser Trp Trp Gln Leu
450                 455                 460

Ser Arg Ser Cys Trp Gln Arg Pro Thr Val Gly Thr Leu Glu Ser Ala
465                 470                 475                 480

Ile Ser Tyr Arg Gly Leu Thr Lys Leu Val His Gly Thr Ala Cys Leu
                485                 490                 495

His Gly Ile Phe Gln Leu His Ser Ser Asn Lys Thr
            500                 505
```

<210> SEQ ID NO 26
<211> LENGTH: 1510
<212> TYPE: DNA
<213> ORGANISM: Zea mays
<220> FEATURE:
<221> NAME/KEY: promoter
<222> LOCATION: (1)...(1510)
<223> OTHER INFORMATION: GZ-W64A promoter

<400> SEQUENCE: 26

```
ttatataatt tataagctga aacaacccgg ccctaaagca ctatcgtatc acctatctga     60
aataagtcac gggtttcgaa cgtccacttg cgtcgcacgg aattgcatgt ttcttgttgg    120
aagcatattc acgcaatctc cacacataaa ggtttatgta taaacttaca tttagctcag    180
tttaattaca gtcttatttg gatgcatatg tatggttctc aatccatata agttagagta    240
aaaaataagt ttaaatttta tcttaattca ctccaacata tatggattga gtacaatact    300
catgtgcatc caaacaaact acttatattg aggtgaattt ggatagaaat taaactaact    360
tacacactaa gccaatcttt actatattaa agcaccagtt tcaacgatcg tcccgcgtca    420
atattattaa aaaactccta catttctttta taatcaaccc gcactcttat aatctcttct    480
ctactactat aataagagag tttatgtaca aaataaggtg aaattatgta taagtgttct    540
ggatattggt tgttggctcc atattcacac aacctaatca atagaaaaca tatgttttat    600
taaaacaaaa tttatcatat atcatatata tatatataca tatatatata taaaccgtag    660
caatgcacgg gcataatact agtgcaactt aatacatgtg tgtattaaga tgaataagag    720
ggtatccaaa taaaaaactt gttcgcttac gtctggatcg aaaggggttg gaaacgatta    780
aatctcttcc tagtcaaaat tgaatagaag gagatttaat ctctcccaat ccccttcgat    840
catccaggtg caaccgtata agtcctaaag tggtgaggaa cacgaaacaa ccatgcattg    900
gcatgtaaag ctccaagaat tgttgtatc cttaacaact cacagaacat caaccaaaat    960
tgcacgtcaa gggtattggg taagaaacaa tcaaacaaat cctctctgtg tgcaaagaaa   1020
```

```
cacggtgagt catgccgaga tcatactcat ctgatataca tgcttacagc tcacaagaca    1080
ttacaaacaa ctcatattgc attacaaaga tcgtttcatg aaaaataaaa taggccggac    1140
aggacaaaaa tccttgacgt gtaaagtaaa tttacaacaa aaaaaaagcc atatgtcaag    1200
ctaaatctaa ttcgttttac gtagatcaac aacctgtaga aggcaacaaa actgagccac    1260
gcagaagtac agaatgattc cagatgaacc atcgacgtgc tacgtaaaga gagtgacgag    1320
tcatatacat ttggcaagaa accatgaagc tgcctacagc cgtctcggtg gcataagaac    1380
acaagaaatt gtgttaatta atcaaagcta taaataacgc tcgcatgcct gtgcacttct    1440
ccatcaccac cactgggtct tcagaccatt agctttatct actccagagc gcagaagaac    1500
ccgatcgaca                                                          1510

<210> SEQ ID NO 27
<211> LENGTH: 492
<212> TYPE: DNA
<213> ORGANISM: Zea mays
<220> FEATURE:
<221> NAME/KEY: terminator
<222> LOCATION: (1)...(492)
<223> OTHER INFORMATION: GZ-W64A terminator

<400> SEQUENCE: 27
gatccccggc ggtgtccccc actgaagaaa ctatgtgctg tagtatagcc gctgcccgct      60
ggctagctag ctagttgagt catttagcgg cgatgattga gtaataatgt gtcacgcatc     120
accatgcatg ggtggcagtg tcagtgtgag caatgacctg aatgaacaat tgaaatgaaa     180 agaaaaagt attgttccaa attaaacgtt ttaacctttt aataggttta tacaataatt      240
gatatatgtt ttctgtatat gtctaatttg ttatcatcca tttagatata gacaaaaaaa     300
atctaagaac taaaacaaat gctaatttga aatgaaggga gtatatattg ggataatgtc     360
gatgagatcc ctcgtaatat caccgacatc acacgtgtcc agttaatgta tcagtgatac     420
gtgtattcac atttgttgcg cgtaggcgta cccaacaatt ttgatcgact atcagaaagt     480
caacggaagc ga                                                        492
```